United States Patent
Herrendorff et al.

(10) Patent No.: US 11,091,591 B2
(45) Date of Patent: Aug. 17, 2021

(54) CARBOHYDRATE LIGANDS THAT BIND TO ANTIBODIES AGAINST GLYCOEPITOPES OF GLYCOSPHINGOLIPIDS

(71) Applicant: UNIVERSITÄT BASEL, Basel (CH)

(72) Inventors: Ruben Herrendorff, Basel (CH); Beat Ernst, Magden (CH); Andreas Steck, Epalinges (CH); Hélène Pfister, Basel (CH); Giulio Navarra, Binningen (CH)

(73) Assignee: UNIVERSITÄT BASEL, Basel (CH)

( * ) Notice: Subject to any disclaimer, the term of this patent is extended or adjusted under 35 U.S.C. 154(b) by 163 days.

(21) Appl. No.: 15/760,398

(22) PCT Filed: Sep. 14, 2016

(86) PCT No.: PCT/EP2016/071711
§ 371 (c)(1),
(2) Date: Mar. 15, 2018

(87) PCT Pub. No.: WO2017/046172
PCT Pub. Date: Mar. 23, 2017

(65) Prior Publication Data
US 2018/0251602 A1   Sep. 6, 2018

(30) Foreign Application Priority Data
Sep. 16, 2015 (EP) .................... 15185552

(51) Int. Cl.
*C07H 15/12* (2006.01)
*C08G 69/48* (2006.01)
*A61P 25/00* (2006.01)

(52) U.S. Cl.
CPC .............. *C08G 69/48* (2013.01); *A61P 25/00* (2018.01); *C07H 15/12* (2013.01)

(58) Field of Classification Search
CPC ........... A61P 25/00; C07K 2/00; C08G 69/48; C07H 15/12
(Continued)

(56) References Cited

U.S. PATENT DOCUMENTS 5,155,004 A   10/1992 Kojima
5,470,843 A   11/1995 Stahl et al.
(Continued)

FOREIGN PATENT DOCUMENTS

CA   2 332 571 A1   1/2000
CN   101123990 A    2/2008
(Continued)

OTHER PUBLICATIONS

Thoma et al, J. Am. Chem. Soc., 2001, 123(41), 10113-10114.*
(Continued)

*Primary Examiner* — Ganapathy Krishnan
(74) *Attorney, Agent, or Firm* — Fenwick & West LLP

(57) ABSTRACT

The invention relates to carbohydrate ligands and moieties, respectively, mimicking glycoepitopes comprised by glycosphingolipids of the nervous system, particularly glycoepitopes comprised by glycosphingolipids of the cerebroside, the globoside-, the ganglioside- and the sulfoglucuronyl paragloboside type, which are bound by anti-glycan antibodies associated with neurological diseases. The invention further relates to the use of these carbohydrate ligands/moieties, in diagnosis as well as for the treatment of neurological diseases associated with anti-glycan antibodies. In particular, the invention relates to compounds of formula (I) and (II) and to therapeutically acceptable polymers comprising a multitude of these compounds, including polymers with loading of one compound of formula (I) or (II) or combinations of several compounds of formula (I), and/or (II). The compounds of formula (I) are defined as:

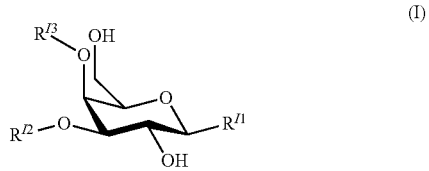

wherein
$R^{J1}$ is Z or

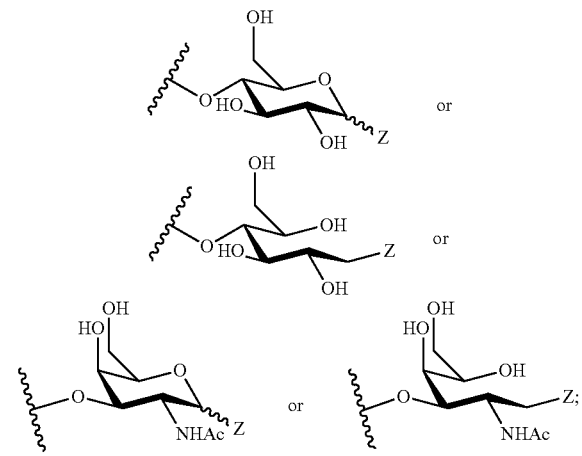

wherein
$R^{J2}$ is H, $SO_3H$, or (Continued)

-continued
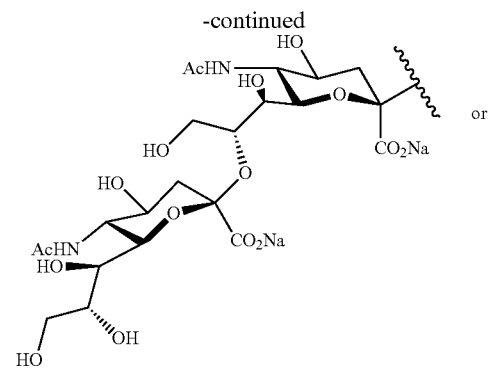
or
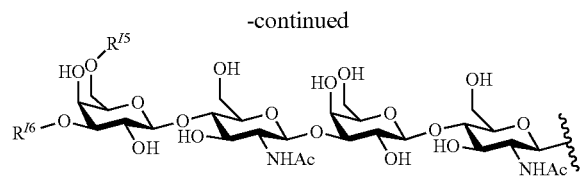
wherein
$R^{13}$ is H or
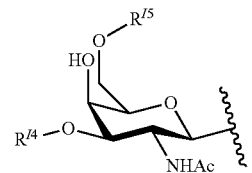
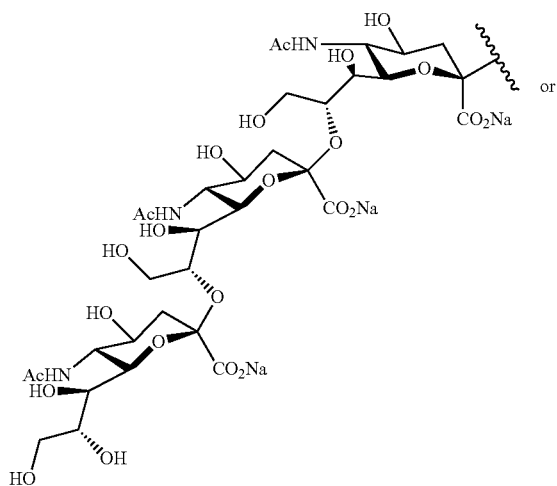
wherein
$R^{14}$ is H or
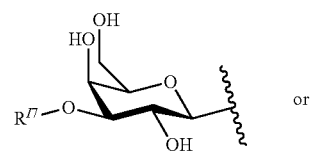
or
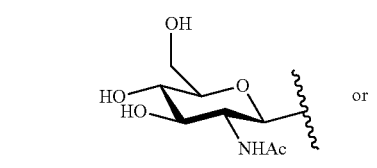
or
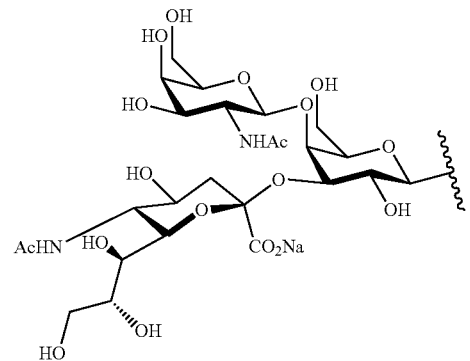
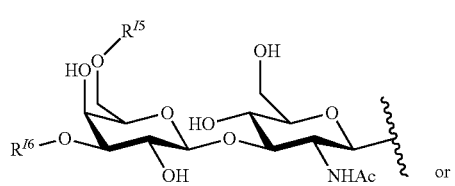
or
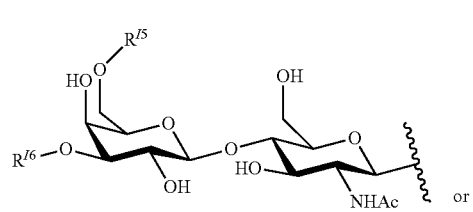
or
wherein
$R^{15}$ and $R^{16}$ are independently H or
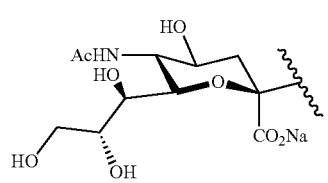

wherein
R^{I1} is H or

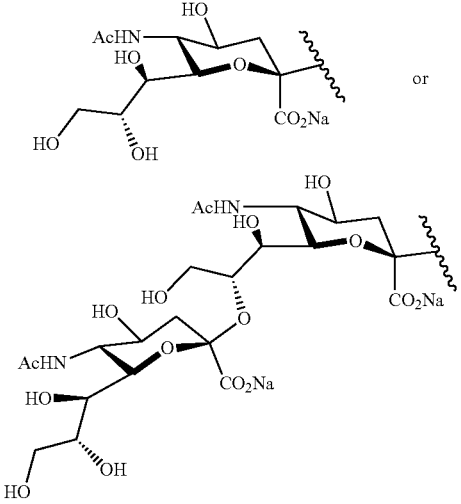

and compounds of formula (II) are defined as:

(II)

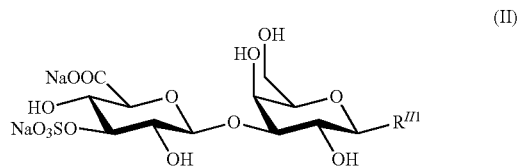

wherein
R^{II1} is Z or

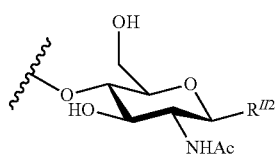

wherein
R^{II2} is Z or

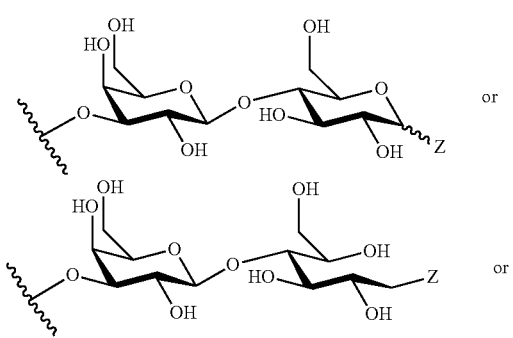

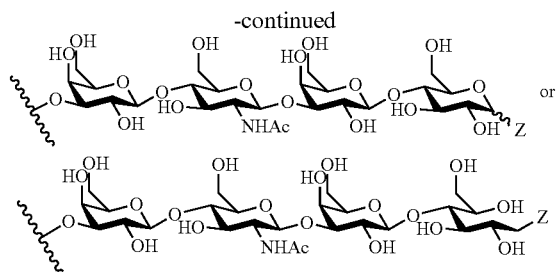

wherein Z is —N($R^a$)—A—B—CH$_2$—(CH$_2$)$_q$—SH, wherein
$R^a$ is H, C$_1$-C$_4$-alky, C$_1$-C$_4$alkoxy, CH$_2$C$_6$H$_5$, CH$_2$CH$_2$C$_6$H$_5$, OCH$_2$C$_6$H$_5$, or OCH$_2$CH$_2$C$_6$H$_5$;
A is C$_1$-C$_7$-alkylene, C$_1$-C$_7$-alkoxy, C$_1$-C$_4$-alkyl—(OCH$_2$CH$_2$)$_p$O—C$_1$-C$_4$-alkyl, or C$_1$-C$_7$-alkoxy-$R^b$, wherein $R^b$ is an optionally substituted aryl or an optionally substituted heteroaryl, and wherein p is 0 to 6, preferably p is 1, 2 or 3, and further preferably p is 1;
B is NHC(O), S or CH$_2$;
q is 0 to 6, preferably q is 1, 2, 3 or 4, and further preferably q is 1 or 2.

14 Claims, 4 Drawing Sheets

(58) Field of Classification Search
USPC .......................................................... 514/54
See application file for complete search history.

(56) References Cited

U.S. PATENT DOCUMENTS

| | | |
|---|---|---|
| 5,695,759 A | 12/1997 | Good et al. |
| 5,846,951 A | 12/1998 | Gregoriadis |
| 5,874,411 A | 2/1999 | Srivastava et al. |
| 5,977,080 A | 11/1999 | Rosen et al. |
| 5,985,578 A | 11/1999 | Pestronk |
| 6,020,140 A | 2/2000 | Pestronk |
| 6,037,467 A | 3/2000 | Stahl et al. |
| 6,077,681 A | 6/2000 | Pestronk |
| 6,114,388 A | 9/2000 | Geffard |
| 6,399,071 B1 | 6/2002 | Duthaler et al. |
| 6,399,578 B1 | 6/2002 | Jack et al. |
| 6,491,922 B1 | 12/2002 | Ho |
| 6,994,970 B1 | 2/2006 | Ronspeck et al. |
| 7,205,382 B2 | 4/2007 | Ronspeck et al. |
| 7,294,615 B1 | 11/2007 | Bovin et al. |
| 7,612,183 B2 | 11/2009 | Ellis et al. |
| 8,071,731 B2 | 12/2011 | Ellis et al. |
| 8,420,593 B1 | 4/2013 | Miller |
| 9,719,987 B2 | 8/2017 | Maiiez Mendiluce |
| 9,994,605 B2 * | 6/2018 | Ernst ................... C07H 15/207 |
| 2002/0164347 A1 | 11/2002 | Duthaler et al. |
| 2002/0177161 A1 | 11/2002 | Latov et al. |
| 2003/0049692 A1 | 3/2003 | Latov et al. |
| 2004/0038311 A1 | 2/2004 | Pestronk |
| 2004/0043431 A1 | 3/2004 | Voidani |
| 2004/0087765 A1 | 5/2004 | Ronspeck et al. |
| 2004/0156840 A1 | 8/2004 | Witte et al. |
| 2006/0165681 A1 | 7/2006 | Ellis et al. |
| 2006/0280685 A1 | 12/2006 | Popko et al. |
| 2007/0244038 A1 | 10/2007 | Varki et al. |
| 2008/0220988 A1 | 9/2008 | Zhou |
| 2009/0155292 A1 | 6/2009 | Santamaria et al. |
| 2009/0169636 A1 | 7/2009 | O'Hagan et al. |
| 2009/0258792 A1 | 10/2009 | Wang et al. |
| 2011/0085981 A1 | 4/2011 | Wang |

(56) References Cited

U.S. PATENT DOCUMENTS

| | | |
|---|---|---|
| 2012/0039984 A1 | 2/2012 | Boons et al. |
| 2015/0283247 A1 | 10/2015 | Auzely-Velty et al. |

FOREIGN PATENT DOCUMENTS

| | | | |
|---|---|---|---|
| CN | 101863930 A | 10/2010 | |
| CN | 101917985 A | 12/2010 | |
| CN | 103108654 A | 5/2013 | |
| CN | 104661684 A | 5/2015 | |
| DE | 195 26 675 A1 | 3/1996 | |
| DE | 199 30 177 A1 | 1/2001 | |
| EP | 0 601 417 A2 | 6/1994 | |
| EP | 0 662 611 A2 | 7/1995 | |
| EP | 2 698 636 A1 | 2/2014 | |
| EP | 2 727 597 A1 | 5/2014 | |
| EP | 2727597 A1 * | 5/2014 | ........... A61K 31/728 |
| JP | 2006-347993 A | 12/2006 | |
| RU | 2303461 C9 | 12/2007 | |
| RU | 2483736 C2 | 6/2013 | |
| WO | WO 1992/022301 A1 | 12/1992 | |
| WO | WO 1993/003375 A1 | 2/1993 | |
| WO | WO 1993/003735 A1 | 3/1993 | |
| WO | WO 1996/015810 A1 | 5/1996 | |
| WO | WO 1997/007810 A1 | 3/1997 | |
| WO | WO 1997/019105 A1 | 5/1997 | |
| WO | WO 98/47915 A1 * | 10/1998 | ............. A61K 47/48 |
| WO | WO 1998/047915 A1 | 10/1998 | |
| WO | WO 1998/049558 A1 | 11/1998 | |
| WO | WO 1999/012944 A2 | 3/1999 | |
| WO | WO 1999/052561 A1 | 10/1999 | |
| WO | WO 1999/053757 A1 | 10/1999 | |
| WO | WO 2000/020871 A1 | 4/2000 | |
| WO | WO 2000/029439 A1 | 5/2000 | |
| WO | WO 2000/033887 A2 | 6/2000 | |
| WO | WO 2000/034296 A2 | 6/2000 | |
| WO | WO 2000/050447 A1 | 8/2000 | |
| WO | WO 2001/002018 A2 | 1/2001 | |
| WO | WO 2001/021660 A1 | 3/2001 | |
| WO | WO 2002/016414 A2 | 2/2002 | |
| WO | WO 2002/018950 A1 | 3/2002 | |
| WO | WO 2002/038592 A2 | 5/2002 | |
| WO | WO 2002/098459 A2 | 12/2002 | |
| WO | WO 2003/002127 A1 | 1/2003 | |
| WO | WO 2003/068822 A2 | 8/2003 | |
| WO | WO 2004/015420 A1 | 2/2004 | |
| WO | WO 2004/062599 A2 | 7/2004 | |
| WO | WO 2004/065400 A1 | 8/2004 | |
| WO | WO 2005/037293 A1 | 4/2005 | |
| WO | WO 2005/051429 A2 | 6/2005 | |
| WO | WO 2005/051920 A2 | 6/2005 | |
| WO | WO 2005/054264 A2 | 6/2005 | |
| WO | WO 2005/080985 A2 | 9/2005 | |
| WO | WO 2005/085264 A1 | 9/2005 | |
| WO | WO 2005/118609 A2 | 12/2005 | |
| WO | WO 2006/037979 A2 | 4/2006 | |
| WO | WO 2006/068720 A2 | 6/2006 | |
| WO | WO 2007/138263 A1 | 12/2007 | |
| WO | WO 2008/002449 A2 | 1/2008 | |
| WO | WO 2008/030505 A2 | 3/2008 | |
| WO | WO 2008/059003 A1 | 5/2008 | |
| WO | WO 2008/151847 A1 | 12/2008 | |
| WO | WO 2009/017795 A1 | 2/2009 | |
| WO | WO 2009/101475 A2 | 8/2009 | |
| WO | WO 2009/102820 A2 | 8/2009 | |
| WO | WO 2009/126933 A2 | 10/2009 | |
| WO | WO 2011/031472 A2 | 3/2011 | |
| WO | WO 2011/073685 A1 | 6/2011 | |
| WO | WO 2011/101870 A1 | 8/2011 | |
| WO | WO 2011/156774 A2 | 12/2011 | |
| WO | WO 2012/080444 A1 | 6/2012 | |
| WO | WO 2013/044044 A2 | 3/2013 | |
| WO | WO 2014/027302 A1 | 2/2014 | |
| WO | WO 2014/072330 A1 | 5/2014 | |
| WO | WO 2014/175838 A1 | 10/2014 | |
| WO | WO 2015/007326 A1 | 1/2015 | |
| WO | WO 2015/116775 A1 | 8/2015 | |
| WO | WO 2015/136027 A1 | 9/2015 | |
| WO | WO 2017/046172 A1 | 3/2017 | |

OTHER PUBLICATIONS

Song et al, Biomaterials, 2012, 33, 6889-6897.*
Bohorov et al, Glycobiology, 2006, 16(12), 21C-27C.*
International Search Report dated Oct. 26, 2016 in corresponding International Patent Application No. PCT/EP2016/071711.
Willison, Hugh J et al., "Peripheral Neuropathies and Anti-Glycolipid Antibodies," Brain 125(12):2591-2625 (2002) (Oxford University Press, Oxford, GB).
Miyase, T. et al., "Linderniosides A and B, Oleanane Saponins From Lindernia Pyxidaria," Phytochemistry, vol. 40, No. 5, Nov. 1995, pp. 1499-1502.
Skaar, I. et al., "Purple anthocyanin colouration on lower (abaxial) leaf surface of *Hemigraphis colorata* (Acanthaceae)," Phytochemistry, vol. 105, Jun. 20, 2014, pp. 141-146.
Halkes, K.M. et al., "A Facile Method for the Preparation of Gold Glyconanoparticles from Free Oligosaccharides and Their Applicability in Carbohydrate-Protein Interaction Studies," Eur. J. Org. Chem, vol. 2005, No. 17, Aug. 15, 2005, pp. 3650-3659.
Al-Jamal, K. T. et al., "An intrinsically fluorescent dendrimer as a nanoprobe of cell transport," Journal of Drug Targeting, vol. 14, No. 6, Jul. 2006, pp. 405-412.
Ariga, T. et al., "Characterization of Sulfated Glucuronic Acid Containing Glycolipids Reacting with IgM M-proteins in Patients with Neuropathy," Journal of Biological Chemistry 262(2), Jan. 1987, pp. 848-853.
Ariga, T., "Pathogenic role of ganglioside metabolism in neurodegenerative diseases," Journal of Neuroscience Research, vol. 92, Iss. 10, Oct. 2014, pp. 1227-1242.
Ariga, T., "The role of sulfoglucuronosyl glycosphingolipids in the pathogenesis of monoclonal IgM paraproteinemia and peripheral neuropathy," Proc Jpn Acad Ser B Phys Biol Sci, vol. 87, Jul. 2011, pp. 386-404.
Berentsen, S., "Role of Complement in Autoimmune Hemolytic Anemia," Transfus Med Hemother, vol. 42, No. 5, Sep. 2015, pp. 303-310.
Bohorov, O. et al., "Arraying glycomics: a novel bi-functional spacer for one-step microscale derivatization of free reducing glycans," Glycobiology, vol. 16, No. 12, Dec. 2006, pp. 21C-27C.
Bukowski, R. et al., "Synthesis and Conformational Analysis of the T-Antigen Disaccharide (β-D-Gal-(1→3)-α-D-GalNAc-OMe)," European Journal of Organic Chemistry, vol. 2001, Iss. 14, Jul. 2001, pp. 2697-2705.
Burger, D et al., "Identification of the glycosylated sequons of human myelin-associated glycoprotein," Biochem Biophys Res Commun, vol. 197, Iss. 2, Dec. 15, 1993, pp. 457-464.
Burger, D. et al., "Anti-myelin-associated glycoprotein antibodies in patients with a monoclonal IgM gammopathy and polyneuropathy, and a simplified method for the preparation of glycolipid antigens," J Immunol Methods, vol. 140, Iss. 1, Jun. 24, 1991, pp. 31-36.
Byrne, G. W. et al., "Evaluation of different alpha-Galactosyl glycoconjugates for use in xenotransplantation," Bioconjugate Chem., vol. 13, Iss. 3, Mar. 26, 2002, pp. 571-581.
Crew, V. K. et al., "New mutations in C1GALT1C1 in individuals with Tn positive phenotype," British Journal of Haematology, vol. 142, No. 4, Jun. 5, 2008, pp. 657-667.
Crocker, P.R. et al., "Siglecs and their roles in the immune system," Nat Rev Immunol, vol. 7, Apr. 2007, pp. 255-266.
Dalakas, M. C., "Pathogenesis and treatment of anti-MAG neuropathy," Curr Treat Options Neurol, vol. 12, Iss. 2, Mar. 2010, pp. 71-83.
Davis, B. G. "Recent developments in glycoconjugates," J. Chem. Soc., vol. 1, Jun. 14, 1999, pp. 3215-3237.
Delmont, E. et al., "Diagnostic Utility of Auto Antibodies in Inflammatory Nerve Disorders," Journal of Neuromuscular Diseases, vol. 2, Jun. 4, 2015, pp. 107-112.
Duthaler, R. O. et al., "In vivo neutralization of naturally existing antibodies against linear alpha(1,3)-galactosidic carbohydrate epitopes

(56) References Cited

OTHER PUBLICATIONS by multivalent antigen presentation: A solution for the first hurdle of pig-to-human xenotransplantation," Chimia, vol. 64, No. 1, Feb. 2010, pp. 23-28.
Ernst, B. et al., "From carbohydrate leads to glycomimetic drugs," Nature Reviews Drug Discovery, Jul. 24, 2009, pp. 661-677.
Esko, J. D. et al., "Microbial Lectins: Hemagglutinins, Adhesins, and Toxins," Essentials of Glycobiology, Chapter 34, 2nd edition, 2009, seven pages, [Online] [Retrieved on Jan. 10, 2020] Retrieved from the Internet <URL: https://www.ncbi.nlm.nih.gov/books/NBK1907/?report=reader>.
Fluri, F. et al., "Microheterogeneity of anti-myelinassociated glycoprotein antibodies," J Neurol Sci, vol. 207, Iss. 1-2, Mar. 2003, pp. 43-49.
Furuike, T. et al., "A Highly Practical Synthesis of Cyclodextrin-Based Glycoclusters Having Enhanced Affinity with Lectins," Tetrahedron, 2000, vol. 56, No. 51, pp. 9909-9915.
Furukawa, T. et al., "A potential glucuronate glycosyl donor with 2-O-acyl-6,3-lactone structure: efficient synthesis of glycosaminoglycan disaccharides," Tetrahedron Letters, vol. 52, Iss. 43, Oct. 26, 2011, pp. 5567-5570.
Gallego et al., "Epitope Diversity of N-Glycans from Bovine Peripheral Myelin Glycoprotein PO Revealed by Mass Spectrometry and Nano Probe Magic Angle Spinning .sup.1H NMR Spectroscopy," Journal of Biological Chemistry 276(33), Jun. 15, 2001, pp. 30334-30844.
Herrendorff et al., "Selective in vivo removal of pathogenic anti-MAG autoantibodies, an antigen-specific treatment option for anti-MAG neuropathy," Proceedings of the National Academy of Sciences USA 114(18), Mar. 2017, pp. E3689-E3698.
Herrendorff, R. et al., "Anti-myelin-associated glycoprotein neuropathy—a Carbohydrate Polymer Effectively Blocks Pathogenic Anti-MAG Antibodies," 13th International Congress on Neuromuscular Disease (ICNMD), Nice, France, Jul. 2014, Abstract, one page.
Holgersson, J. et al., "Characteristics of protein-carbohydrate interactions as a basis for developing novel carbohydrate-based antirejection therapies," Immunol Cell Biol, vol. 83, Oct. 21, 2005, pp. 694-708.
Ilyas, A. A. et al., "IgM in a human neuropathy related to paraproteinemia binds to a carbohydrate determinant in the myelin-associated glycoprotein and to a ganglioside," Proc Natl Acad Sci USA, vol. 81, Feb. 1984, pp. 1225-1229.
Ilyas, A. A et al., "Induction of experimental ataxic sensory neuronopathy in cats by immunization with purified SGPG," J Neuroimmunol., vol. 193, No. 1-2, Jan. 2008, pp. 87-93.
Kadlecova, Z. et al., "Comparative Study on the In Vitro Cytotoxicity of Linear, Dendritic, and Hyperbranched Polylysine Analogues," Biomacromolecules, vol. 13, No. 10, Aug. 29, 2012, pp. 3127-3137.
Karki, G. et al., "An expeditious synthesis of human blood-group antigens, ABO histo-blood group type II antigens and xenoantigen oligosaccharides with amino type spacer-arms," Glycoconjugate Journal, vol. 33, Feb. 2016, pp. 63-78.
Katopodis, A. G. et al., "Removal of anti-Galalpha1,3Gal xenoantibodies with an injectable polymer," J Clin Invest, vol. 110, No. 12, Dec. 2002, pp. 1869-1877.
Kelm, S. et al., "Sialoadhesin, myelin-associated glycoprotein and CD22 define a new family of sialic acid-dependent adhesion molecules of the immunoglobulin superfamily," Curr Biol, vol. 4, Iss. 11, Nov. 1994, pp. 965-972.
Knoppova, B. et al., "The Origin and Activities of igA1—Containing immune Complexes in igA Nephropathy," Frontiers in Immunology, vol. 7, Article 117, Apr. 2016, pp. 1-25.
Kollewe, K. et al., "Anti-Ganglioside Antibodies in Amyotrophic Lateral Sclerosis Revisited," Plos One, Apr. 14, 2015, pp. 1-11.
Kornilov, A. V. et al., "Synthesis of 3-O-sulfoglucuronyl lacto-N-neotetraose 2-aminoethyl glycoside and biotinylated neoglycoconjugates thereof," Carbohydr Res, vol. 329, Iss. 4, Dec. 2000, pp. 717-730.
Lunn, M. P. T. et al., "Immunotherapy for IgM anti-myelin-associated glycoprotein paraprotein-associated peripheral neuropathies," Cochrane Database Syst Rev, Oct. 2016, pp. 1-68.

Millen, S. H. et al., "Identification and Characterization of the Carbohydrate Ligands Recognized by Pertussis Toxin via a Glycan Microarray and Surface Plasmon Resonance," Biochemistry, vol. 49, No. 28, Jun. 1, 2010, pp. 5954-5967.
Munneke, S., et al., "The Rapid and Facile Synthesis of Oxyamine Linkers for the Preparation of Hydrolytically Stable Glycoconjugates," Organic Letters, 2015, vol. 17, No. 3, pp. 624-627.
Nifantiev, N. E. et al., "New schemes for the synthesis of glycolipid oligosaccharide chains," Pure Appl. Chem., vol. 76, Iss. 9, Sep. 30, 2004, pp. 1705-1714.
Nobile-Orazio, E., "Antigenic Determinants in IgM Paraprotein-Related Neuropathies," Clinical Lymphoma & Myeloma, vol. 9, Iss. 1, Mar. 1, 2009, 9, pp. 107-109.
Numata, M. et al., "Total synthesis of sialosylcerebroside, GM4," Carbohydrate Research, vol. 163, Iss. 2, Jun. 1987, pp. 209-225.
Oberg, C. T. et al., "Inhibition of Galectins with Small Molecules," Chimia, vol. 65, No. 1/2, Feb. 1, 2011, pp. 18-23.
Ogino, M. et al., "Affinity studies of human anti-MAG antibodies in neuropathy," J Neuroimmunol, vol. 52, Iss. 1, Jun. 1994, pp. 41-46.
Page, N. et al., "A monoclonal anti-idiotypic antibody against a human monoclonal IgM with specificity for myelin-associated glycoprotein," J Immunol, vol. 134, No. 5, May 1, 1985, pp. 3094-3099.
PCT International Search Report & Written Opinion, International Application No. PCT/EP2018/056583, dated Jun. 12, 2018, 14 Pages.
PCT International Search Report, PCT/EP2015/055140, dated May 4, 2015, four pages.
PCT Third Party Observations, International Application No. PCT/EP2018/056583, dated Jul. 12, 2019, 15 Pages.
Pukin, A.V., et al., "Strong Inhibition of Cholera Toxin by Multivalent GM1 Derivatives," ChemBioChem, 2007, vol. 8, No. 13, pp. 1500-1503.
Quarles, R. H., "Myelin-associated glycoprotein (MAG): Past, present and beyond," J Neurochem, vol. 100, Nov. 9, 2006, pp. 1431-1448.
Russian Federal Service for Intellectual Property, Official Action (Inquiry) of the Substantive Examination, RU Patent Application No. 2016134035/04, dated Oct. 24, 2018, 14 pages.
Sarkar et al., "Synthesis and glycosaminoglycan priming activity of three disaccharides related to the linkage region tetrasaccharide of proteoglycans," Carbohydrate Research 279, Aug. 1995, pp. 161-171.
Sato, S. et al., "cDNA cloning and amino acid sequence for human myelin associated glycoprotein," Biochem Biophys Res Commun, vol. 163, Iss. 3, Sep. 29, 1989, pp. 1473-1480.
Schmitz, B. et al., "Determination of structural elements of the L2/HNK-1 carbohydrate epitope required for its function", Glycoconjugate Journal, vol. 11, Iss. 4, Aug. 1994, pp. 345-352.
Schneller, M., et al., "An Effective Method for the Synthesis of Neoglycoproteins and Neogangliosideproteins by Use of Reductively Aminated Sulfhydryl-Containing Carbohydrate Conjugates," Biol. Chem. Hoppe-Seyler, 1992, vol. 373, No. 11, pp. 1095-1104.
Sheikh, K.A. et al., "An update on pathobiologic roles of anti-glycan antibodies in Guillain-Barré syndrome," Biology Reports, vol. 2, No. 21, Mar. 25, 2010, pp. 1-5.
Simon-Haldi et al., "Identification of a peptide mimic of the L2/HNK-1 carbohydrate epitope," Journal of Neurochemistry 83(6), Sep. 2002, pp. 1380-1388.
Spagnol, G. et al., "Molecular cloning of human myelin-associated glycoprotein,". J Neurosci Res, vol. 24, Oct. 1989, pp. 137-142.
Sukhova, E. V. et al., "Synthesis of oligosaccharides related to the HNK-1 antigen. 5. Synthesis of a sulfo-mimetic of the HNK-1 antigenic trisaccharide", Russian Chemical Bulletin, International Edition, vol. 56, No. 8, Aug. 2007, pp. 1655-1670.
Sun, B. et al., "Total synthesis of the aminopropyl functionalized ganglioside GM1," Science China Chemistry, vol. 55, Iss. 1, Jan. 2012, pp. 31-35.
Tatum, A. H., "Experimental paraprotein neuropathy, demyelination by passive transfer of human IgM anti-myelin-associated glycoprotein," Ann Neurol, vol. 33, May 1993, pp. 502-506.

(56) References Cited

OTHER PUBLICATIONS

Thoma, G. et al., "Versatile Functionalization of Polylysine: Synthesis, Characterization, and Use of Neoglycoconjugates," Journal of the American Chemical Society, vol. 121, No. 25, Jun. 1999, pp. 5919-5929.
Tokuda, A. et al., "On the specificity of anti-sulfoglucuronosyl glycolipid antibodies," J Carbohydr Chem, vol. 17, 1998, pp. 535-546.
Tsvetkov et al., "Synthesis and Molecular Recognition Studies of the HNK-1 Trisaccharide and Related Oligosaccharides. The Specificity of Monoclonal Anti-HNK-1 Antibodies as Assessed by Surface Plasmon Resonance and STD NMR," Journal of the American Chemical Society134(1), Nov. 16, 2011, pp. 426-435.
Ueda, A. et al., "Anti-GM1 antibodies affect the integrity of lipid rafts," Molecular and Cellular Neuroscience, vol. 45, Iss. 4, Dec. 2010, pp. 355-362.
Ueda, I. et al., "Synthesis and Pharmacological Properties of N-[3-{3-(1-Piperidinylmethyl)phenoxy}propyl]-2-(2-hydroxyethylthio)acetamide and Related Compounds as Antiulcer Agents.I," Chemical and Pharmaceutical Bulletin, vol. 38, No. 11, Nov. 1990, pp. 3035-3041.
Usuki, S. et al., "Development of a novel therapy for Lipo-oligosaccharide-induced experimental neuritis: Use of peptide glycomimics," J Neurochem, vol. 113, Apr. 2010, pp. 351-362.
Usuki, S. et al., "Novel anti-idiotype antibody therapy for lipooligosaccharide-induced experimental autoimmune neuritis: Use relevant to Guillain-Barré syndrome," J Neurosci Res, vol. 88, Iss. 8, Jun. 2010, pp. 1651-1663.
Voshol et al., "Structure of the HNK-1 Carbohydrate Epitope on Bovine Peripheral Myelin Glycoprotein P0," Journal of Biological Chemistry 271(38), Sep. 1996, pp. 22957-22960.
Willison, H. J. et al., "Glycolipid antigens and autoantibodies in autoimmune neuropathies," Trends in Immunology, vol. 34, Iss. 9, Sep. 2013, pp. 453-459.
Willison, H. J. et al., "Synthetic disialylgalactose immunoadsorbents deplete anti-GQ1b antibodies from autoimmune neuropathy sera," Brain, vol. 127, Iss. 3, Mar. 2004, pp. 680-691.
Wilson, J. W. et al., "Mechanisms of bacterial pathogenicity," Postgraduate Medical Journal, vol. 78, Apr. 1, 2002, pp. 216-224.
Yeh, C-Y. et al., "C-Terminal Repeats of Clostridium difficile Toxin A Induce Production of Chemokine and Adhesion Molecules in Endothelial Cells and Promote Migration of Leukocytes," Infection and Immunity, vol. 76, No. 3, Mar. 2008, pp. 1170-1178.
Zhang, Z. et al., "Programmable One-Pot Oligosaccharide Synthesis," Journal of the American Chemical Society, vol. 121, No. 4, Jan. 14, 1999, pp. 734-753.
Zsiska et al., "Influence of sulfate and carboxylate groups on the conformation of chondroitin sulfate related disaccharides," Carbohydrate Research 243, 1993, pp. 225-258.
Zsiska et al., "Synthesis of beta-D-GlcA-(1.fwdarw.3)-beta-D-Gal disaccharides with 4- and 6-sulfate groups and 4,6-disulfate groups," Carbohydrate Research 215(2), Feb. 1991, pp. 279-292.
Braun, P.E. et al., "Myelin-associated glycoprotein is the antigen for a monoclonal IgM in polyneuropathy," Journal of Neurochemistry, vol. 39, Iss. 5, Nov. 1982, pp. 1261-1265.
Das, S. et al., "Neutralization of cholera toxin with nanoparticle decoys for treatment of cholera," PLOS Neglected Tropical Diseases 12(2), Feb. 22, 2018, pp. 1-17.
Gabriel, J-M. et al., "Confocal microscopic localization of anti-myelin-associated glycoprotein autoantibodies in a patient with peripheral neuropathy initially lacking a detectable IgM gammopathy," Acta Neuropathologica, vol. 95, Apr. 1998, pp. 540-546.
Nagatsuka, T. et al., "Glycotechnology for Decontamination of Biological Agents: A Model Study Using Ricin and Biotin-Tagged Synthetic Glycopolymers," ACS Applied Materials & Interfaces, vol. 4, No. 2, Jan. 2, 2012, pp. 832-837.
Polizzotti, B.D. et al., "Effects of Polymer Structure on the Inhibition of Cholera Toxin by Linear Polypeptide-Based Glvcopolvmers," Biomacromolecules 7(2), Feb. 2006, pp. 483-490.
Richards, S. J, et al., "Probing bacterial-toxin inhibition with synthetic glycopolymers prepared by tandem post-polymerization modification: role of linker length and carbohydrate density," Angewandte, Chemie International Edition, vol. 51, Iss. 31, Jun. 19, 2012, pp. 7812-7816.
Steck, A.J. et al., "Anti-myelin-associated glycoprotein neuropathy," Current Opinion in Neurology, vol. 19, Iss. 5, Oct. 2006, nn. 458-463.
Steck, A.J. et al., "Demyeliating neuropathy and monoclonal IgM antibody to myelin-associated glycoprotein," Neurology, vol. 33, Iss. 1, Jan. 1, 1983, pp. 19-23.
Stevenson, L. et al., "Investigating the function of Fe-specific binding of IgM to Plasmodium falciparum erythrocyte membrane protein 1 mediating erythrocyte rosetting," Cellular Microbiology, vol. 17, Iss. 6, Jan. 28, 2015, pp. 819-831.
Thoma, G. et al., "Synthesis of Oligosaccharide-Polylysine Conjugates: A Well Characterized Sialyl Lewis Polymer for ELISA," J. Am. Chem. Soc., vol. 119, No. 31, Aug. 6, 1997, pp. 7414-7415.
United States Office Action, U.S. Appl. No. 15/760,398, dated Sep. 29, 2020, 17 pages.
Watanabe, M. et al., "Structural Analysis of the Interaction between Shiga Toxin B Subunits and Linear Polymers Bearing Clustered Globotriose Residues," Infection and Immunity, vol. 74, No. 3, Mar. 2006, pp. 1984-1988.
Zhou, D. et al., "Glycopolymer modification on physicochemical and biological properties of poly(L-lysine) for gene delivery," International Journal of Biological Macromolecules, vol. 50, Iss. 4, May 2012, pp. 965-973.
Huang, M.L. et al., ""Determination of receptor specificities for whole influenza viruses using multivalent glycan arrays,"" Chemical Communications, vol. 51, Dec. 31, 2014, pp. 5326-5329.

* cited by examiner

CARBOHYDRATE LIGANDS THAT BIND TO ANTIBODIES AGAINST GLYCOEPITOPES OF GLYCOSPHINGOLIPIDS

FIELD OF THE INVENTION

The invention relates to carbohydrate ligands and moieties, respectively, that bind to antibodies against glycoepitopes of glycosphingolipids of the nervous system, polymers comprising these carbohydrate ligands, and to their use in diagnosis and therapy of neurological diseases.

BACKGROUND OF THE INVENTION

Various neurological diseases are associated with the presence or increased levels of anti-glycan antibodies. Anti-glycolipid antibodies, particularly anti-ganglioside antibodies have been detected in a variety of neuropathological conditions, e.g. in multiple sclerosis, Parkinson's disease, Alzheimer's disease, dementia, Amyotrophic Lateral Sclerosis (ALS) autoimmune-mediated neuropathies including chronic inflammatory demyelinating polyneuropathy (CIDP), Guillain-Barré-syndrome (GBS) (with subtypes acute motor axonal neuropathy (AMAN), acute motor and sensory axonal neuropathy (AMSAN) and acute inflammatory demyelinating polyneuropathy (AIDP)), Miller Fisher syndrome (MFS) and multifocal motor neuropathy (MMN) (K. Kollewe et al., Plos One 2015, 10).

There is evidence from cell culture, tissue culture and animal models that anti-glycan antibodies are involved in immune-mediated attack towards the nervous system. The anti-glycan antibodies target relevant antigens on neuronal or myelin cells and can lead to disruption of nerve fiber function, conduction failure, axonal degeneration and demyelination (H. J. Willison and N. Yuki, Brain, 2002, 125, 2591-2625; K. A. Sheikh and G. Zhang, F1000 Biology Reports, 2010, 2, 21).

There are several mechanism that can explain the pathogenicity of the anti-glycan antibodies, including complement fixation and formation of membrane attack complex, disruption of signaling e.g. through sodium channel blockage (H. J. Willison and N. Yuki, Brain, 2002, loc. cit) or disruption of lipid rafts and interference with signaling pathways therein (A Ueda et al., Mol Cell Neurosci, 2010, 45(4), 355-62). Anti-ganglioside antibodies are also involved in dysfunction of the blood-brain barrier and thus contribute to progression of neurodegenerative diseases (T. Ariga, J Neurosci Res, 2014, 92, 1227-1242). Interestingly, some anti-glycan antibodies involved in immune-mediated neuropathy do not recognize single glycans but glycan clusters, particularly glycolipid complexes (pattern-recognition antibodies). Thus anti-glycolipid antibodies with pattern recognition characteristics have been described recently in immune-mediated neuropathy where previously no antibodies could be identified. Such antibodies have been identified in GBS, e.g. in the GBS subtype AIDP (H. J. Willison and C. S. Goodyear, Cell, 2013, 34, 453-459).

A pathogenic role for the anti-glycan antibodies is not always clear, even if it is established in immune-mediated neuropathies of acute and chronic types. In this group of diseases specific anti-glycolipid antibodies and specific clinical serological patterns are associated with particular clinical phenotypes (H. J. Willison and N. Yuki, Brain, 2002, 125, 2591-2625). The anti-glycan antibodies are usually of the IgM, IgG or IgA type.

The carbohydrate epitopes relevant to immune-mediated neuropathies are predominantly glycolipids, mostly of the ganglioside type involving GM1 (GM1a), GM1b, GalNAc-GM1b, Fucosyl-GM1, GM2, GM3, GD2, GD3, GD1a, GalNAc-GD1a, GD1b, GT1a, GT1b, GT1aα, GQ1b, GQ1bα, LM1, Hex-LM1, furthermore carbohydrate antigens of the group of non-sialylated glycolipids such as sulfatide or asialo-GM1/asialo-GM2, galactocerebroside, SGPG and SGLPG (HNK-1 epitope) (H. J. Willison and N. Yuki, Brain, 2002, 125, 2591-2625).

In the group of acute immune-mediated neuropathies, GBS encompasses several disease conditions that often involve autoantibodies against nerve glycoepitopes. The major subgroups among GBS are AMAN, AMSAN and AIDP, with AMAN predominantly affecting motor nerves compared to the other subtypes. GBS is associated with autoantibodies against gangliosides such as GM1, GD1a and structurally similar GM1b and GalNAc-GD1a, but also against ganglioside complexes, e.g. GM1 and GD1a. The pharyngeal-cervical-brachial (PCB) variant of GBS correlates with autoantibodies against GT1a alone or additionally GQ1b. Another clinically distinct subgroup of GBS is the Miller Fisher syndrome, which is mainly associated with antibodies against the GQ1b and the GT1a epitope. The pathogenic autoantibodies in the group of acute neuropathies are mostly of the IgG isotype (E. Delmont, H. J. Willison, J Neurom Dis., 2015, 2, 107-112).

In contrast to acute neuropathies the chronic immune-mediated neuropathies are mostly associated with IgM autoantibodies. Chronic inflammatory demyelinating polyneuropathy (CIDP) is the most common form of chronic demyelinating polyneuropathy. Subtypes of CIDP involve pathogenic anti-glycan antibodies (E. Delmont, H. J. Willison, J Neurom Dis., 2015, 2, 107-112).

The two other major disease groups among the chronic inflammatory neuropathies are the anti-MAG neuropathy and multifocal motor neuropathy (MMN). The anti-MAG neuropathy mainly involves autoantibodies against the HNK-1 epitope, present on multiple myelin antigens such as MAG, SGPG, SGLPG, P0 and PMP22. MMN patients often show autoantibodies against the ganglioside GM1 (or the complex GM1:GalC). Other, less frequent, chronic neuropathies encompass the chronic sensory axonal neuropathy with anti-sulfatide antibodies, the chronic motor neuropathy with GD1a or GD1b antibodies, and the CANOMAD (chronic ataxic neuropathy, opthalmoplegia, M-protein, Agglutination, Disialosyl antibodies) with antibodies against disialosyl gangliosides, such as GQ1b and GD1b (E. Nobile-Orazio, Clinical Lymphoma & Myeloma, 2009, 9, 107-109).

SUMMARY OF THE INVENTION

The invention relates to carbohydrate ligands and moieties, respectively, that bind to antibodies against glycoepitopes of glycosphingolipids of the nervous system, polymers comprising these carbohydrate ligands, and to their use in diagnosis and therapy of neurological diseases. In particular, the invention relates to carbohydrate ligands and moieties, respectively, mimicking glycoepitopes comprised by glycosphingolipids of the nervous system, particularly glycoepitopes comprised by glycosphingolipids of the cerebroside, the (neo)lacto-, the ganglio- and the sulfoglucuronyl paragloboside-type, which are bound by anti-glycan antibodies associated with neurological diseases. The invention relates to the use of these carbohydrate ligands and moieties respectively, in diagnosis as well as for the treatment of neurological diseases associated with anti-glycan antibodies.

In a first aspect, the present invention provides for a compound comprising a carbohydrate moiety and a linker Z, wherein said carbohydrate moiety mimics, or alternatively and preferably is, a glycoepitope comprised by a glycosphingolipid of the nervous system, wherein said linker Z is —N($R^a$)—A—B—CH$_2$—(CH$_2$)$_q$—SH, wherein $R^a$ is H, $C_1$-$C_4$-alkyl, $C_1$-$C_4$-alkoxy, CH$_2$C$_6$H$_5$, CH$_2$CH$_2$C$_6$H$_5$, OCH$_2$C$_6$H$_5$, or OCH$_2$CH$_2$C$_6$H$_5$; A is $C_1$-$C_7$-alkylene, $C_1$-$C_7$-alkoxy, $C_1$-$C_4$-alkyl—(OCH$_2$CH$_2$)$_p$O—$C_1$-$C_4$-alkyl, or $C_1$-$C_7$-alkoxy-$R^b$, wherein $R^b$ is an optionally substituted aryl or an optionally substituted heteroaryl, and wherein p is 0 to 6, preferably p is 1, 2 or 3, and further preferably p is 1; B is NHC(O), S or CH$_2$; q is 0 to 6, preferably q is 1, 2, 3 or 4, and further preferably q is 1 or 2; and wherein said linker Z is covalently bound via its —N($R^a$)-group to the reducing end of said carbohydrate moiety.

In a second aspect, the present invention provides for a compound of formula (I) or of formula (II), wherein formula (I) is

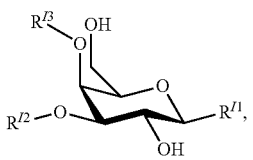
(I)

wherein $R^{J1}$ is Z or

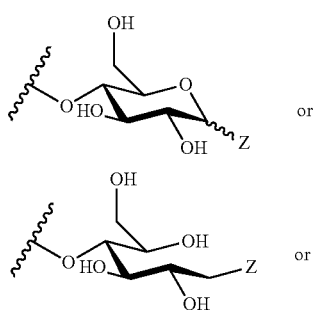

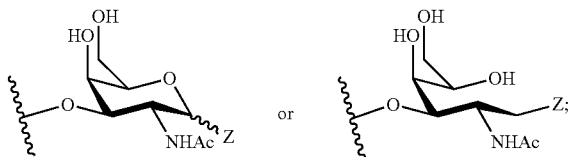

wherein $R^{J2}$ is H, SO$_3$H, or

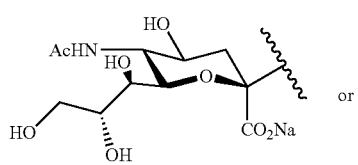

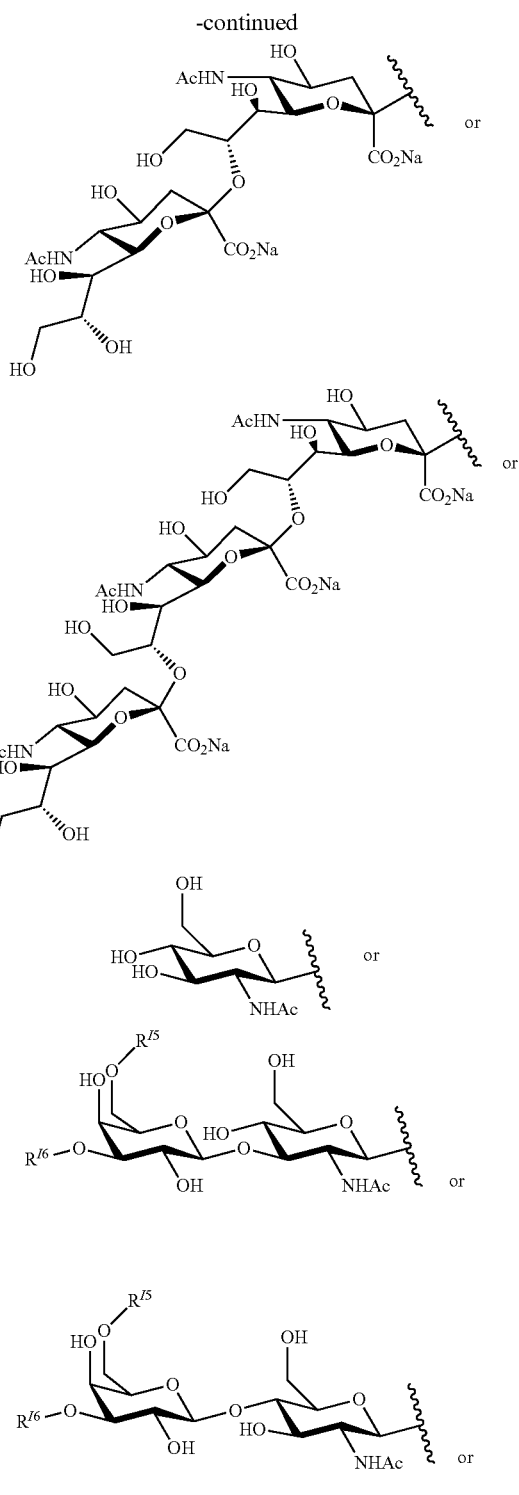

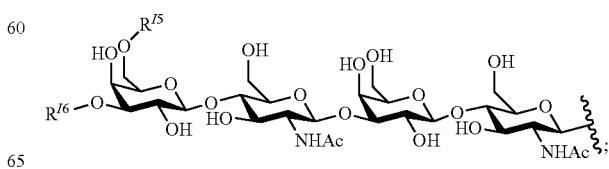

wherein $R^{I3}$ is H or

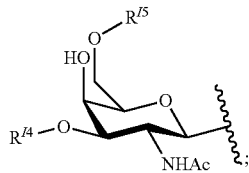

wherein $R^{I4}$ is H or

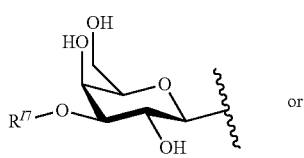

or

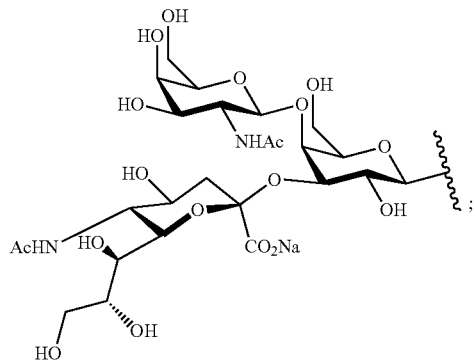

wherein $R^{I5}$ and $R^{I6}$ are independently H or

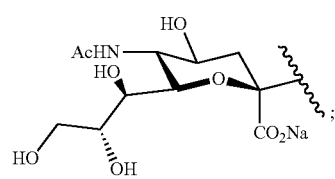

wherein $R^{I7}$ is H or

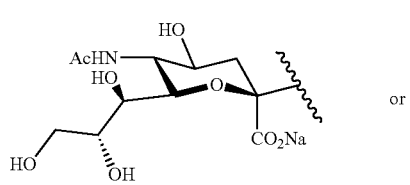

or

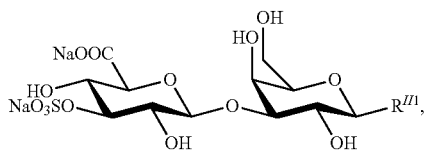

and wherein formula (II) is $$\text{(II)}$$

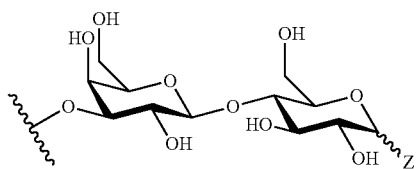

wherein $R^{II1}$ is Z or

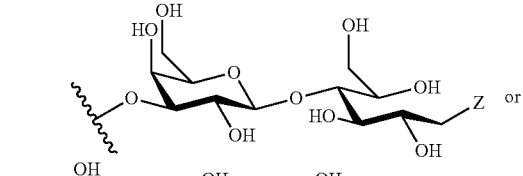

wherein $R^{II2}$ is Z or

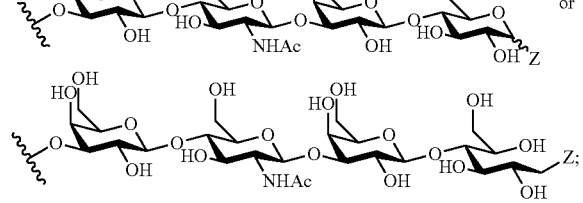

wherein said linker Z is —N($R^a$)—A—B—CH$_2$—(CH$_2$)$_q$—SH, wherein $R^a$ is H, $C_1$-$C_4$-alkyl, $C_1$-$C_4$-alkoxy, CH$_2$C$_6$H$_5$, CH$_2$CH$_2$C$_6$H$_5$, OCH$_2$C$_6$H$_5$, or OCH$_2$CH$_2$C$_6$H$_5$; A is $C_1$-$C_1$-$C_7$-alkylene, $C_1$-$C_7$-alkoxy, $C_1$-$C_4$-alkyl—(OCH$_2$CH$_2$)$_p$O—$C_1$-$C_4$-alkyl, or $C_1$-$C_7$-alkoxy-$R^b$, wherein $R^b$ is an optionally substituted aryl or an optionally substituted heteroaryl, and wherein p is 0 to 6, preferably p is 1, 2 or 3, and further preferably p is 1; B is NHC(O), S or $CH_2$; q is 0 to 6, preferably q is 1, 2, 3 or 4, and further preferably q is 1 or 2; and wherein said linker Z is covalently bound via its —N($R^a$)-group to the reducing end of said carbohydrate moiety.

Furthermore, the invention relates to therapeutically acceptable polymers comprising a multitude of substituents derived from the inventive compounds, wherein said compounds are connected to the polymer backbone by way of the linker Z, and wherein the connection is effected via the SH-moiety of linker Z.

Thus, in another aspect, the present invention provides for a polymer comprising a multitude of the inventive compounds, wherein said compounds are connected to the polymer backbone by way of said linker Z, and wherein said connection is effected via the SH—group of said linker Z.

In a further aspect, the present invention provides for a polymer comprising (i) a multitude of compounds of formula (I), (ii) a multitude of compounds of formula (II) or (iii) a multitude of compounds of formula (I) and of formula (II), wherein said compounds are connected to the polymer backbone by way of said linker Z, and wherein said connection is effected via the SH—group of said linker Z. Preferably said multitude of compounds of formula (I) and/or of formula (II) are either identical compounds of formula (I) and/or of formula (II) or different compounds selected from of formula (I) and/or of formula (II).

The invention relates also to pharmaceutical compositions comprising these compounds, diagnostic kits containing these, and to the use of these compounds for the diagnosis and therapy of neurological diseases associated with anti-glycan antibodies.

Thus, in another aspect, the present invention provides for a pharmaceutical composition comprising said inventive compound, preferably said inventive compound of formula (I) or of formula (II), or comprising said inventive.

In another aspect, the present invention provides for said inventive compound, preferably said inventive compound of formula (I) or formula (II), or said inventive polymer, or said inventive pharmaceutical composition for use in a method of treating a neurological disease, wherein preferably said neurological disease is selected from multiple sclerosis, Parkinson's disease, Alzheimer's disease, dementia, and an immune-mediated neuropathy, wherein preferably said immune-mediated neuropathy is selected from Guillain-Barré syndrome (GBS), chronic inflammatory demyelinating polyneuropathy (CIDP), Miller-Fischer syndrome, Bickerstaff brainstem encephalitis, multifocal motor neuropathy or anti-MAG neuropathy, wherein further preferably said immune-mediated neuropathy is selected from Guillain-Barré syndrome (GBS), chronic inflammatory demyelinating polyneuropathy (CIDP), Miller-Fischer syndrome, Bickerstaff brainstem encephalitis or multifocal motor neuropathy.

In another aspect, the present invention provides for said inventive compound, preferably said inventive compound of formula (I) or formula (II), or said inventive polymer, or said inventive pharmaceutical composition for use in a method of diagnosis of a neurological disease, wherein preferably said neurological disease is an immune-mediated neuropathy.

In another aspect, the present invention provides for a diagnostic kit comprising said inventive compound, preferably said inventive compound of formula (I) or formula (II), or said inventive polymer.

In another aspect, the present invention provides for an use of said inventive compound, preferably said inventive compound of formula (I) or formula (II), or said inventive polymer for the diagnosis of a neurological disease, wherein preferably said neurological disease is an immune-mediated neuropathy.

In another aspect, the present invention provides for an use of said inventive compound, preferably said inventive compound of formula (I) or formula (II), or said inventive polymer, for the manufacture of a medicament for the treatment of a neurological disease, wherein preferably said neurological disease is selected from multiple sclerosis, Parkinson's disease, Alzheimer's disease, dementia, and an immune-mediated neuropathy, wherein preferably said immune-mediated neuropathy is selected from Guillain-Barré syndrome (GBS), chronic inflammatory demyelinating polyneuropathy (CIDP), Miller-Fischer syndrome, Bickerstaff brainstem encephalitis, multifocal motor neuropathy or anti-MAG neuropathy, wherein further preferably said immune-mediated neuropathy is selected from Guillain-Barré syndrome (GBS), chronic inflammatory demyelinating polyneuropathy (CIDP), Miller-Fischer syndrome, Bickerstaff brainstem encephalitis or multifocal motor neuropathy.

In another aspect, the present invention provides for a method of treatment of a neurological disease, wherein preferably said neurological disease is an immune-mediated neuropathy, wherein said method comprises administering said inventive compound, preferably said inventive compound of formula (I) or formula (II), or said inventive polymer in a quantity effective against said disease, to a warm-blooded animal, preferably to a human, requiring such treatment.

BRIEF DESCRIPTION OF THE FIGURES

FIG. 2: Binding curves for compounds 6, 26, 34 and 86

DETAILED DESCRIPTION OF THE INVENTION

Figure 1:
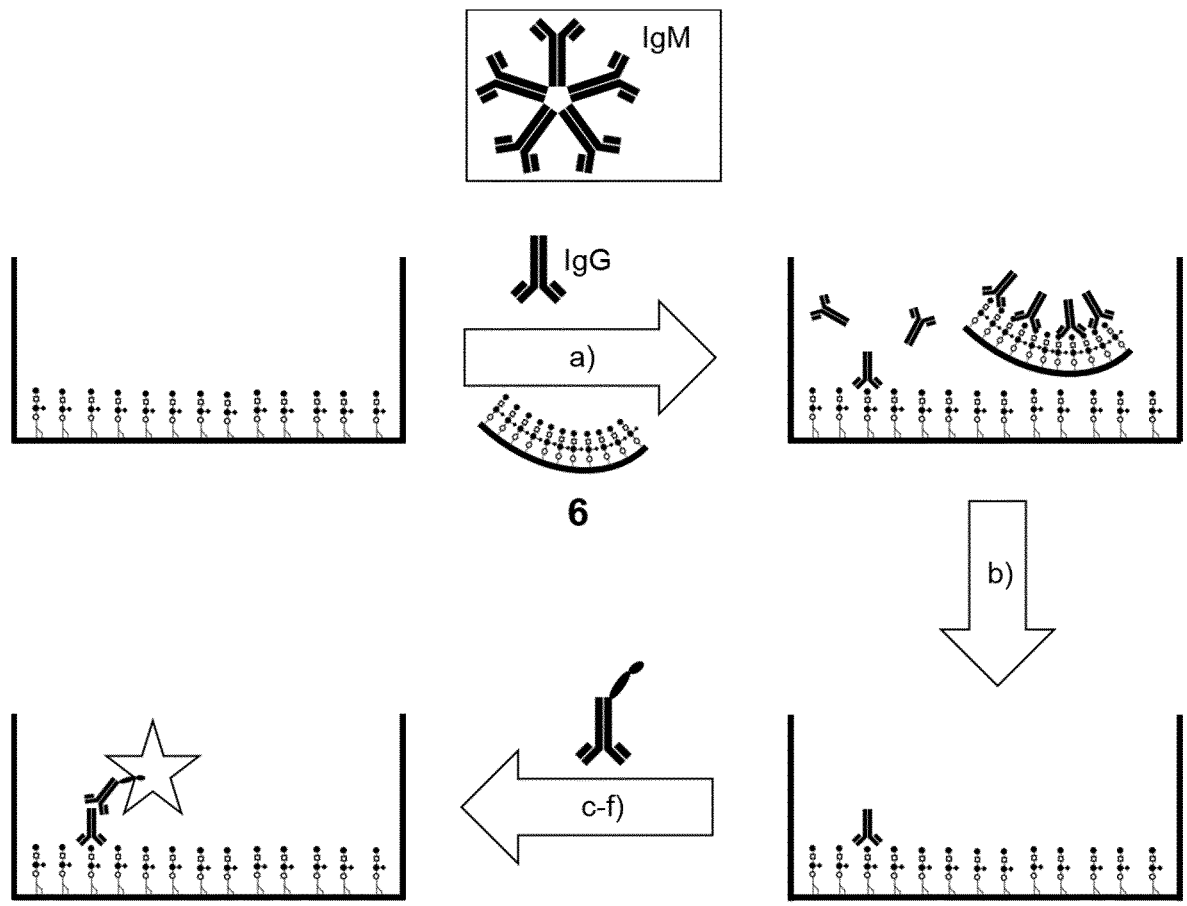
FIG. 1: Schematic representation of a competitive binding assay (a) Co-incubation of glycolipid-coated plates with neuropathy patient sera, containing anti-glycolipid antibodies of the IgG (and/or IgM) isotype, and glycopolymers. In this particular representative example GM1a ganglioside-coated plates are co-incubated with anti-GMa IgG-containing serum and glycopolymer 6. (b) Wash step. (c) Incubation with anti-human IgG (or IgM) antibody coupled to horseradish peroxidase. (d) Wash step. (e) Addition of tetramethylbenzidin (TMB) substrate. (f) Addition of acidic stop solution and measurement of the optical density.

The compounds of the present invention, and in particular the compounds of the present invention of formula (I) or (II), recognize anti-glycan antibodies against glycosphingolipid glycoepitopes of the nervous system, in particular glycoepitopes comprised by glycosphingolipids such as the cerebroside-, (neo)lacto-, and the ganglio-types. The carbohydrate ligands contain linkers that allow coupling to a polymer backbone for multivalent presentation. The glycopolymers resulting from the coupling are superior in the sequestration of anti-carbohydrate antibodies compared to the respective glycan-monomers. The glycopolymers are suitable diagnostic or therapeutic agents to detect and to bind anti-glycan antibodies in particular associated with neurological diseases.

The present invention provides for a compound comprising a carbohydrate moiety and a linker Z, wherein said carbohydrate moiety mimics, or alternatively and preferably is, a glycoepitope comprised by a glycosphingolipid of the nervous system, wherein said linker Z is —N(R$_a$)—A—B—CH$_2$—(CH$_2$)$_q$—SH, wherein R$^a$ is H, C$_1$-C$_4$-alkyl, C$_1$-C$_4$-alkoxy, CH$_2$C$_6$H$_5$, CH$_2$CH$_2$C$_6$H$_5$, OCH$_2$C$_6$H$_5$, or OCH$_2$CH$_2$C$_6$H$_5$; A is C$_1$-C$_7$-alkylene, C$_1$-C$_7$-alkoxy, C$_1$-C$_4$-alkyl—(OCH$_2$CH$_2$)$_p$O—C$_1$-C$_4$-alkyl, or C$_1$-C$_7$-alkoxy-R$^b$, wherein R$^b$ is an optionally substituted aryl or an optionally substituted heteroaryl, and wherein p is 0 to 6, preferably p is 1, 2 or 3, and further preferably p is 1; B is NHC(O), S or CH$_2$; q is 0 to 6, preferably q is 1, 2, 3 or 4, and further preferably q is 1 or 2; and wherein said linker Z is covalently bound via its —N(R$^a$)-group to the reducing end of said carbohydrate moiety.

In a preferred embodiment, said glycosphingolipid of the nervous system is selected from the cerebroside-, (neo) lacto-, ganglio-, or sulfoglucuronyl paragloboside-type. In a further preferred embodiment, said glycosphingolipid of the nervous system is a glycoside, wherein preferably said ganglioside is selected from GM1 (GM1a), GM1b, GalNAc-GM1b, Fucosyl-GM1, GM2, GM3, GD2, GD3, GD1a, GalNAc-GD1a, GD1b, GT1a, GT1b, GT1aα, GQ1b, GQ1bα, LM1 or Hex-LM1.

In particular, the present invention provides for a compound of formula (I) or of formula (II), wherein formula (I) is (I)

wherein R$^{J1}$ is Z or wherein R$^{J2}$ is H, SO$_3$H, or

-continued
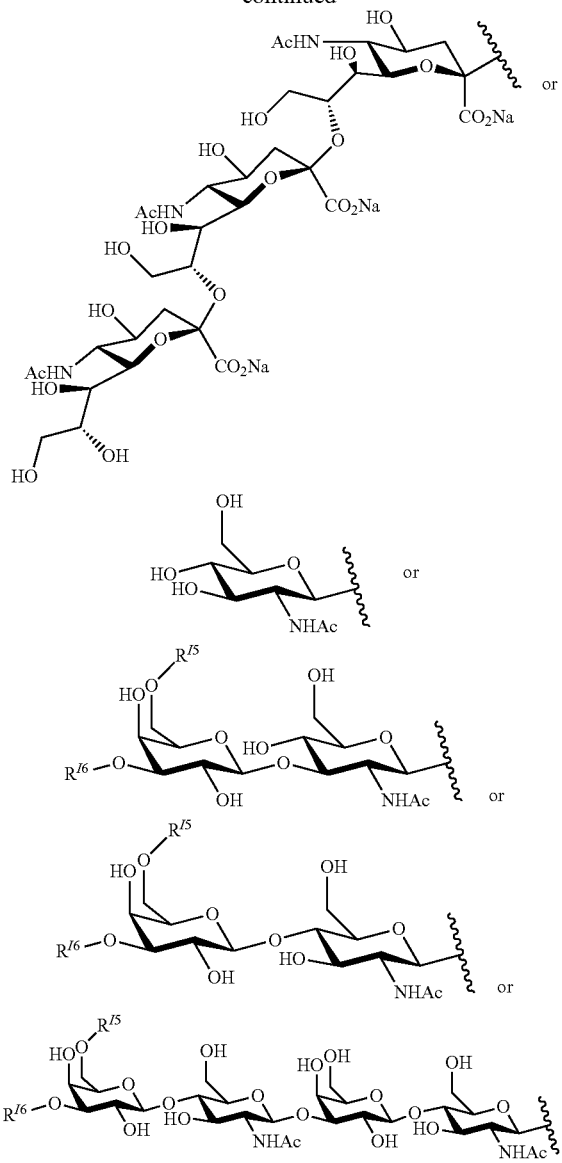
or
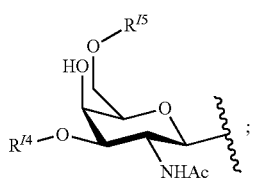
wherein $R^{I3}$ is H or
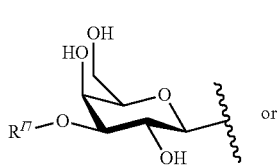
wherein $R^{I4}$ is H or
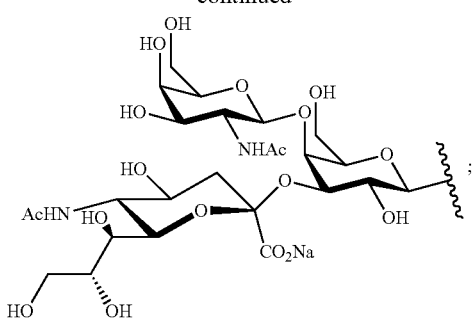
wherein $R^{I5}$ and $R^{I6}$ are independently H or
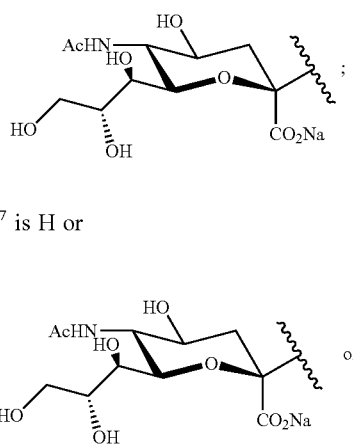
wherein $R^{I7}$ is H or
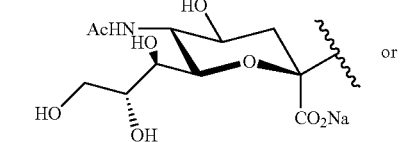
or
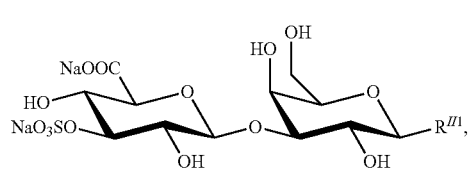
;
and wherein formula (II) is
$$\text{(II)}$$

wherein $R^{II1}$ is Z or

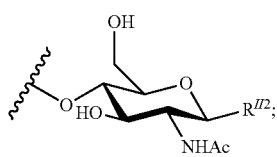

wherein $R^{II2}$ is Z or

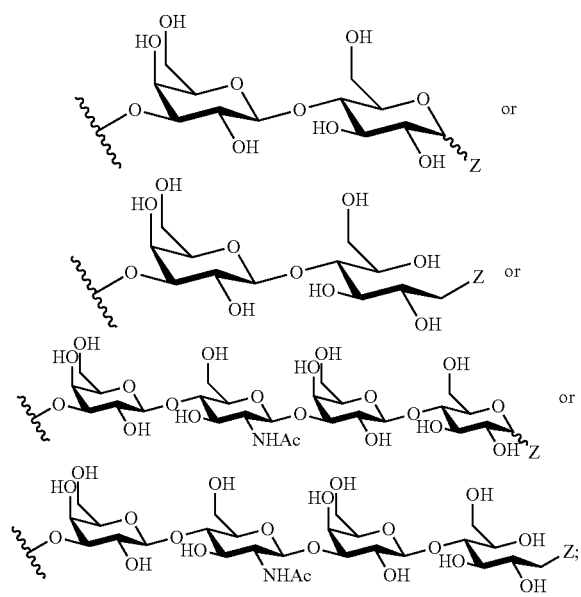

wherein said linker Z is —N($R^a$)—A—B—CH$_2$—(CH$_2$)$_q$—SH, wherein $R^a$ is H, C$_1$-C$_4$-alkoxy, CH$_2$C$_6$H$_5$, CH$_2$CH$_2$C$_6$H$_5$, OCH$_2$C$_6$H$_5$, or OCH$_2$CH$_2$C$_6$H$_5$; A is C$_1$-C$_7$-alkylene, C$_1$-C$_7$-alkoxy, C$_1$-C$_4$-alkyl—(OCH$_2$CH$_2$)$_p$O—C$_1$-C$_4$-alkyl, or C$_1$-C$_7$-alkoxy-$R^b$, wherein $R^b$ is an optionally substituted aryl or an optionally substituted heteroaryl, and wherein p is 0 to 6, preferably p is 1, 2 or 3, and further preferably p is 1; B is NHC(O), S or CH$_2$; q is 0 to 6, preferably q is 1, 2, 3 or 4, and further preferably q is 1 or 2; and wherein said linker Z is covalently bound via its —N($R^a$)-group to the reducing end of said carbohydrate moiety.

In a further preferred embodiment, said compound is a compound of formula (I).

The scope of the present invention comprises carbohydrate moieties mimicking glycoepitopes comprised by glycosphingolipid of the nervous system. Preferred compounds mimicking glycoepitopes comprised by glycosphingolipid of the nervous system in accordance with the present invention are compounds of the formula (I) as defined herein, wherein at least one of sialic acid moiety is replaced by a replacement moiety as shown and defined in formula (Ia) or formula (Ib)

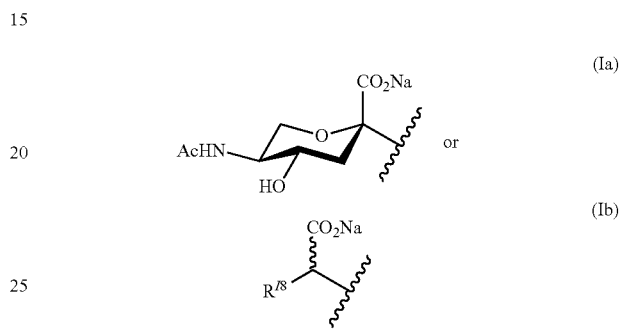

wherein for said replacement moiety of formula (Ib), $R^{78}$ is H, C$_1$-C$_8$-alkyl, C$_1$-C$_8$-alkyl-cycloalkyl, C$_1$-C$_8$-alkenyl, C$_1$-C$_8$-alkynyl, aryl, substituted aryl, wherein preferably said substitution of said aryl is by halogen, C$_1$-C$_8$-alkoxy, C$_1$-C$_8$-alkyl; heteroaryl, substituted heteroaryl, wherein preferably said substitution of said hetereoaryl is by halogen, C$_1$-C$_8$-alkoxy, C$_1$-C$_8$-alkyl; arylalkyl, substituted arylalkyl, wherein preferably said substitution of said arylalkyl is by halogen, C$_1$-C$_8$-alkoxy, C$_1$-C$_8$-alkyl; heteroarylalkyl, substituted heteroarylalkyl, wherein preferably said substitution of said heteroarylalkyl is by halogen, C$_1$-C$_8$-alkoxy, C$_1$-C$_8$-alkyl; cycloalkyl, cycloalkyl-C$_1$-C$_8$-alkyl, t-butyl, adamantyl, triazolyl all of which independently substituted with C$_1$-C$_8$ alkyl, aryl, heteroaryl, halogen.

In another preferred embodiment, said compound is a compound of formula (II).

In another preferred embodiment, said compound is a compound of formula 4*, 9*, 13*, 17*, 21*, 25*, 29*, 33*, or 46*-60* as depicted below.

4*

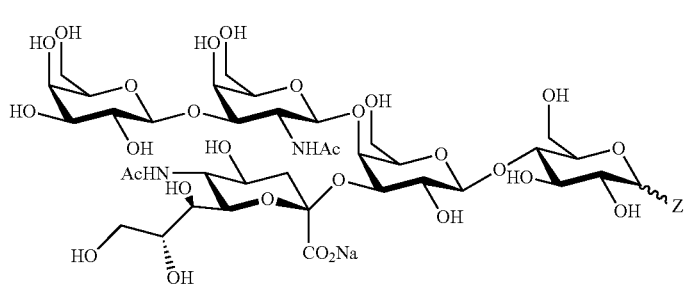

-continued
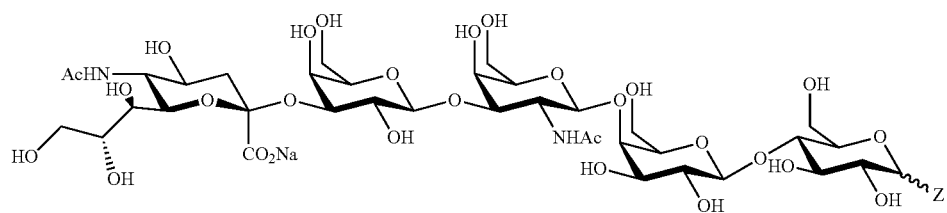
9*
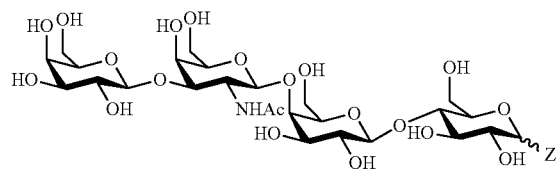
13*
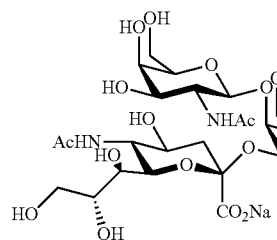
17*
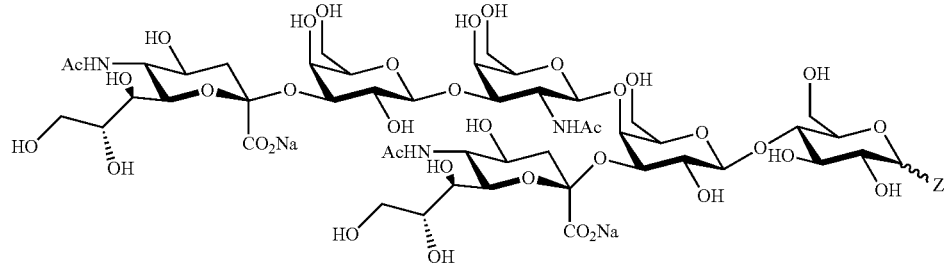
21*
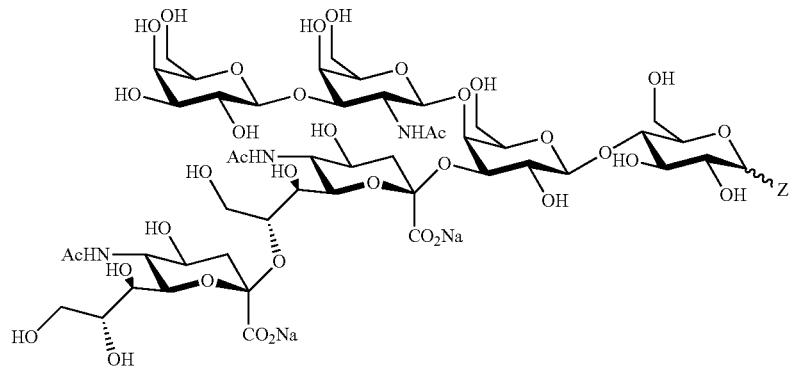
25*
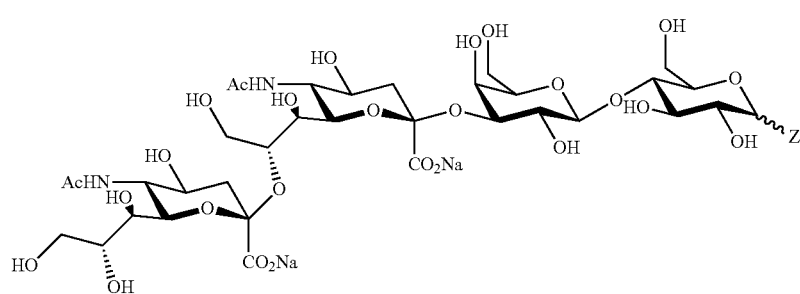
29*

-continued
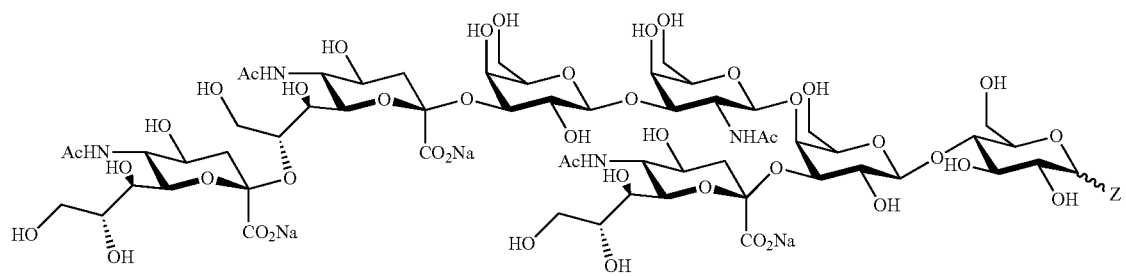
33*
46*  47*
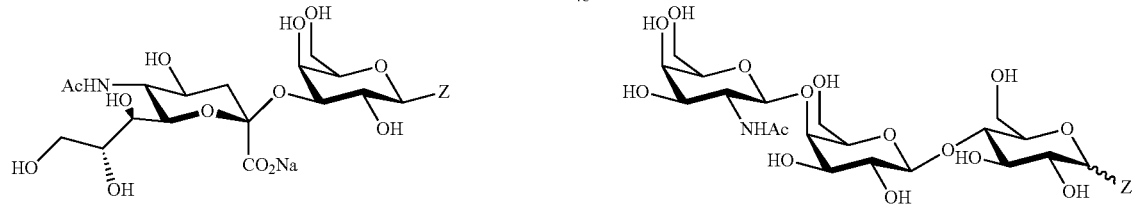
48*  49*
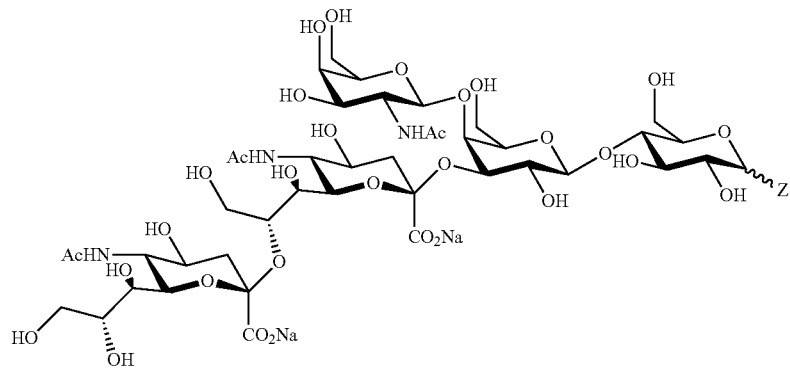
50*
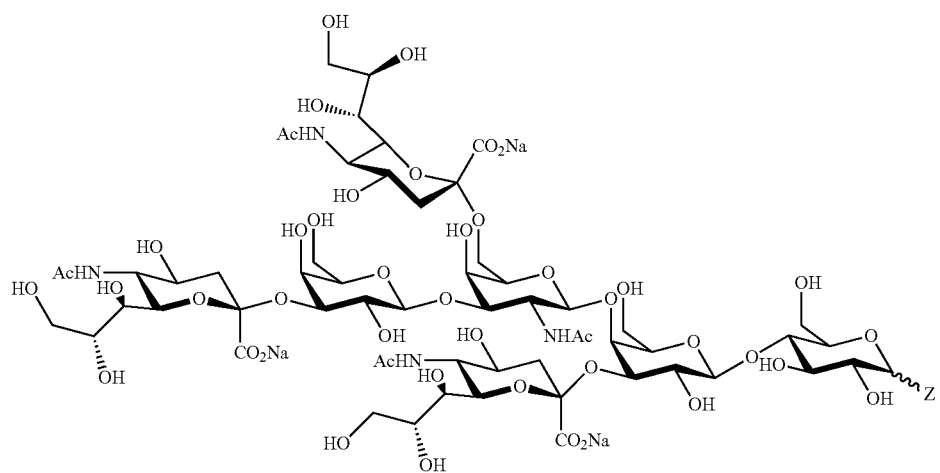
51*

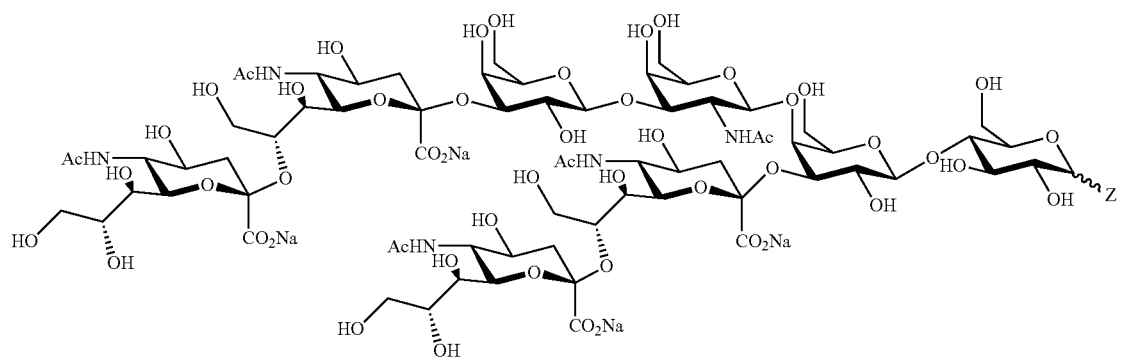
52*
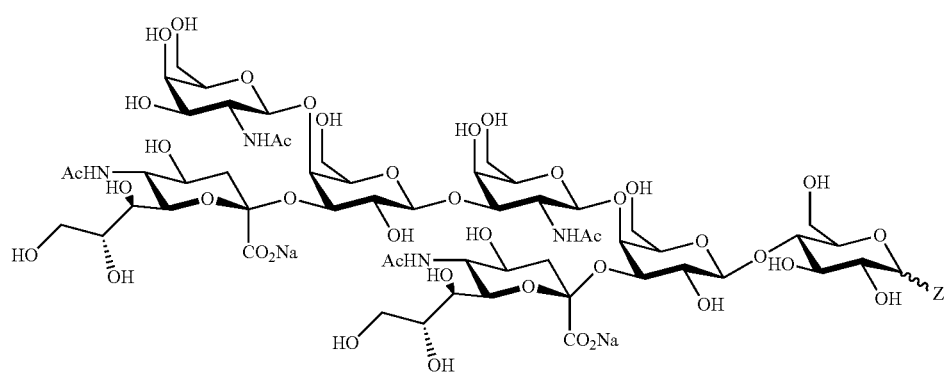
53*
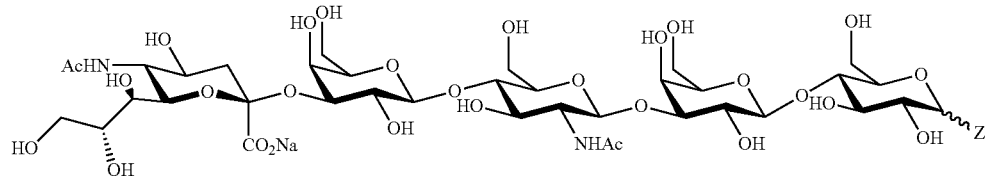
54*
55*
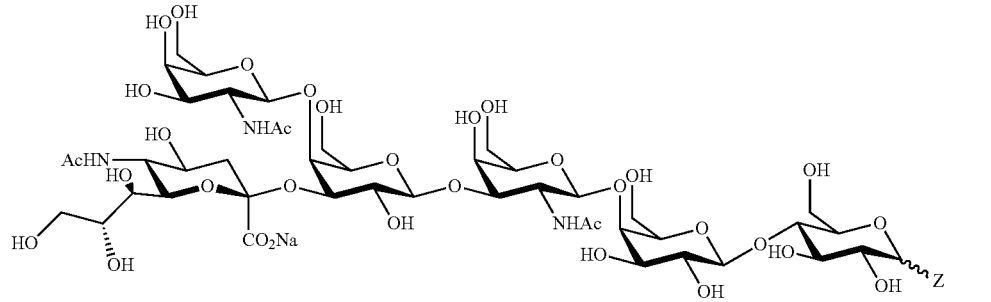
56*
57*
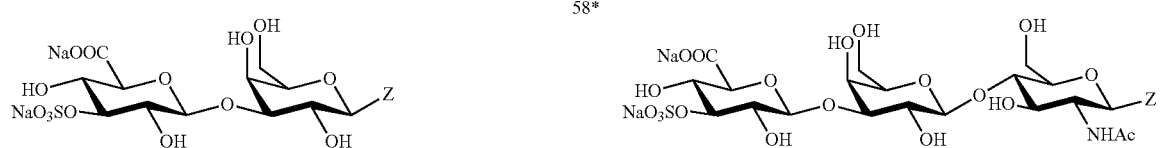
58* 59*

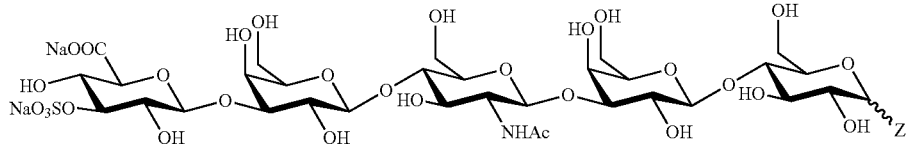

60* wherein said linker Z is —N(R$^a$)—A—B—CH$_2$—(CH$_2$)$_q$—SH, wherein R$^a$ is H, C$_1$-C$_4$-alkyl, C$_1$-C$_4$-alkoxy, CH$_2$C$_6$H$_5$, CH$_2$CH$_2$C$_6$H$_5$, OCH$_2$C$_6$H$_5$, or OCH$_2$CH$_2$C$_6$H$_5$; A is C$_1$-C$_7$-alkylene, C$_1$-C$_7$-alkoxy, C$_1$-C$_4$-alkyl—(OCH$_2$CH$_2$)$_p$O—C$_1$-C$_4$-alkyl, or C$_1$-C$_7$-alkoxy-R$^b$, wherein R$^b$ is an optionally substituted aryl or an optionally substituted heteroaryl, and wherein p is 0 to 6, preferably p is 1, 2 or 3, and further preferably p is 1; B is NHC(O), S or CH$_2$; q is 0 to 6, preferably q is 1, 2, 3 or 4, and further preferably q is 1 or 2; and wherein said linker Z is covalently bound via its —N(R$^a$)-group to the reducing end of said carbohydrate moiety.

In a further very preferred embodiment, said compound is a compound of formula 4*, 9*, 13*, 17*, 21*, 25*, 29*, 33*, or 46*-60*, wherein at least one of sialic acid moiety is replaced by a replacement moiety as shown and defined in formula (Ia) or formula (Ib)

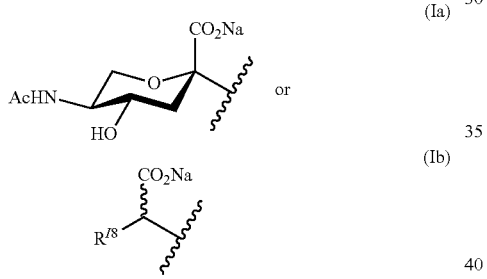

wherein for said replacement moiety of formula (Ib), R$^{r8}$ is H, C$_1$-C$_8$-alkyl, C$_1$-C$_8$-alkyl-cycloalkyl, C$_1$-C$_8$-alkenyl, C$_1$-C$_8$-alkynyl, aryl, substituted aryl, wherein preferably said substitution of said aryl is by halogen, C$_1$-C$_8$-alkoxy, C$_1$-C$_8$-alkyl; heteroaryl, substituted heteroaryl, wherein preferably said substitution of said hetereoaryl is by halogen, C$_1$-C$_8$-alkoxy, C$_1$-C$_8$-alkyl; arylalkyl, substituted arylalkyl, wherein preferably said substitution of said arylalkyl is by halogen, C$_1$-C$_8$-alkoxy, C$_1$-C$_8$-alkyl; heteroarylalkyl, substituted heteroarylalkyl, wherein preferably said substitution of said heteroarylalkyl is by halogen, C$_1$-C$_8$-alkoxy, C$_1$-C$_8$-alkyl; cycloalkyl, cycloalkyl-C$_1$-C$_8$-alkyl, t-butyl, adamantyl, triazolyl all of which independently substituted with C$_1$-C$_8$ alkyl, aryl, heteroaryl, halogen.

Preferred embodiments of said linker Z are as follows. Thus, in one embodiment, R$^a$ is H, CH$_3$, CH$_2$CH$_3$, CH$_2$CH$_2$CH$_3$, CH(CH$_3$)$_2$, OCH$_3$, OCH$_2$CH$_3$, OCH$_2$CH$_2$CH$_3$, CH$_2$C$_6$H$_5$, OCH$_2$C$_6$H$_5$; A is O(CH$_2$)$_p$CH$_2$, (CH$_2$)$_p$CH$_2$, CH$_2$(OCH$_2$CH$_2$)$_p$OCH$_2$, (OCH$_2$CH$_2$)$_p$OCH$_2$CH$_2$ or O(CH$_2$)$_p$C$_6$H$_5$; and B is NHC(O), S or CH$_2$. In a preferred embodiment, R$^a$ is CH$_3$ or OCH$_3$; A is O(CH$_2$)$_p$CH$_2$, (CH$_2$)$_p$CH$_2$, CH$_2$(OCH$_2$CH$_2$)$_p$OCH$_2$, (OCH$_2$CH$_2$)$_p$OCH$_2$CH$_2$ or O(CH$_2$)$_p$C$_6$H$_5$; and B is NHC(O) or S. Preferably, when B is S, and A is (CH$_2$)$_p$CH$_2$, then q is 1 to 5, preferably 1, 2 or 3.

In a further preferred embodiment, R$^a$ is CH$_3$ or OCH$_3$; A is O(CH$_2$)$_p$CH$_2$, (CH$_2$)$_p$CH$_2$, CH$_2$(OCH$_2$CH$_2$)$_p$OCH$_2$, (OCH$_2$CH$_2$)$_p$OCH$_2$CH$_2$ or O(CH$_2$)$_p$C$_6$H$_5$; and B is NHC(O).

In a further preferred embodiment, R$^a$ is C$_3$; A is O(CH$_2$)$_p$CH$_2$, (CH$_2$)$_p$CH$_2$, CH$_2$(OCH$_2$CH$_2$)$_p$OCH$_2$, (OCH$_2$CH$_2$)$_p$OCH$_2$CH$_2$ or O(CH$_2$)$_p$C$_6$H$_5$; and B is NHC(O) or S. Preferably, when B is S and A is (CH$_2$)$_p$CH$_2$, then q is 1 to 5, preferably 1, 2 or 3.

In a further preferred embodiment, R$^a$ is CH$_3$ or OCH$_3$; A is O(CH$_2$)$_p$CH$_2$, (CH$_2$)$_p$CH$_2$, CH$_2$(OCH$_2$CH$_2$)$_p$OCH$_2$, (OCH$_2$CH$_2$)$_p$OCH$_2$CH$_2$ or O(CH$_2$)$_p$C$_6$H$_5$; B is NHC(O) or S; and q is 1 to 5, preferably 1, 2 or 3, preferably 2.

In a further preferred embodiment, said linker Z is of a formula selected from any one of the formula (a) to (g):

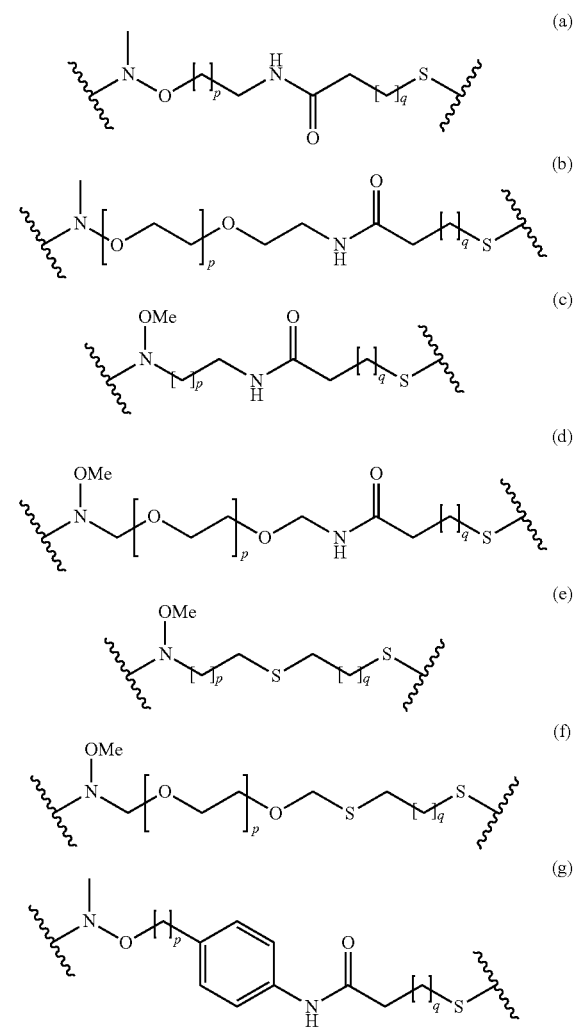

wherein p is between 0 and 6, preferably 1 to 3, in particular 1, and q is between 0 and 6, preferably between 1 and 4, in particular 1 or 2. In one embodiment, when said linker Z is of formula (e), then p and q are independently 1 to 6, preferably 1, 2 or 3; wherein, when p is 2, then q is 1 to 6, preferably 1 or 3 to 6, and when q is 2, then p is 3 to 6. In another embodiment, when said linker Z is of formula (e), then p and q are not both 2.

In said further preferred embodiment, and in light of the general formula of the present invention said linker Z is of a formula selected from any one of the formula (a) to (g):

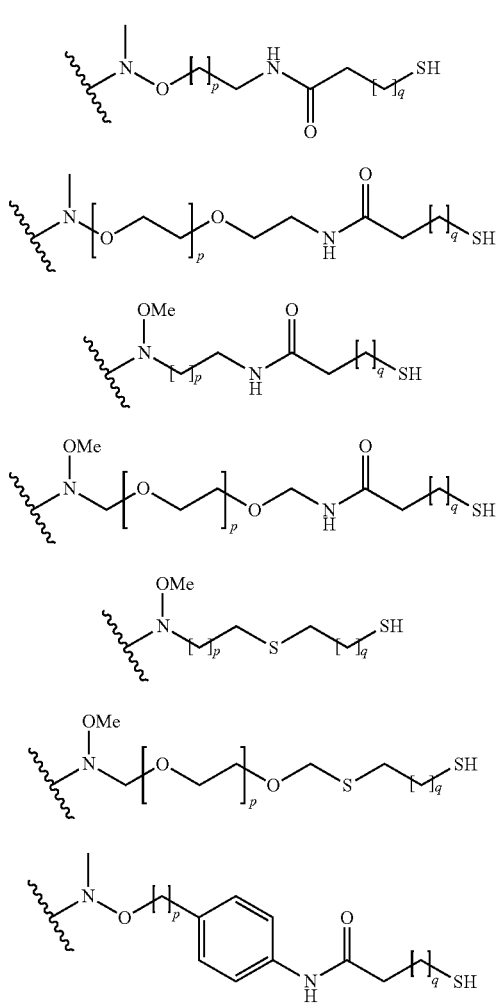

wherein p is between 0 and 6, preferably 1 to 3, in particular 1, and q is between 0 and 6, preferably between 1 and 4, in particular 2 In one embodiment, when said linker Z is of formula (e), then p and q are independently 1 to 6, preferably 1, 2 or 3; wherein, when p is 2, then q is 1 to 6, preferably 1 or 3 to 6, and when q is 2, then p is 3 to 6. In another embodiment, when said linker Z is of formula (e), then p and q are not both 2.

In a very preferred embodiment, said linker Z is —N(CH$_3$)—O(CH$_2$)$_2$—NHC(O)—(CH$_2$)$_3$—SH.

In a further preferred embodiment, said carbohydrate moiety mimicking, or alternatively and preferably being, a glycoepitope comprised by a glycosphingolipid of the nervous system is a carbohydrate moiety comprised by a compound of formula (I), and said glycoepitope is a glycoepitope of the cerebroside-, (neo)lacto-, or ganglio-type, further preferably of a ganglioside.

In a further preferred embodiment, said carbohydrate moiety mimicking, or alternatively and preferably being, a glycoepitope comprised by a glycosphingolipid of the nervous system is a carbohydrate moiety comprised by a compound of formula (II), and said glycoepitope is a glycoepitope of a sulfoglucuronyl paragloboside and hereby in particular a glycoepitope such as the antigenic HNK-1 carbohydrate epitope.

In a further very preferred embodiment, said compound is a compound of formula 4, 9, 13, 17, 21, 25, 29, 33, 37, 41, 44, 56, 58 or 77. The formula are shown in the examples.

In a further very preferred embodiment, said compound is a compound of formula 4, 21, 25, 33, 37, 41 or 44. The formula are shown in the examples.

In a further very preferred embodiment, said compound is a compound of formula 4, 9, 13, 17, 21, 25, 29, 33, 37, 41, 44, 56, 58 or 77, wherein at least one of sialic acid moiety is replaced by a replacement moiety as shown and defined in formula (Ia) or formula (Ib)

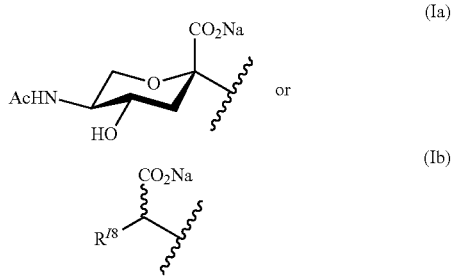

wherein for said replacement moiety of formula (Ib), $R^{I8}$ is H, $C_1$-$C_8$-alkyl, $C_1$-$C_8$-alkyl-cycloalkyl, $C_1$-$C_8$-alkenyl, $C_1$-$C_8$-alkynyl, aryl, substituted aryl, wherein preferably said substitution of said aryl is by halogen, $C_1$-$C_8$-alkoxy, $C_1$-$C_8$-alkyl; heteroaryl, substituted heteroaryl, wherein preferably said substitution of said hetereoaryl is by halogen, $C_1$-$C_8$-alkoxy, $C_1$-$C_8$-alkyl; arylalkyl, substituted arylalkyl, wherein preferably said substitution of said arylalkyl is by halogen, $C_1$-$C_8$-alkoxy, $C_1$-$C_8$-alkyl; heteroarylalkyl, substituted heteroarylalkyl, wherein preferably said substitution of said heteroarylalkyl is by halogen, $C_1$-$C_8$-alkoxy, $C_1$-$C_8$-alkyl; cycloalkyl, cycloalkyl-$C_1$-$C_8$-alkyl, t-butyl, adamantyl, triazolyl all of which independently substituted with $C_1$-$C_8$ alkyl, aryl, heteroaryl, halogen.

In a further very preferred embodiment, said compound is a compound of formula 4, 21, 25, 33, 37, 41 or 44, wherein at least one of sialic acid moiety is replaced by a replacement moiety as shown and defined in formula (Ia) or formula (Ib)

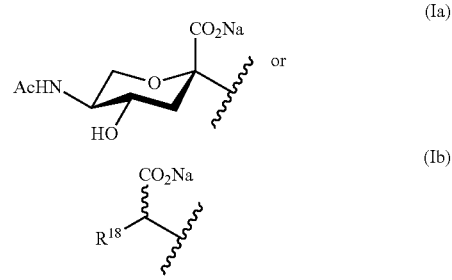

wherein for said replacement moiety of formula (Ib), $R^{78}$ is H, $C_1$-$C_8$-alkyl, $C_1$-$C_8$-alkyl-cycloalkyl, $C_1$-$C_8$-alkenyl, $C_1$-$C_8$-alkynyl, aryl, substituted aryl, wherein preferably said substitution of said aryl is by halogen, $C_1$-$C_8$-alkoxy, $C_1$-$C_8$-alkyl; heteroaryl, substituted heteroaryl, wherein preferably said substitution of said hetereoaryl is by halogen, $C_1$-$C_8$-alkoxy, $C_1$-$C_8$-alkyl; arylalkyl, substituted arylalkyl, wherein preferably said substitution of said arylalkyl is by halogen, $C_1$-$C_8$-alkoxy, $C_1$-$C_8$-alkyl; heteroarylalkyl, substituted heteroarylalkyl, wherein preferably said substitution of said heteroarylalkyl is by halogen, $C_1$-$C_8$-alkoxy, $C_1$-$C_8$-alkyl; cycloalkyl, cycloalkyl-$C_1$-$C_8$-alkyl, t-butyl, adamantyl, triazolyl all of which independently substituted with $C_1$-$C_8$ alkyl, aryl, heteroaryl, halogen.

Furthermore the invention relates to therapeutically acceptable polymers comprising a multitude of substituents derived from the inventive compounds, wherein said compounds are connected to the polymer backbone by way of the linker Z, and wherein the connection is effected via the SH-moiety of linker Z. Typically, said inventive polymer further comprises spacer moieties for coupling of said SH-moieties of the linker Z to reactive moieties on the polymer backbone. Such spacer moieties are known to the skilled person in the art and preferred examples are described herein.

Thus, in another aspect, the present invention provides for a polymer comprising a multitude of the inventive compounds, wherein said compounds are connected to the polymer backbone by way of said linker Z, and wherein said connection is effected via the SH—group of said linker Z. Typically, said inventive polymer further comprises spacer moieties for coupling of said SH-moieties of the linker Z to reactive moieties on the polymer backbone. Preferred examples are described herein.

In a further aspect, the present invention provides for a polymer comprising (i) a multitude of compounds of formula (I), (ii) a multitude of compounds of formula (II) or (iii) a multitude of compounds of formula (I) and of formula (II), wherein said compounds are connected to the polymer backbone by way of said linker Z, and wherein said connection is effected via the SH—group of said linker Z. Preferably said multitude of compounds of formula (I) and/or of formula (II) are either identical compounds of formula (I) and/or of formula (II) or different compounds selected from of formula (I) and/or of formula (II). Typically, said inventive polymer further comprises spacer moieties for coupling of said SH-moieties of the linker Z to reactive moieties on the polymer backbone. Preferred examples are described herein.

In a further preferred embodiment, said polymer comprises (i) a multitude of compounds of formula (I), (ii) a multitude of compounds of formula (II) or (iii) a multitude of compounds of formula (I) and of formula (II), wherein said compounds are connected to the polymer backbone by way of said linker Z, and wherein said connection is effected via the SH—group of said linker Z, and wherein said linker Z is —N($R^a$)—A—B—$CH_2$—$(CH_2)_q$—SH, wherein $R^a$ is H, $C_1$-$C_4$-alkyl, $C_1$-$C_4$-alkoxy, $CH_2C_6H_5$, $CH_2CH_2C_6H_5$, $OCH_2C_6H_5$, or $OCH_2CH_2C_6H_5$; A is $C_1$-$C_7$-alkylene, $C_1$-$C_7$-alkoxy, $C_1$-$C_4$-alkyl—$(OCH_2CH_2)_pO$—$C_1$-$C_4$-alkyl, or $C_1$-$C_7$-alkoxy-$R^b$, wherein $R^b$ is an optionally substituted aryl or an optionally substituted heteroaryl, and wherein p is 0 to 6, preferably p is 1, 2 or 3, and further preferably p is 1; B is NHC(O), S or $CH_2$; q is 0 to 6, preferably q is 1, 2, 3 or 4, and further preferably q is 1 or 2; and wherein said linker Z is covalently bound via its —N($R^a$)-group to the reducing end of said carbohydrate moiety. Preferably said multitude of compounds of formula (I) and/or of formula (II) are either identical compounds of formula (I) and/or of formula (II) or different compounds selected from of formula (I) and/or of formula (II). Typically, said inventive polymer further comprises spacer moieties for coupling of said SH-moieties of the linker Z to reactive moieties on the polymer backbone. Preferred examples are described herein.

Preferred embodiments of said linker Z are as follows. Thus, in one embodiment, $R^a$ is H, $CH_3$, $CH_2CH_3$, $CH_2CH_2CH_3$, $CH(CH_3)_2$, $OCH_3$, $OCH_2CH_3$, $OCH_2CH_2CH_3$, $CH_2C_6H_5$, $OCH_2C_6H_5$; A is $O(CH_2)_pCH_2$, $(CH_2)_pCH_2$, $CH_2(OCH_2CH_2)_pOCH_2$, $(OCH_2CH_2)_pOCH_2CH_2$ or $O(CH_2)_pC_6H_5$; and B is NHC(O), S or $CH_2$. In a preferred embodiment, $R^a$ is $CH_3$ or $OCH_3$; A is $O(CH_2)_pCH_2$, $(CH_2)_pCH_2$, $CH_2(OCH_2CH_2)_pOCH_2$, $(OCH_2CH_2)_pOCH_2CH_2$ or $O(CH_2)_pC_6H_5$; and B is NHC(O) or S. Preferably, when B is S, and A is $(CH_2)_pCH_2$, then q is 1 to 6, preferably 1, 2 or 3.

In a further preferred embodiment of said linker comprised by said inventive polymer, $R^a$ is $CH_3$ or $OCH_3$; A is $O(CH_2)_pCH_2$, $(CH_2)_pCH_2$, $CH_2(OCH_2CH_2)_pOCH_2$, $(OCH_2CH_2)_pOCH_2CH_2$ or $O(CH_2)_pC_6H_5$; and B is NHC(O). In another preferred embodiment of said linker comprised by said inventive polymer, $R^a$ is $CH_3$; A is $O(CH_2)_pCH_2$, $(CH_2)_pCH_2$, $CH_2(OCH_2CH_2)_pOCH_2$, $(OCH_2CH_2)_pOCH_2CH_2$ or $O(CH_2)_pC_6H_5$; and B is NHC(O) or S. Preferably, when B is S and A is $(CH_2)_pCH_2$, then q is 1 to 6, preferably 1, 2 or 3. In a further preferred embodiment of said linker comprised by said inventive polymer, $R^a$ is $CH_3$ or $OCH_3$; A is $O(CH_2)_pCH_2$, $(CH_2)_pCH_2$, $CH_2(OCH_2CH_2)_pOCH_2$, $(OCH_2CH_2)_pOCH_2CH_2$ or $O(CH_2)_pC_6H_5$; B is NHC(O) or S; and q is 1 to 6, preferably 1, 2, 3, 4 or 5, preferably 2 or 4, further preferably 2.

Preferably, said linker Z is of a formula selected from any one of the formula (a) to (g):

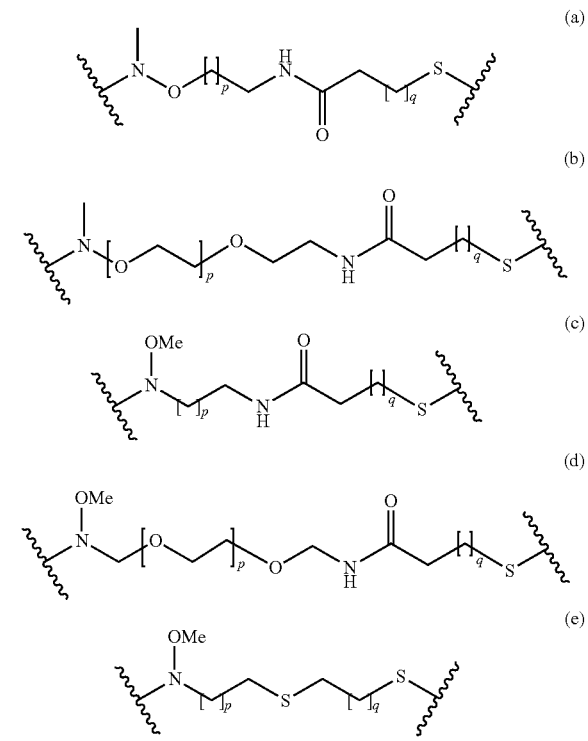

-continued

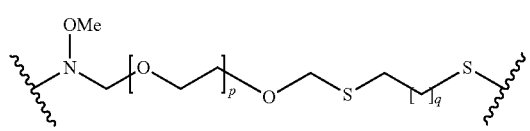
(f)

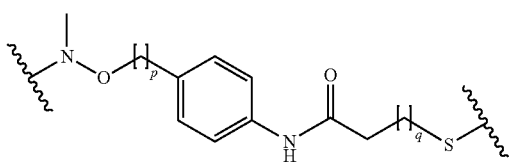
(g)

wherein p is between 0 and 6, preferably 1 to 3, in particular 1, and q is between 0 and 6, preferably between 2 and 4, in particular 2 In one embodiment, when said linker Z is of formula (e), then p and q are independently 1 to 6, preferably 1, 2 or 3; wherein, when p is 2, then q is 1 to 6, preferably 1 or 3 to 6, and when q is 2, then p is 3 to 6. In another embodiment, when said linker Z is of formula (e), then p and q are not both 2.

Preferably, and in light of the general formula of the present invention, said linker Z is of a formula selected from any one of the formula (a) to (g):

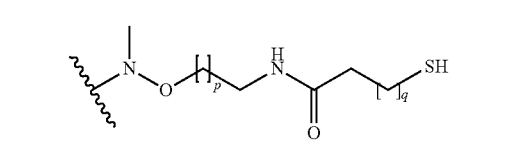
(a)

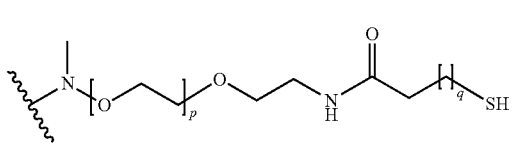
(b)

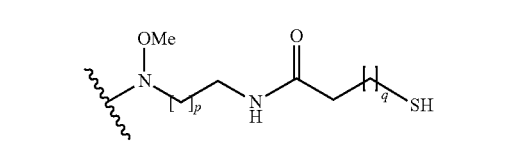
(c)

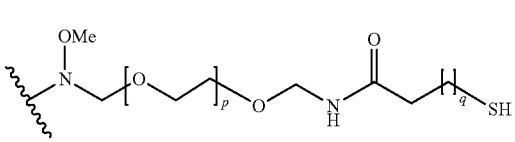
(d)

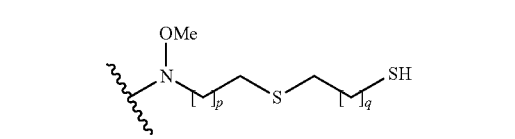
(e)

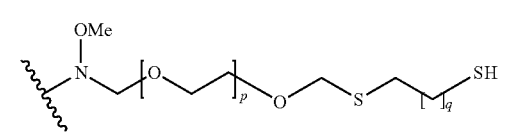
(f)

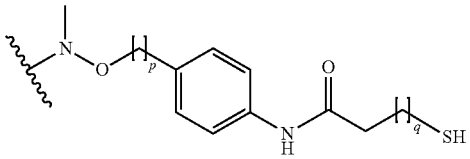
(g)

wherein p is between 0 and 6, preferably 1 to 3, in particular 1, and q is between 0 and 6, preferably between 2 and 4, in particular 2 In one embodiment, when said linker Z is of formula (e), then p and q are independently 2 to 6, preferably 2, 3 or 4; wherein, when p is 2, then q is 1 to 6, preferably 1 or 3 to 6, and when q is 2, then p is 3 to 6. In another embodiment, when said linker Z is of formula (e), then p and q are not both 2.

In a very preferred embodiment, said linker Z is —N(CH$_3$)—O(CH$_2$)$_2$—NHC(O)(CH$_2$)$_3$—SH. The invention further particularly relates to compounds of formula (I) and (II) and to therapeutically acceptable polymers comprising a multitude of these compounds, including polymers with loading of a multitude of one identical compound of formula (I) or (II) or a multitude being a combination of several different compounds of formula (I) or (II). Preferred polymers in said context are polymers with loading of one or several of compounds of formula (I) or (II), wherein said compounds of formula (I) or (II) are preferably selected from 4*, 9*, 13*, 17*, 21*, 25*, 29* or 33*, and 46*-60*.

The inventive polymer comprising the multitude of identical or different compounds of formula (I) and/or (II) wherein the SH—group of said linker Z connects said compounds to the polymer backbone, is preferably an α-amino acid polymer, and hereby typically and preferably a homomeric or heteromeric α-amino acid polymer, an acrylic acid or methacrylic acid polymer or copolymer, or a N-vinyl-2-pyrrolidone-vinylalcohol copolymer, a chitosan polymer, or a polyphosphazene polymer.

In a preferred embodiment, the polymer backbone is an α-amino acid polymer, an acrylic acid or methacrylic acid polymer or copolymer, a N-vinyl-2-pyrrolidone-vinyl alcohol copolymer, a chitosan polymer, or a polyphosphazene polymer.

In another preferred embodiment, the polymer backbone is an α-amino acid polymer.

In a further preferred embodiment, the polymer backbone is an α-amino acid polymer and said α-amino acid of said α-amino acid polymer is lysine, ornithine, glutamic acid, aspartic acid or serine.

In a very preferred embodiment, the polymer backbone is poly-lysine, and wherein preferably the molecular weight of said poly-lysine is 1'000 Da to 300'000 Da.

In a further preferred embodiment, the percentage of loading of the carbohydrate moiety of said compound onto the polymer backbone is between 10 and 90%, preferably between 20 and 70%, and in particular between 30 and 60%. The latter means that 30 to 60% of the reactive polymer side chains and, if applicable the spacer moiety, are reacted with the —SH group of said linker Z. The percentage of loading of the carbohydrate moiety of said compound onto the polymer backbone is typically and preferably determined by NMR spectroscopy and refers to % mole/mole.

Further particular examples of polymers of the invention are (A) a poly-α-amino acid, wherein the amino acid carries a side chain aminoalkyl function, such as in poly-lysine, in particular poly-L-lysine or poly-D-lysine, and the amino group is connected via a spacer moiety to the SH—group of said linker Z. A typical and preferred spacer moiety comprises a terminal CH$_2$-group, wherein said terminal CH$_2$-group of said spacer moiety is connected to the S—of said linker Z. A preferred spacer moiety is an acetyl group.

(B) a poly-α-amino acid (D- and L-form), wherein the amino acid carries a side chain carbonylalkyl function, such as in poly-aspartic acid, poly-glutamic acid, poly-asparagine or poly-glutamine, and the carbonyl group (which corresponds to the original carboxy group in aspartic acid and glutamic acid, respectively) is connected via a spacer moiety to the SH—group of said linker Z. A typical and preferred spacer moiety comprises a terminal CH$_2$-group, wherein said terminal CH$_2$-group of said spacer moiety is connected to the S—of said linker Z.

(C) a poly-α-amino acid (D- and L-form), wherein the amino acid carries a side chain hydroxyalkyl or hydroxyaryl function, such as in poly-serine, poly-threonine, poly-tyrosine, or poly-hydroxyproline, and the hydroxy group is connected via a spacer moiety to the SH—group of said linker Z. A typical and preferred spacer moiety comprises a terminal CH$_2$-group, wherein said terminal CH$_2$-group of said spacer moiety is connected to the S—of said linker Z.

(D) a poly-α-amino acid, wherein the amino acid carries a side chain thiolalkyl function, such as in poly-cysteine, wherein the terminal CH$_2$ group of the amino acid side-chain (next to the thiol) is connected to the terminal SH group of linker Z, typically and preferably as a thioether;

(E) Co-polymers of two or more different α-amino acids connected via a spacer moiety to the SH—group of said linker Z, as described in (A)-(D);

(F) poly-acrylic acid, poly-methacrylic acid or a copolymer of acrylic and methacrylic acid, wherein the carboxy group is connected via a spacer moiety to the SH—group of said linker Z. A typical and preferred spacer moiety comprises a terminal CH$_2$-group, wherein said terminal CH$_2$-group of said spacer moiety is connected to the S—of said linker Z.

(G) a copolymer of N-vinyl-2-pyrrolidone and vinyl alcohol, wherein the hydroxy group of the vinyl alcohol part of the copolymer is connected via a spacer moiety to the SH—group of said linker Z. A typical and preferred spacer moiety comprises a terminal CH$_2$-group, wherein said terminal CH$_2$-group of said spacer moiety is connected to the S—of said linker Z.

(H) chitosan, wherein the amino group is connected via a spacer moiety to the SH—group of said linker Z. A typical and preferred spacer moiety comprises a terminal CH$_2$-group, wherein said terminal CH$_2$-group of said spacer moiety is connected to the S—of said linker Z; and (I) a polyphosphazene polymer, wherein the terminal ester group is connected via a spacer moiety to the SH—group of said linker Z. A typical and preferred spacer moiety comprises a terminal CH$_2$-group, wherein said terminal CH$_2$-group of said spacer moiety is connected to the S—of said linker Z. A preferred spacer moiety is an acetyl group.

In a particular embodiment, a polymer (A) comprises the partial formula (III)

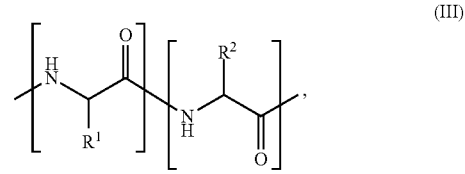

(III)

wherein $R^1$ is an aminoalkyl substituent connected to said linker Z, wherein the SH—group of of said linker Z is connected to the terminal amino group of $R^1$ via a spacer moiety, wherein typically and preferably said spacer moiety is an acetyl group, $R^2$ is 2,3-dihydroxypropylthioacetyl-aminoalkyl, which is a capped amino function having a solubilizing substituent, and the relation between the two bracketed entities with $R^1$ and $R^2$, respectively, in the polymer indicates the relation of carbohydrate loading to capped amino function.

For example, $R^1$ is of formula (IIIa)

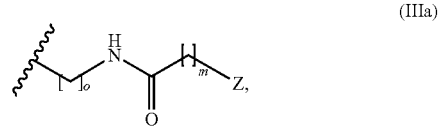

(IIIa)

and $R^2$ is of formula (IIIb)

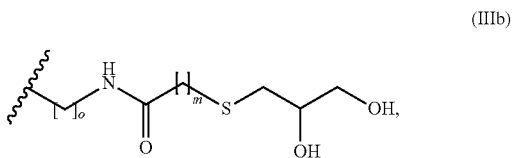

(IIIb)

wherein o is between 1 and 6, preferably 3 or 4 and m is between 1 and 6, preferably between 1 and 2, in particular 1.

When o is 3, substituent $R^1$ represents a side chain of poly-ornithine, and when o is 4, substituent $R^1$ represents a side chain of poly-lysine, connected to said SH—group of said linker Z which linker Z is comprised by the inventive compounds, and preferably by the inventive compounds of formula (I) or (II), The poly-amino acid can be linear, hyperbranched or dendritic, as described by Z. Kadlecova et al., Biomacromolecules 2012, 13:3127-3137, for poly-lysine as follows:

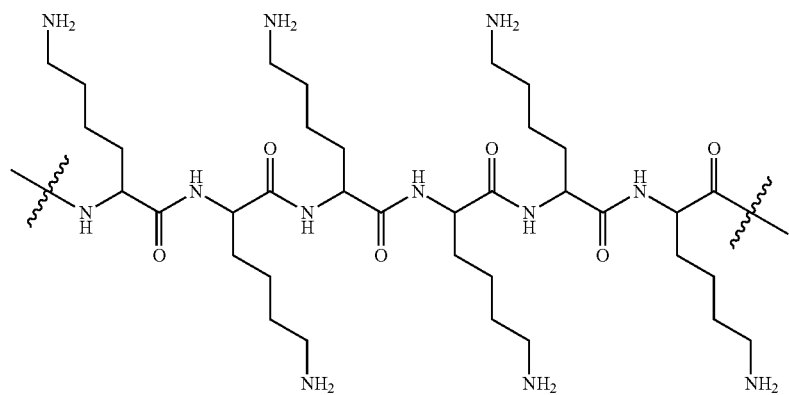
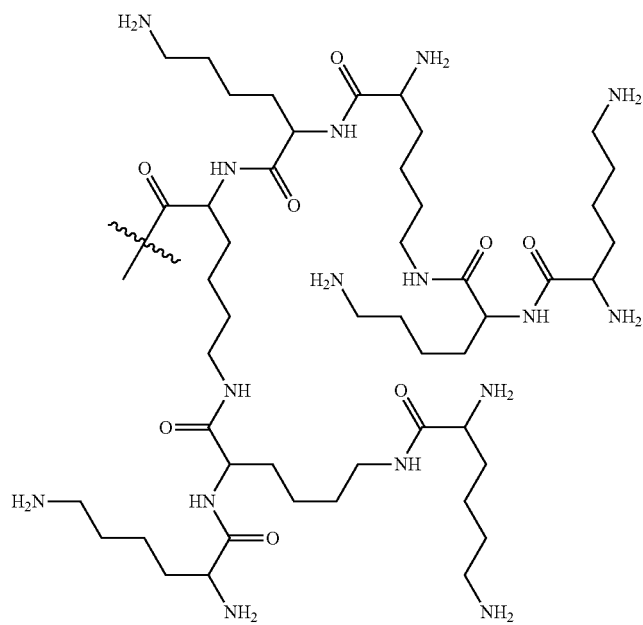
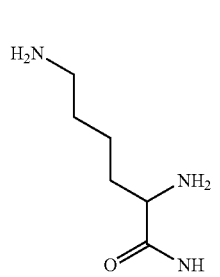
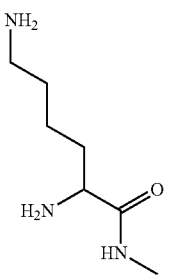
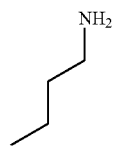

-continued

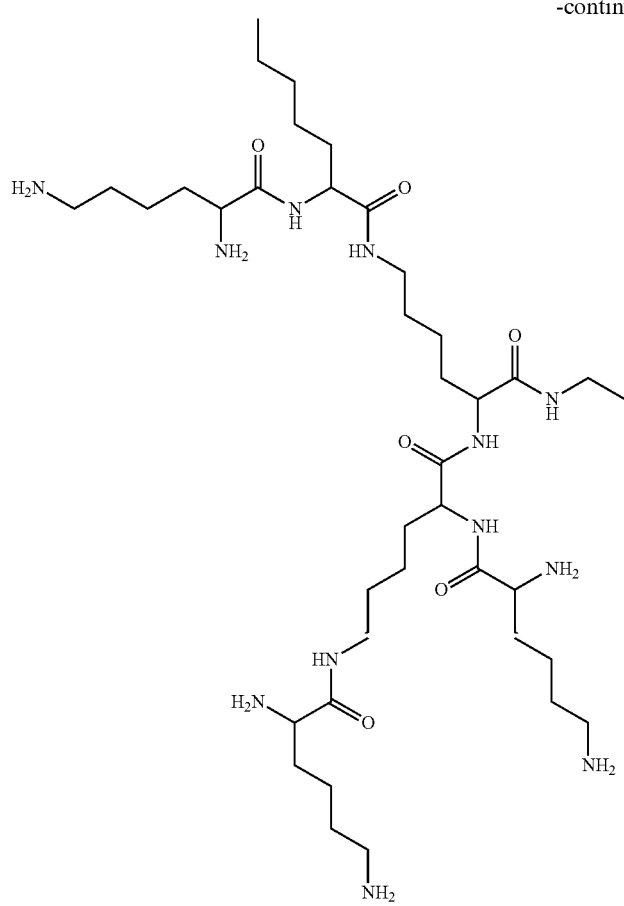

The poly-lysine used to prepare polymer (A) of formula (III) has preferably a molecular weight between 1'000 and 300'000 Da, in particular 30'000 to 70'000 Da, and such polymers further connected via the SH—group of the linker Z to compounds of formula (I) and/or (II) and with a capping 2,3-dihydroxypropylthio-acetylylaminoalkyl residue are preferred. For example, the polylysine polymer is first functionalized by chloroacetylation. Reaction of the chloroacetylated polymer with said linker Z comprising the terminal thiol functionality by nucleophilic substitution gives access to the desired polymers.

In a particular embodiment, a polymer (B) comprises the partial formula (III)

(III)

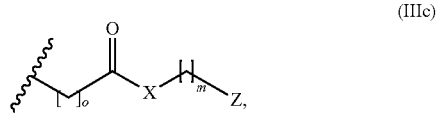

wherein
$R^1$ is a carbonylalkyl substituent connected to said linker Z, wherein the SH—group of said linker Z is connected to the —CH$_2$-group of $R^1$,
$R^2$ is 2,3-dihydroxypropylthio-carbonylalkyl, and the relation between the two bracketed entities with $R^1$ and $R^2$, respectively, in the polymer indicates the relation of carbohydrate loading to capped carbonyl or carboxy function.

For example, $R^1$ is of formula (IIIc)

(IIIc)

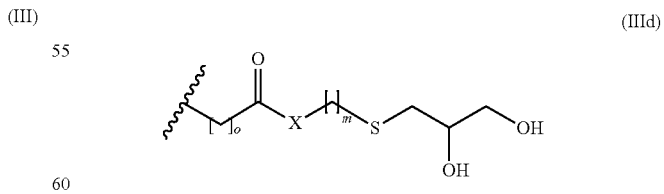

and $R^2$ is of formula (IIId)

(IIId)

wherein X is either oxygen or nitrogen, o is between 1 and 6, preferably 1 or 2, m is between 1 and 6, preferably between 1 and 2, in particular 1.

When o is 1 and X is O, substituent $R^1$ represents a side chain of poly-aspartic acid, and when o is 2 and X is O, substituent $R^1$ represents a side chain of poly-glutamic acid, when o is 1 and X is N, substituent $R^1$ represents a side chain of poly-asparagine, and when o is 2 and X is N, substituent $R^1$ represents a side chain of poly-glutamine, connected to said SH—group of said linker Z which linker Z is comprised by the inventive compounds, and preferably by the inventive compounds of formula (I) or (II),
and $R^2$ is 2,3-dihydroxypropylthio-carbonylalkyl, i.e. a capped carboxy or amide function having a solubilizing substituent.

The poly-aspartic acid used to prepare polymer (B) of formula (IV) has preferably a molecular weight between 1'000 and 300'000 Da, in particular 30'000 to 70'000 Da, and such polymers further connected via the SH—group of said linker Z to compounds of formula (I) and/or (II) and with a capping 2,3-dihydroxypropylthio-carbonylalkyl residue are preferred. For example, polyaspartic acid is first functionalized by esterification. Reaction of the chloroacetylated polymer with said linker Z comprising the terminal thiol functionality by nucleophilic substitution gives access to the desired polymers.

In case of poly-aspartic acid or poly-glutamic acid the polymer can be linear, hyperbranched or dendritic.

In a particular embodiment, a polymer (C) comprises the partial formula (III)

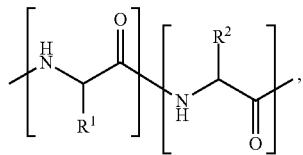

(III)

wherein
$R^1$ is a hydroxyalkyl or hydroxyaryl substituent connected to said linker Z, wherein the SH—group of said linker Z is connected to the —$CH_2$-group of $R^1$,
$R^2$ is 2,3-dihydroxypropylthioacetyl-hydroxyalkyl (or -hydroxyaryl),
and the relation between the two bracketed entities with $R^1$ and $R^2$, respectively, in the polymer indicates the relation of carbohydrate loading to capped hydroxy function.

For example, in the case of poly-serine and analogs, $R^1$ is of formula (IIIe)

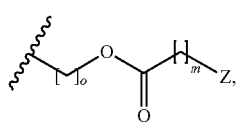

(IIIe)

and $R^2$ is of formula (IIIf)

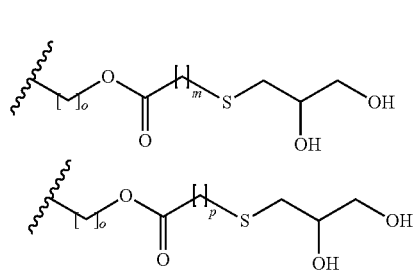

(IIIf)

wherein o is between 1 and 6, preferably 1 or 2, in particular 1, m is between 1 and 6, preferably between 1 and 2, in particular 1.

When o is 1, substituent $R^1$ represents a side chain of poly-serine, connected to said SH—group of said linker Z, which linker Z is comprised by the inventive compounds, and preferably by the inventive compounds of formula (I) or (II), and $R^2$ is 2,3-dihydroxy-propylthio-hydroxyalkyl, i.e. a capped hydroxy function having a solubilizing substituent.

The poly-serine (and other hydroxy-functionalized α-amino acid side-chains) used to prepare polymer (C) of formula (III) has preferably a molecular weight between 1'000 and 300'000 Da, in particular 30'000 to 70'000 Da, and such polymers further connected via the SH—group of said linker Z to compounds of formula (I) and/or (II) and with a capping 2,3-dihydroxypropylthio-hydroxyalkyl residue are preferred. For example, polyserine is first functionalized by esterification. Reaction of the chloroacetylated polymer with said linker Z comprising the terminal thiol functionality by nucleophilic substitution gives access to the desired polymers.

In a particular embodiment, a polymer (D) comprises the partial formula (IV)

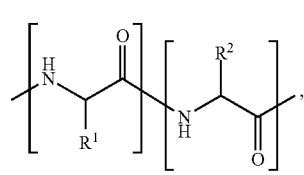

(III)

wherein
$R^1$ is a thioalkyl substituent connected to said linker Z, wherein the SH—group of said linker Z is connected to the —$CH_2$-group of $R^1$,
$R^2$ is 2,3-dihydroxypropylthioalkyl,
and the relation between the two bracketed entities with $R^1$ and $R^2$, respectively, in the polymer indicates the relation of carbohydrate loading to capped thiol function.

For example, $R^1$ is of formula (IIIg)

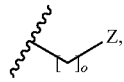

(IIIg)

and $R^2$ is of formula (IIIh)

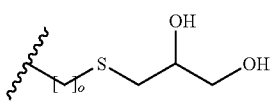

(IIIh)

wherein o is between 1 and 6, preferably 1 or 2, in particular 1.

When o is 1, substituent $R^1$ represents a side chain of poly-cysteine, connected to said SH—group of said linker Z, which linker Z is comprised by the inventive compounds, and preferably by the inventive compounds of formula (I) or (II), and hereby connected to the —$CH_2$-group of $R^1$, and $R^2$ is 2,3-dihydroxypropylthio-alkyl, i.e. a capped thiol function having a solubilizing substituent.

The poly-cysteine used to prepare polymer (D) of formula (III) has preferably a molecular weight between 1'000 and 300'000 Da, in particular 30'000 to 70'000 Da, and such polymers further connected via the SH—group of said linker Z to compounds of formula (I) and/or (II) with a capping 2,3-dihydroxypropylthio-thioalkyl residue are preferred. For example, the polycysteine polymer is reacted with a compound containing a terminal alkene group via a radical reaction.

In a particular embodiment, a polymer (F) comprises the partial formula (IV)

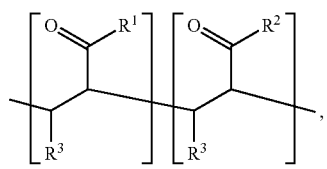

(IV)

wherein
$R^1$ is an aminoalkyl substituent connected to said linker Z, wherein the SH—group of said linker Z is connected to the —CH$_2$-group of $R^1$ (IVa).
$R^2$ is 2,3-dihydroxypropylthio-acetylaminoalkylamino or a related amino substituent, and
$R^3$ is hydrogen or methyl;
and the relation between the two bracketed entities with $R^1$ and $R^2$, respectively, in the polymer indicates the relation of carbohydrate loading to capped amide function.

For example, $R^1$ is of formula (IVa)

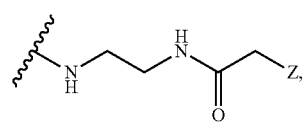

(IVa)

and $R^2$ is of formula (IVb), $R^3$ is of formula (IVc)

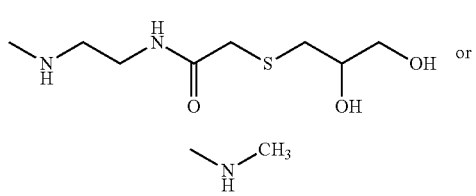

(IVb)

(IVc)

In another embodiment $R^1$ is of formula (IVd)

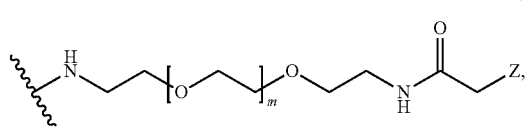

(IVd)

and $R^2$ is of formula (IVe)

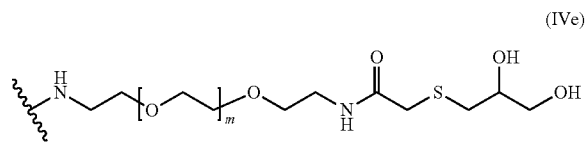

(IVe)

wherein m is between 1 and 10, preferably between 1 and 4.
In another embodiment $R^1$ is of formula (IVf)

(IVf)

wherein r is between 1 and 6, preferably between 1 and 4, in particular 2, and
$R^2$ is of formula (IVc) (above).

The poly-acrylic acid used to prepare polymer (F) of formula (IV) has preferably a molecular weight between 1'000 and 400'000 Da, in particular 30'000 to 160'000 Da, and such polymers further connected via the SH—group of said linker Z to compounds of formula (I) and/or (II) and with a capping 2,3-dihydroxypropylthio-acetylaminoalkylamino residue are preferred.

In a particular embodiment, a polymer (G) comprises the partial formula (V)

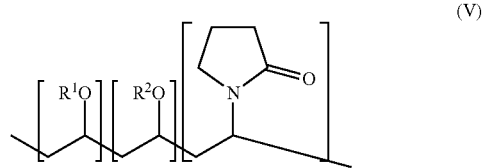

(V)

wherein
$R^1$ is an aminoalkyl substituent connected to said linker Z, wherein the SH—group of said linker Z is connected to the —CH$_2$-group of $R^1$ (Va).
$R^2$ is 2,3-dihydroxypropylthio-acetylaminoalkylaminocarbonyl or a related aminocarbonyl substituent, and the relation between the two bracketed entities with $R^1$ and $R^2$, respectively, in the polymer indicates the relation of carbohydrate loading to capped hydroxy function.

For example, $R^1$ is of formula (Va)

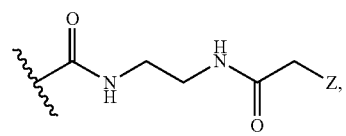

(Va)

and $R^2$ is of formula (Vb)

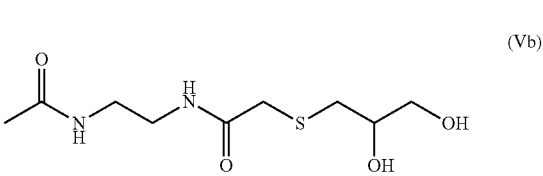 [SMILES: CC(=O)NCCNC(=O)CSCC(O)CO]

(Vb)

In another embodiment R¹ is of formula (Vc)

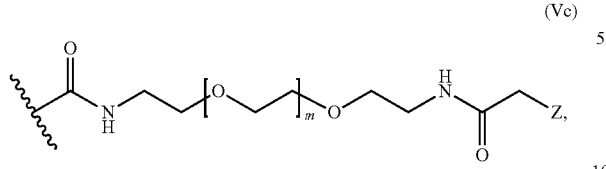
(Vc)

and R² is of formula (Vd)

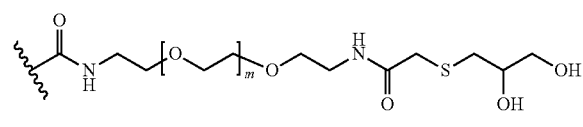
(Vd)

wherein m is between 1 and 10, preferably between 1 and 4.

In another embodiment R¹ is of formula (Ve)

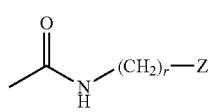
(Ve)

and R² is of formula (Vf)

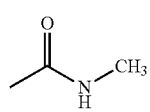
(Vf)

wherein r is between 1 and 6, preferably between 1 and 4, in particular 2.

The copolymer used to prepare polymer (G) of formula (VI) has preferably a molecular weight between 1'000 and 400'000 Da, in particular 30'000 to 160'000 Da, and such polymers further connected via the SH—group of said linker Z to compounds of formula (I) and/or (II) and with a capping 2,3-dihydroxypropylthio-carbonylaminoalkylaminocarbonyl residue are preferred.

In a particular embodiment, a polymer (H) comprises the partial formula (VI)

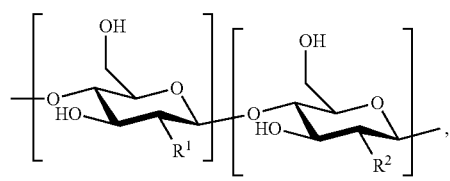
(VI)

wherein
R¹ is an aminoalkyl substituent connected to said linker Z, wherein the SH—group of said linker Z is connected to the —CH₂-group of R¹.
R² is 2,3-dihydroxypropylthio-acetylamine,
and the relation between the two bracketed entities with R¹ and R², respectively, in the polymer indicates the relation of carbohydrate loading to capped amino function.

For example, R¹ is of formula (VIa)

(VIa)

and R² is of formula (VIb)

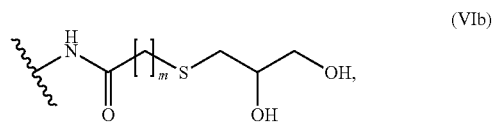
(VIb)

wherein o is between 1 and 6, preferably 3 or 4 and m is between 1 and 6, preferably between 1 and 2, in particular 1.

The chitosan used to prepare polymer (H) of formula (VI) has preferably a molecular weight between 1'000 and 300'000 Da, in particular 30'000 to 70'000 Da, and such polymers connected via the SH—group of said linker Z to compounds of formula (I) and/or (II) and connected to a capping 2,3-dihydroxypropylthio-acetylamine residue are preferred. For example, the chitosan polymer is first functionalized by chloroacetylation of the amino groups. Reaction of the chloroacetylated polymer with said linker Z comprising the terminal thiol functionality by nucleophilic substitution gives access to the desired polymers.

In a particular embodiment, a polymer (I) comprises the partial formula (VII)

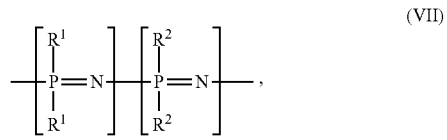
(VII)

wherein
R¹ is a carbonylalkyl or carbonylaryl substituent connected to said linker Z, wherein the SH—group of said linker Z is connected to the —CH₂-group of R¹,
R² is 2,3-dihydroxypropylthio-carbonylalkyl or carbonylaryl,
and the relation between the two bracketed entities with R¹ and R², respectively, in the polymer indicates the relation of carbohydrate loading to capped carboxy function.

For example, R¹ is of formula (VIIa)

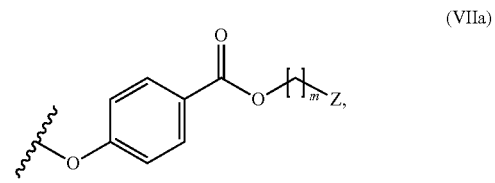
(VIIa)

and R² is of formula (VIIb)

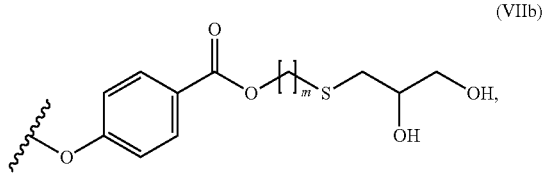

(VIIb)

wherein m is between 1 and 6, preferably between 1 and 2, in particular 1.

The polyphosphazen used to prepare polymer (I) of formula (VII) has preferably a molecular weight between 1'000 and 300'000 Da, in particular 30'000 to 70'000 Da, and such polymers further connected via the SH—group of said linker Z to compounds of formula (I) and/or (II) and with a capping 2,3-dihydroxypropylthio-carbonylalkyl or carbonylaryl residue are preferred. For example, the polyphosphazene is first functionalized by esterification. Reaction of the chloroacetylated polymer with said linker Z comprising the terminal thiol functionality by nucleophilic substitution gives access to the desired polymers.

From the group of polymers (A)-(I), preferred polymers are α-amino acid polymers (D- and L-form) or combinations (co-polymers) of different α-amino acids (A)-(D). More preferred are α-amino acid polymers consisting of poly-lysine, poly-ornithine, poly-aspartic acid, poly-glutamic acid. Particularly preferred among these α-amino acid polymers is poly-L-lysine.

In a further very preferred embodiment, said polymer is a polymer of formula 6, 10, 14, 18, 22, 26, 30, 34, 38, 42, 45, 78, 86, 89, 93, 100 or 102, wherein said formulas are shown in the experimental section, and wherein for each of said polymer n is independently 20-1200, preferably 100-1100, further preferably 200-500, and wherein for each of said polymer x is independently 10-90, preferably 30-60, and further preferably 40-50.

In a further very preferred embodiment, said polymer is a polymer of formula 6, 10, 14, 18, 22, 26, 30, 34, 38, 42, 45, 78, 86, 89, 93, 100 or 102, wherein said formulas are shown in the experimental section, and wherein for each of said polymer n is independently 100-1100, preferably 200-500, and wherein for each of said polymer x is independently 30-60, and further preferably 40-50.

In a further very preferred embodiment, said polymer is a polymer of formula 6, 22, 26, 34, 38, 42, 45, wherein said formulas are shown in the experimental section, and wherein for each of said polymer n is independently 20-1200, preferably 100-1100, further preferably 200-500, and wherein for each of said polymer x is independently 10-90, preferably 30-60, and further preferably 40-50.

In a further very preferred embodiment, said polymer is a polymer of formula 6, 22, 26, 34, 38, 42, 45, wherein said formulas are shown in the experimental section, and wherein for each of said polymer n is independently 100-1100, preferably 200-500, and wherein for each of said polymer x is independently 30-60, and further preferably 40-50.

The general terms used hereinbefore and hereinafter preferably have within the context of this disclosure the following meanings, unless otherwise indicated:

Where the plural form is used for compounds and the like, this is taken to mean also a single compound, or the like.

The term "glycoepitope", as used herein, refers to the carbohydrate moiety that is recognized by an antibody or by a lectin-like glycan-binding protein. Preferably, the term "glycoepitope", as used herein, refers to a carbohydrate moiety comprised by a glycosphingolipid expressed in the nervous system. Glycosphingolipids are known to the skilled person in the art and are a subset of glycolipids defined by their content of sphingosine and are particularly relevant to the nervous system. Subtypes of glycosphingolipids are cerebrosides (single carbohydrate attached to the lipid part), (neo)lacto-, ganglio-, or sulfoglucuronyl paraglobside-type (sialylated or non-sialylated oligosaccharide attached to the lipid part). Preferably, the term "glycoepitope", as used herein, refers to the carbohydrate moiety that is recognized by an antibody or by a lectin-like glycan-binding protein, wherein said glycoepitope is comprised by a glycosphingolipid that is expressed in the nervous system and wherein said a glycosphingolipid is selected from cerebrosides, (neo)lactosides, gangliosides, sulfoglucuronyl paragloboside or carbohydrate moieties comprised by compounds of formula I or formula II.

Thus, in a preferred embodiment, said glycoepitope comprised by said glycosphingolipid of the nervous system is selected from the cerebroside-, (neo)lacto-, ganglio-, or sulfoglucuronyl paragloboside-type or a carbohydrate moiety comprised by a compound of formula (I) or formula (II).

In a further preferred embodiment, said glycoepitope comprised by said glycosphingolipid of the nervous system is selected from the cerebroside-, (neo)lacto-, or ganglio-type. In another preferred embodiment, said glycoepitope comprised by said glycosphingolipid of the nervous system is selected from a carbohydrate moiety comprised by a compound of formula (I). In another preferred embodiment, said glycoepitope comprised by said glycosphingolipid of the nervous system is selected from a carbohydrate moiety comprised by a compound of formula (II).

The term "reducing end", as used herein in the context of the glycoepitope of the present invention and of the specific inventive compounds, refers to the terminal monosaccharide of the glycoepitope with a free anomeric carbon that is not involved in a glycosidic bond, wherein said free anomeric carbon bears a hemiacetal group.

The term "$C_1$-$C_4$-alkyl", as used herein refers to straight or branched chain of 1 to 4 carbon atoms and includes butyl, such as n-butyl, sec-butyl, iso-butyl, tert-butyl, propyl, such as n-propyl or iso-propyl, ethyl or methyl. Preferably the term "$C_1$-$C_4$-alkyl", refers to methyl or ethyl, n-propyl or iso-propyl. Further preferably, the term "$C_1$-$C_4$-alkyl", refers to methyl. Correspondingly, the term "$C_1$-$C_8$-alkyl", as used herein refers to straight or branched chain of 1 to 8 carbon atoms. The term "$C_1$-$C_4$-alkyl—(OCH$_2$CH$_2$)$_p$O—$C_1$-$C_4$-alkyl", as used herein, and when referring to the linker Z defined as —N(R$^a$)—A—B—CH$_2$(CH$_2$)$_q$—SH, and when referring to A within said linker Z, should refer, as evident from the description and examples herein, to a bivalent "$C_1$-$C_4$-alkyl—(OCH$_2$CH$_2$)$_p$O—$C_1$-$C_4$-alkyl" group including groups such as —(CH$_2$)$_n$—(OCH$_2$CH$_2$)$_p$O—(CH$_2$)$_n$— with n requal 1 to 4.

The term "$C_1$-$C_7$-alkylene", as used herein, refers to a straight or branched bivalent alkyl chain, preferably to a straight or branched bivalent alkyl chain of 1 to 7 carbon atoms, and includes, for example, —CH$_2$—, —CH$_2$—CH$_2$—, —CH(CH$_3$)—, —CH$_2$—CH$_2$—CH$_2$—, —CH(CH$_3$)—CH$_2$—, or —CH(CH$_2$CH$_3$)—.

The term "$C_1$-$C_7$-alkoxy", as used herein, refers to an alkoxy with a straight or branched chain of 1 to 7 carbon atoms. The term "$C_1$-$C_4$-alkoxy", as used herein, refers to an alkoxy with a straight or branched chain of 1 to 4 carbon atoms and includes methoxy, ethoxy, propoxy, iso-propoxy, n-butoxy, sec-butoxy and tert-butoxy. Preferably, the term "$C_1$-$C_4$-alkoxy", as used herein, refers to methoxy, ethoxy, propoxy. Further preferably, the term "$C_1$-$C_4$-alkoxy", as used herein, refers to methoxy. The term "$C_1$-$C_7$-alkoxy", as used herein, and when referring to the linker Z defined as —N($R^a$)—A—B—$CH_2$($CH_2$)$_q$—SH, and when referring to A within said linker Z, should refer, as evident from the description and examples herein, to a bivalent $C_1$-$C_7$-alkoxy group including groups such as —($CH_2$)$_n$O— or —O($CH_2$)$_n$— with n reqular 1 to 7, typically and very preferably to groups such as —O($CH_2$)$_n$—forming with the N($R^a$) of the linker Z a preferred bonding N($R^a$)—O($CH_2$)$_n$—.

The term "$C_1$-$C_8$-alkenyl", as used herein, refers to is a straight or branched chain containing one or more, e.g. two or three, double bonds, and is preferably $C_1$-$C_4$-alkenyl, such as 1- or 2-butenyl, 1-propenyl, allyl or vinyl.

Double bonds in principle can have E- or Z-configuration. The compounds of this invention may therefore exist as isomeric mixtures or single isomers. If not specified both isomeric forms are intended.

The term "$C_1$-$C_8$-alkynyl", as used herein, refers to is a straight or branched chain comprising one or more, preferably one triple bond. Preferred are $C_1$-$C_4$-alkynyl, such as propargyl or acetylenyl.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The term "aryl", as used herein, refers to a mono- or bicyclic fused ring aromatic group with 5 to 10 carbon atoms optionally carrying substituents, such as phenyl, 1-naphthyl or 2-naphthyl, or also a partially saturated bicyclic fused ring comprising a phenyl group, such as indanyl, indolinyl, dihydro- or tetrahydronaphthyl, all optionally substituted. Preferably, aryl is phenyl, indanyl, indolinyl or tetrahydronaphthyl, in particular phenyl.

The term "heteroaryl", as used herein, refers to an aromatic mono- or bicyclic ring system containing at least one heteroatom, and preferably up to three heteroatoms selected from nitrogen, oxygen and sulfur as ring members. Heteroaryl rings do not contain adjacent oxygen atoms, adjacent sulfur atoms, or adjacent oxygen and sulfur atoms within the ring. Monocyclic heteroaryl preferably refers to 5 or 6 membered heteroaryl groups and bicyclic heteroaryl preferably refers to 9 or 10 membered fused-ring heteroaryl groups. Examples of heteroaryl include pyrrolyl, thienyl, furyl, pyrazolyl, imidazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and benzo or pyridazo fused derivatives of such monocyclic heteroaryl groups, such as indolyl, benzimidazolyl, benzofuryl, quinolinyl, isoquinolinyl, quinazolinyl, pyrrolopyridine, imidazopyridine, or purinyl, all optionally substituted.

Preferably, the term "heteroaryl" refers to a 5- or 6-membered aromatic monocyclic ring system containing at least one heteroatom, and preferably up to three heteroatoms selected from nitrogen, oxygen and sulfur as ring members. Preferably, heteroaryl is pyridyl, pyrimdinyl, pyrazinyl, pyridazinyl, thienyl, pyrazolyl, imidazolyl, thiazolyl, oxadiazolyl, triazolyl, oxazolyl, isoxazolyl, isothiazolyl, pyrrolyl, indolyl, pyrrolopyridine or imidazopyridine; in particular pyridyl, pyrimidinyl, pyrazinyl, pyridazinyl, pyrazolyl, imidazolyl, thiazolyl, oxadiazolyl, triazolyl, indolyl, pyrrolopyridine or imidazopyridine The term "optionally substituted aryl", as used herein, refers to aryl substituted by up to four substituents, preferably up to two substituents. In optionally substituted aryl, preferably in optionally substituted phenyl, substituents are preferably and independently selected from $C_1$-$C_4$-alkyl, $C_1$-$C_4$-alkoxy, amino-$C_1$-$C_4$-alkyl, acylamino-$C_1$-$C_4$-alkyl, aryl-$C_1$-$C_4$-alkyl hydroxy, carboxy, $C_1$-$C_4$-alkoxycarbonyl, aminocarbonyl, hydroxylaminocarbonyl, tetrazolyl, hydroxysulfonyl, aminosulfonyl, halo, or nitro, in particular $C_1$-$C_4$-alkyl, $C_1$-$C_4$-alkoxy, amino-$C_1$-$C_4$-alkyl, acylamino-$C_1$-$C_4$-alkyl, carboxy, $C_1$-$C_4$-alkoxycarbonyl, aminocarbonyl, hydroxylaminocarbonyl, tetrazolyl, or aminosulfonyl.

The term "optionally substituted heteroaryl", as used herein, refers to heteroaryl substituted by up to three substituents, preferably up to two substituents. In optionally substituted heteroaryl, substituents are preferably and independently selected from $C_1$-$C_4$-alkyl, $C_1$-$C_4$-alkoxy, halo-$C_1$-$C_4$-alkyl, hydroxy, $C_1$-$C_4$-alkoxycarbonyl, aminocarbonyl, hydroxylaminocarbonyl, tetrazolyl, aminosulfonyl, halo, aryl-$C_1$-$C_4$-alkyl, or nitro.

Cycloalkyl has preferably 3 to 7 ring carbon atoms, and may be unsubstituted or substituted, e.g. by $C_1$-$C_4$-alkyl or $C_1$-$C_4$-alkoxy. Cycloalkyl is, for example and preferably, cyclohexyl, cyclopentyl, methylcyclopentyl, or cyclopropyl, in particular cyclopropyl.

Acyl designates, for example, alkylcarbonyl, cycloalkylcarbonyl, arylcarbonyl, aryl-$C_1$-$C_4$-alkylcarbonyl, or heteroarylcarbonyl. $C_1$-$C_4$-acyl is preferably lower alkylcarbonyl, in particular propionyl or acetyl. Ac stands for acetyl.

Hydroxyalkyl is especially hydroxy-$C_1$-$C_4$-alkyl, preferably hydroxymethyl, 2-hydroxyethyl or 2-hydroxy-2-propyl.

Haloalkyl is preferably fluoroalkyl, especially trifluoromethyl, 3,3,3-trifluoroethyl or pentafluoroethyl.

Halogen is fluorine, chlorine, bromine, or iodine.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl.

In substituted amino, the substituents are preferably those mentioned as substituents hereinbefore. In particular, substituted amino is alkylamino, dialkylamino, optionally substituted arylamino, optionally substituted arylalkylamino, lower alkylcarbonylamino, benzoylamino, pyridylcarbonylamino, lower alkoxycarbonylamino or optionally substituted aminocarbonylamino.

Particular salts considered are those replacing the hydrogen atoms of the sulfate group and the carboxylic acid function. Suitable cations are, e.g., sodium, potassium, calcium, magnesium or ammonium cations, or also cations derived by protonation from primary, secondary or tertiary amines containing, for example, $C_1$-$C_4$-alkyl, hydroxy-$C_1$-$C_4$-alkyl or hydroxy-$C_1$-$C_4$-alkoxy-$C_1$-$C_4$-alkyl groups, e.g., 2-hydroxyethylammonium, 2-(2-hydroxy-ethoxy)ethyldimethylammonium, diethylammonium, di(2-hydroxyethyl)ammonium, trimethylammonium, triethylammonium, 2-hydroxyethyldimethylammonium, or di(2-hydroxyethyl)methylammonium, also from correspondingly substituted cyclic secondary and tertiary amines, e.g., N-methylpyrrolidinium, N-methylpiperidinium, N-methyl-morpholinium, N-2-hydroxyethylpyrrolidinium, N-2-hydroxyethylpiperidinium, or N-2-hydroxyethylmorpholinium, and the like.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, and vice versa, as appropriate and expedient A preferred polymer backbone in the inventive polymers comprising a multitude of compounds of formula (I) or formula (II) is polylysine, in particular poly-L-lysine.

Preferably the molecular weight of the polylysine is 1'000 to 300'000 kD, preferably 10'000 to 200'000 kD. Particularly preferred is a molecular weight of approximately 50'000 kD, 85'000 kD, 125'000 kD or 200'000 kD. Most preferred is a molecular weight of approximately 50'000 kD.

In particular the invention relates to such polymers wherein the relative loading of polymer backbone with the carbohydrate moiety of said compound of formula (I) and/or (II) is 10-90%, meaning that 10-90% of all lysine side chains in the polymer are connected to said SH—group of said linker Z, which linker Z is comprised by the inventive compounds, and preferably by the inventive compounds of formula (I) or (II), the remaining amino functions being capped. Preferably the loading of the polymer is 20-70%, more preferably 30-60%. Further preferred polymers in said context are polymers with loading of one or several of compounds of formula (I) or (II), wherein said compounds of formula (I) or (II) are selected from 4*, 9*, 13*, 17*, 21*, 25*, 29* or 33*, and 46*-60*.

The polymers of the present invention which comprises the inventive compounds comprising a carbohydrate moieties and linkers Z, wherein said carbohydrate moieties mimic glycoepitopes comprised by glycosphingolipids of the nervous system allow straightforward coupling of said carbohydrate moieties such as ganglioside glycoepitopes to biodegradable poly-L-lysine and other functionalized biodegradable polymers without loosing the integrity of the carbohydrate moieties at their reducing end. This is in particular important since the monosaccharide with the reducing end comprised the carbohydrate moieties can also contribute to binding affinity to antibodies or other targets, and thus chemical linkage methods that leave this carbohydrate ring intact are preferable. Thus, the resulting inventive chemically defined glycoconjugates/glycopolymers based on biodegradable polymer backbones can be used in a clinical context, either therapeutic and diagnostic, to detect or neutralize pathogenic anti-glycan antibodies. Moreover, the multivalent presentation of the carbohydrate moieties mimicking glycoepitopes comprised by glycosphingolipids of the nervous system, on, preferably, poly-L-lysine, can substantially increase their binding affinity towards binding partners.

In a particularly preferred embodiment, the invention relates to polymers comprising a multitude of compounds of formula (I), and/or (II) wherein the polymer is poly-L-lysine and wherein said polymer further comprises said linker Z connecting said compounds to the polymer backbone. Poly-L-lysine is biodegradable and therefore in particular suitable for therapeutical application.

The compounds of the invention have valuable pharmacological properties. The invention also relates to compounds as defined hereinbefore for use as medicaments. A compound according to the invention shows prophylactic and therapeutic efficacy especially against neurological diseases associated with anti-glycan antibodies, particularly immune-mediated neuropathies.

One or multiple compounds of formula (I), and/or (II) or polymers comprising these, can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents.

Therapeutic agents for possible combination are especially immunosuppressive agents/therapies. Examples are purine analogues such as fludarabine and/or cladribine, plasmapheresis, intravenous immunoglobulins, furthermore the chimeric monoclonal antibody rituximab (M. C. Dalakas, Curr Treat Opinions Neurol, 2010, 12, 71-83).

In another particular embodiment, the invention relates to the use of the compounds of the invention in a diagnostic assay for neurological diseases, particularly immune-mediated neuropathies. In particular, the invention relates to kits comprising the compounds of formula (I), and/or (II) as defined above, and also polymers of the invention comprising such compounds as substituents.

The present invention relates to a method of diagnosis of neurological diseases, particularly immune-mediated neuropathies, wherein the level of antibodies (e.g. IgM/IgG) against glycans of the nervous system, particularly glycolipids, is determined in a body fluid sample, e.g. serum, and a high level is indicative of the development and the severity of a particular neurological condition.

Other body fluids than serum are useful for determination of antibodies against glycosphingolipid glycoepitopes and are, e.g., whole blood, cerebrospinal fluid or extracts from solid tissue.

Any known method may be used for the determination of the level of antibodies against glycosphingolipid glycoepitopes in body fluids. Methods considered are, e.g., ELISA, RIA, EIA, or microarray analysis.

A preferred method for the determination of antibodies against glycosphingolipid glycoepitopes in human body fluids, e.g. in serum, is an ELISA. In such an embodiment, microtiter plates are coated with compounds of formula (I), and/or (II) or preferably polymers of the invention comprising such compounds as substituents. The plates are then blocked and the sample or a standard solution is loaded. After incubation, an anti-IgM/IgG antibody is applied, e.g. an anti-IgM or anti-IgG antibody directly conjugated with a suitable label, e.g. with an enzyme for chromogenic detection. Alternatively, a polyclonal rabbit (or mouse) anti-IgM/anti-IgG antibody is added. A second antibody detecting the particular type of the anti-IgM/anti-IgG antibody, e.g. an anti-rabbit (or anti-mouse) antibody, conjugated with a suitable label, e.g. the enzyme for chromogenic detection as above, is then added. Finally the plate is developed with a substrate for the label in order to detect and quantify the label, being a measure for the presence and amount of antibodies against glycosphingolipid glycoepitopes of the nervous system. If the label is an enzyme for chromogenic detection, the substrate is a colour-generating substrate of the conjugated enzyme. The colour reaction is then detected in a microplate reader and compared to standards.

It is also possible to use antibody fragments. Suitable labels are chromogenic labels, i.e. enzymes which can be used to convert a substrate to a detectable colored or fluorescent compound, spectroscopic labels, e.g. fluorescent labels or labels presenting a visible color, affinity labels which may be developed by a further compound specific for the label and allowing easy detection and quantification, or any other label used in standard ELISA.

Other preferred methods of detection of antibodies against glycosphingolipid glycoepitopes are radioimmunoassay or competitive immunoassay and chemiluminescence detection on automated commercial analytical robots. Microparticle enhanced fluorescence, fluorescence polarized methodologies, or mass spectrometry may also be used. Detection devices, e.g. microarrays, are useful components as readout systems for antibodies against glycosphingolipid glycoepitopes.

In a further embodiment the invention relates to a kit suitable for an assay as described above, in particular an ELISA, comprising compounds of formula (I), and/or (II) or polymers comprising such compounds as substituents. The kits further contain anti-IgM/anti-IgG antibodies (or anti-IgM/IgG antibody fragments) carrying a suitable label, or anti-IgM/anti-IgG antibodies and second antibodies carrying such a suitable label, and reagents or equipment to detect the label, e.g. reagents reacting with enzymes used as labels and indicating the presence of such a label by a colour formation or fluorescence, standard equipment, such as microtiter plates, pipettes and the like, standard solutions and wash solutions.

The ELISA can be also designed in a way that patient blood or serum samples are used for the coating of microtiter plates with the subsequent detection of anti-glycan antibodies with labelled compounds of formula (I), and/or (II) or labelled polymers comprising such compounds as substituents. The label is either directly detectable or indirectly detectable via an antibody.

The polymer carrying compounds of formula (I), and/or (II) of the invention binds to the pathogenic anti-glycan antibodies and potentially downregulates the anti-glycan IgM or IgG antibody production. It allows an antigen-specific treatment for neurological diseases involving anti-glycan antibodies against glycosphingolipid glycoepitopes.

Furthermore the invention relates to a pharmaceutical composition comprising a compound of formula (I), and/or (II) or a polymer carrying compounds of formula (I), and/or (II) of the invention.

Pharmaceutical compositions for parenteral administration, such as subcutaneous, intravenous, intrahepatic or intramuscular administration, to warm-blooded animals, especially humans, are considered. The compositions comprise the active ingredient(s) alone or, preferably, together with a pharmaceutically acceptable carrier. The dosage of the active ingredient(s) depends upon the age, weight, and individual condition of the patient, the individual pharmacokinetic data, and the mode of administration.

For parenteral administration preference is given to the use of suspensions or dispersions of the carbohydrate polymer of the invention, especially isotonic aqueous dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

Suitable carriers for enteral administration, such as nasal, buccal, rectal or oral administration, are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient(s).

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

The mentioned pharmaceutical compositions according to the invention may contain separate tablets, granules or other forms of orally acceptable formulation of the active ingredients, or may contain a mixture of active ingredients in one suitable pharmaceutical dosage form, as described above. In particular the separate orally acceptable formulations or the mixture in one suitable pharmaceutical dosage form may be slow release and controlled release pharmaceutical compositions.

The pharmaceutical compositions comprise from approximately 1% to approximately 95% active ingredient or mixture of active ingredients, single-dose administration forms comprising in the preferred embodiment from approximately 20% to approximately 90% active ingredient(s) and forms that are not of single-dose type comprising in the preferred embodiment from approximately 5% to approximately 20% active ingredient(s).

The invention also relates to the mentioned pharmaceutical compositions as medicaments in the treatment of neurological diseases associated with anti-glycan antibodies, particularly immune-mediated neuropathies.

The present invention relates furthermore to a method of treatment of neurological diseases associated with anti-glycan antibodies, particularly immune-mediated neuropathies, which comprises administering a composition according to the invention in a quantity effective against said disease, to a warm-blooded animal requiring such treatment. The pharmaceutical compositions can be administered prophylactically or therapeutically, preferably in an amount effective against the said diseases, to a warm-blooded animal, for example a human, requiring such treatment. In the case of an individual having a bodyweight of about 70 kg the daily, weekly or monthly dose administered is from approximately 0.01 g to approximately 5 g, preferably from approximately 0.1 g to approximately 1.5 g, of the active ingredients in a composition of the present invention.

The following Examples serve to illustrate the invention without limiting the invention in its scope.

EXAMPLES

General Methods

NMR spectra were obtained on a Bruker Avance DMX-500 (500 MHz) spectrometer. Assignment of $^1$H and $^{13}$C NMR spectra was achieved using 2D methods (COSY, HSQC and HMBC). Chemical shifts are expressed in ppm using residual CHCl$_3$, CHD$_2$OD, DMSO-d$_6$ or HDO as references. IR spectra were recorded using a Perkin-Elmer Spectrum One FT-IR spectrometer. Electron spray ionization mass spectra (ESI-MS) were obtained on a Waters micromass ZQ. HRMS analysis was carried using an Agilent 1100LC equipped with a photodiode array detector and a micromass QTOF I equipped with a 4 GHz digital-time converter. Reactions were monitored by ESI-MS and TLC using glass plates coated with silica gel 60 F$_{254}$ (Merck) and visualized by using UV light and/or by charring with mostain (a 0.02 M solution of ammonium cerium sulfate dihydrate and ammonium molybdate tetrahydrate in 10% aq H$_2$SO$_4$). Column chromatography was performed on silica gel (Redisep normal phase silica gel column 35/70) or RP-18 (Merck LiChroprep® RP-18 40/63). Dichloromethane (DCM) and MeOH were dried by filtration over Al$_2$O$_3$ (Fluka, type 5016A basic). Dimethylformamide (DMF) was purchased from Acros (99.8%, extra dry, over molecular sieves). Molecular sieves (MS, 4 Å) were activated in vacuo at 400° C. for 30 min immediately before use. Size-exclusion chromatography was performed on polyacrylamide gel (Biogel P-2 Fine). Dialysis was performed on a Biotech Cellulose Ester (CE) Membrane (SpectrumLabs, molecular weight cutoff: 100-500 Da). Centrifugations were carried out with an Eppendorf Centrifuge 5804 R. rt=room temperature.

Seventeen glycopolymers were synthesized (6, Scheme 1; 10, Scheme 2; 14, Scheme 3; 18, Scheme 4; 22, Scheme 5; 26, Scheme 6; 30, Scheme 7; 34, Scheme 8; 38, Scheme 9; 42, Scheme 10; 45, Scheme 11; 78, Scheme 16; 86, Scheme 18; 89, Scheme 19; 93, Scheme 20; 100, Scheme 22; 102, Scheme 23) for biological evaluation. Polylysine glycoconjugates 6, 10, 14, 18, 22, 26, 30, 34 all bear the same linker but differ by their carbohydrate moiety (respectively GM1a, GM1b, asialo GM1, GM2, GD1a, GD1b, GD3 and GT1a). Polylysine glycoconjugates 6, 38, 42 and 45 bear the same carbohydrate (GM1a) but differ by their linker moiety. Polylysine glycoconjugate 78 bears a GM4 mimetic. Polylysine glycoconjugate 86 bears the HO$_3$S-β-D-GlcpA-(1→3)-β-D-Galp (HNK-1) disaccharide. The above-mentioned glycoconjugates (6, 10, 14, 18, 22, 26, 30, 34, 38, 45, 78, 86) are all poly-L-lysine conjugates. Conjugates 89 and 93 bear the same HNK-1 disaccharide but differ by their polymer backbones (poly-L-lysine dendrimer and poly-L-ornithine respectively). Conjugates 100 and 102 bear the same lactose disaccharide but differ by their polymer backbones (chitosan and poly-L-glutamic acid respectively). The synthesis of the HNK-1 disaccharide 58 functionalized by linker5 72 is described in Scheme 17. The synthesis of the lactose disaccharide 56 functionalized by linker5 72 is described in Scheme 121. The synthesis of linkers 35, 39, 43 and 72 is described in Scheme 12, 13, 14 and 15 respectively.

All reagents were bought from Sigma Aldrich, Acros, Alfa-Aesar, Elicityl or Alamanda Polymers. Linker 2 and compound 66 were synthesized according to a published procedure (O. Bohorov, et al. *Glycobiology*, 2006, 16, 21C-27C). Chloroacetylated poly-L-lysine 5 (250 lysine repeating units) was synthesized from commercial poly-L-lysine polymer according to a published procedure (G. Thoma et al., *J Am Chem Soc* 1999, 121, 5919-5929). Derivatives 68, 73, 74, 80, 87 and 98 were synthesized according to published procedures (respectively I. Ueda, et al. *Chem Pharm Bull* (Tokyo), 1990, 38, 3035-3041; M. Numata, et al. *Carbohydr Res*, 1987, 163, 209-225; J. L. Magnani, Preparation of oligosaccharide glycomimetic antagonists as E- and P-selectin modulators, WO 2005054264A2, Jun. 16, 2005; T. Furukawa, *Tetrahedron Lett*, 2011, 52, 5567-5570; K. T. Al-Jamal, et al. *J Drug Target*, 2006, 14, 405-412; T. Kojima, Chitosan or chitin derivative and method for processing silver halide photographic material by using the same, US 005155004A, Oct. 13, 1992).

Scheme 1: Synthesis of the GM1a polymer 6

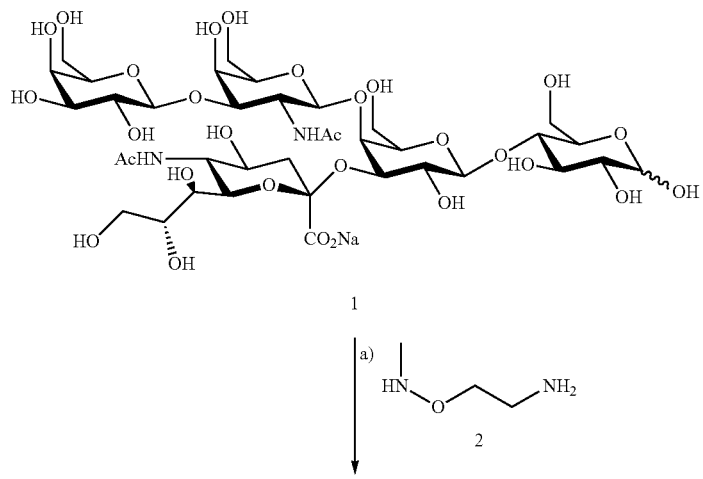

-continued
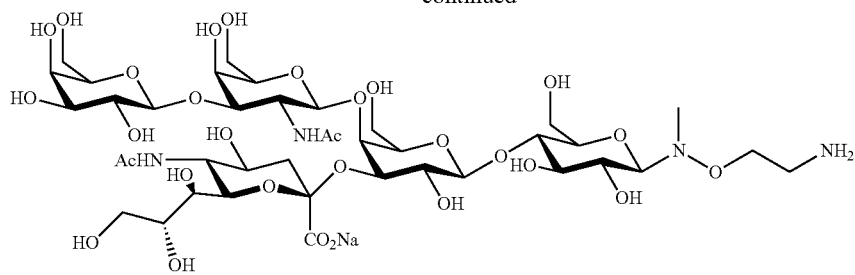
3
b)
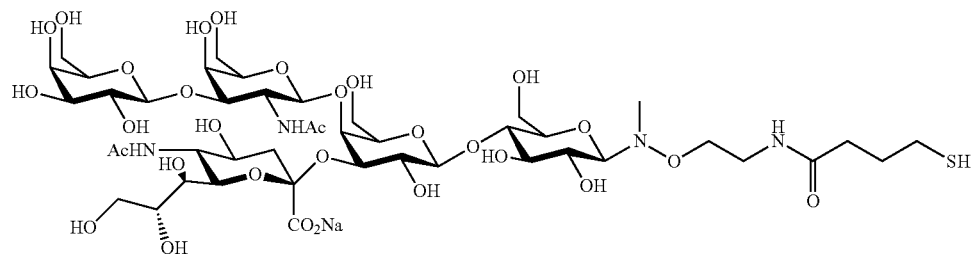
4 [GM1a—N(Me)O(CH$_2$)$_2$NHC(O)(CH$_2$)$_3$SH]
c)
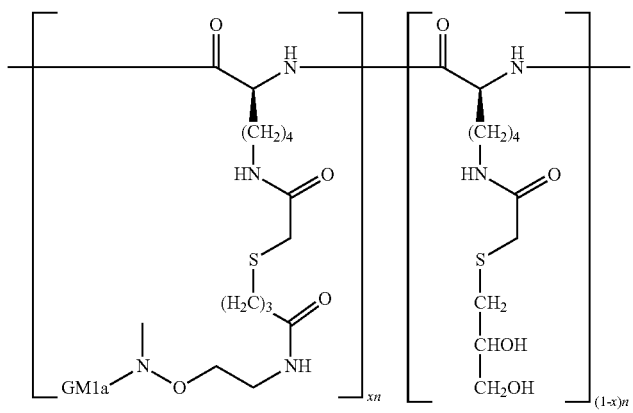
5
6
Reagents and conditions: a) 2, sodium acetate buffer, 91%; b) DL-dithiothreitol, γ-thiobutyrolactone, Et$_3$N, DMF, 54%; c) i. 5, DBU, DMF/H$_2$O; ii. thioglycerol, Et$_3$N, 84%

N-(N-Methyl-O-[2-aminoethyl]hydroxylamino)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (3)

To a solution of hemiacetal 1 (5.0 mg, 4.90 μmol) in NaOAc/AcOH buffer (0.1 M, pH 4.5, 50 μL) was added oxyamine 2 (4.4 mg, 49 μmol, 10 equiv). The reaction mixture was stirred for 24-48 h at 25-40° C. Purification by dialysis gave compound 3 (4.97 mg, 4.55 μmol, 91%) as a white fluffy solid.

$^1$H-NMR (500 MHz, $D_2O$): δ4.80 (d, 1H), 4.57 (d, 1H), 4.57 (d, 1H), 4.24 (d, 1H), 4.22-4.11 (m, 2H), 4.06 (dd, 1H), 4.04-3.96 (m, 3H), 3.94 (d, 1H), 3.89 (dd, 1H), 3.86-3.74 (m, 12H), 3.73-3.57 (m, 10H), 3.54 (dd, 1H), 3.52 (dd, 1H), 3.39 (dd, 1H), 3.28-3.26 (m, 2H), 2.81 (s, 3H), 2.68 (dd, 1H), 2.05, 2.03 (2s, 6H), 1.94 (t, 1H).

HRMS ($ESI^+$): m/z 1071.4132 (calc for $C_{40}H_{71}N_4O_{29}^+$ $[M+H]^+$: m/z 1071.4198).

N-(N-Methyl-O-[2-mercaptobutanamido)ethyl]hydroxylamino)-β-D-galactopyranosyl-(1→3)-2-acetamido-β-D-galactopyranosyl-(1→4)-[5-acetyl-β-neuraminic acid-(2→3)-β-D-galacto-pyranosyl-(1→4)]-β-D-glucopyranoside (4)

To a suspension of amine 3 (4.97 mg, 4.55 μmol) in anhyd DMF (90 μL) were successively added DL-dithiothreitol (1.2 mg, 8.2 mol, 1.8 equiv), γ-thiobutyrolactone (3.9 μL, 46 μmol, 10 equiv) and $Et_3N$ (6.3 μL, 46 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 4 (2.8 mg, 2.33 μmol, 54%) as a white fluffy solid.

$^1$H-NMR (500 MHz, $D_2O$): δ4.79 (d, 1H), 4.56 (m, 2H), 4.22-3.31 (m, 32H), 2.75 (s, 3H), 2.68 (m, 1H), 2.57 (t, 2H), 2.41 (t, 2H), 2.05, 2.03 (2s, 6H), 1.91 (m, 3H).

MS ($ESI^-$): m/z 1171.59 (calc for $C_{44}H_{75}N_4O_{30}S^-$ $[M-Na]^-$: m/z 1171.42).

GM1a Polymer (6)

To a solution of 5 (1.2 mg, 5.83 μmol) in DMF (60 μL) were subsequently added compound 4 (2.8 mg, 2.33 μmol, 0.4 equiv), water (3 μL) and a solution of DBU (1.3 μL, 8.74 μmol, 1.5 equiv) in DMF (10 μL). After stirring for 1-24 h at rt, thioglycerol (1.5 μL, 17.5 μmol, 3.0 equiv) and $Et_3N$ (2.4 μL, 17.5 μmol, 3.0 equiv) were added. The reaction mixture was stirred at rt for another 12-24 h. The product was precipitated by slow addition to a stirring solution of $EtOH/Et_2O$ (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM1a polymer 6 (2.88 mg, 84%) as a white solid. According to $^1$H NMR, the product contained approximately 28% of the lysine side-chains substituted by the carbohydrate epitope 4.

In this particular embodiment, the GM1a epitope 4 carrying the linker Z with the terminal sulfhydryl function was synthesized and reacted in a substochiometric amount with the activated (chloroacetylated) lysine polymer 5. The carbohydrate loading (28%) of the obtained glycopolymer 6 was determined by $^1$H NMR. The starting polylysine hydrobromide had an average molecular weight (MVV) of 52 kDa (250 repeating lysine units), whereas the final polymer 6 with 28% GM1a epitope loading had a calculated average MW of 145 kDa.

Scheme 2: Synthesis of the GM1b polymer 10

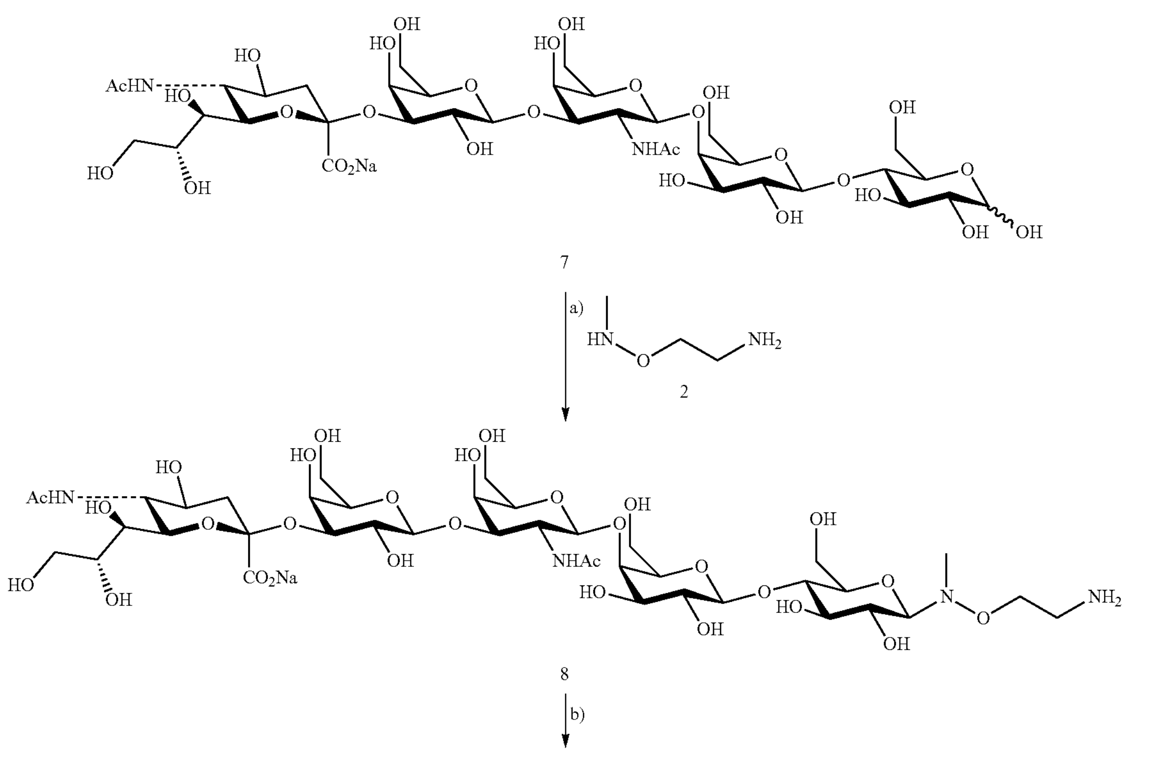

-continued

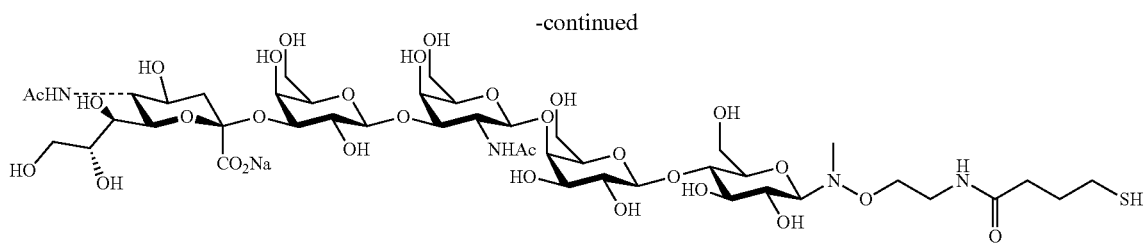

9 [GM 1b-N(Me)O(CH$_2$)$_2$NHC(O)(CH$_2$)$_3$SH]

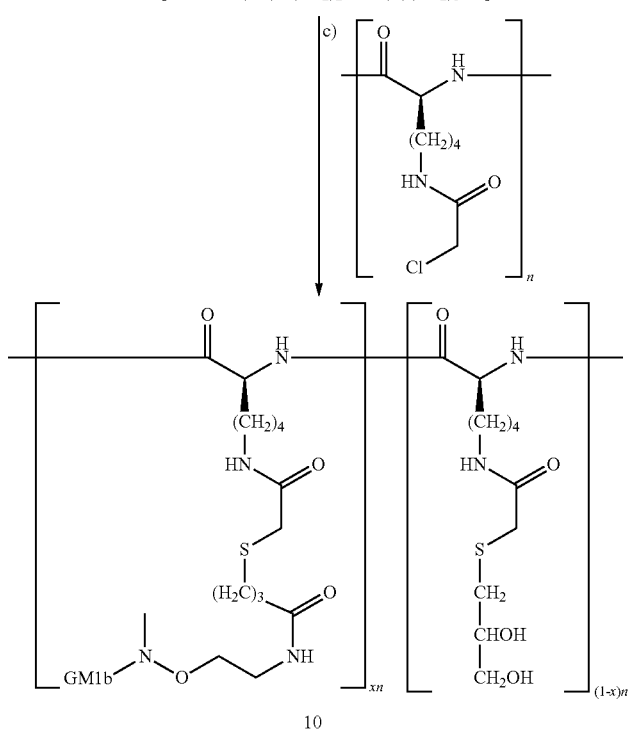

Reagents and conditions: a) 2, sodium acetate buffer, 71%; b) DL-dithiothreirol, γ-thiobutyrolactone, Et$_3$N, DMF, 65%; c) i. 5, DBU, DMF/ H$_2$O; ii. thioglycerol, Et$_3$N, 61%

N-(N-Methyl-O-[2-aminoethyl]hydroxylamino)-5-acetyl-α-neuraminic acid-(2→3)-2→3-D-galactopyranosyl-(1→3)-2-acetamido-β-D-galactopyranosyl-(1→4)-β-D-galactopyranosyl-(1→4)-β-D-glucopyranoside (8)

To a solution of hemiacetal 7 (10 mg, 9.80 μmol) in NaOAc/AcOH buffer (0.1 M, pH 4.5, 98 μL) was added oxyamine 2 (8.8 mg, 98.0 μmol, 10 equiv). The reaction mixture was stirred for 24-48 h at 25-40° C. Purification by dialysis gave compound 8 (7.6 mg, 6.95 μmol, 71%) as a white fluffy solid.

$^1$H-NMR (500 MHz, D$_2$O): δ4.72 (d, 1H), 4.54 (d, 1H), 4.46 (d, 1H), 4.24 (d, 1H), 4.17 (d, 1H), 4.13 (d, 1H), 4.09 (dd, 1H), 4.06-3.97 (m, 4H), 3.95 (d, 1H), 3.91 (dd, 1H), 3.89-3.81 (m, 7H), 3.81-3.60 (m, 12H), 3.78 (dd, 1H), 3.62-3.57 (m, 1H), 3.59 (dd, 1H), 3.57 (dd, 1H), 3.44 (dd, 1H), 3.29-3.27 (m, 2H), 2.81 (s, 3H), 2.77 (dd, 1H), 2.06, 2.05 (2s, 6H), 1.81 (dd, 1H).

MS (ESI$^-$): m/z 1069.62 (calc for C$_{40}$H$_{69}$N$_4$O$_{29}$$^-$[M−Na]$^{-1}$: m/z 1069.41).

N-(N-Methyl-O-[2-(2-mercaptobutanamido)ethyl]hydroxylamino)-5-acetyl-α-neuraminic acid-(2→3)-β-D-galactopyranosyl-(1→3)-2-acetamido-β-D-galactopyranosyl-(1→4)-β-D-galactopyranosyl-(1→4) β-D-ducopyranoside (9)

To a suspension of amine 8 (7.6 mg, 6.95 μmol) in anhyd DMF (140 μL) were successively added DL-dithiothreitol (spatula tip), γ-thiobutyrolactone (6.0 μL, 69.5 μmol, 10 equiv) and Et$_3$N (9.7 μL, 69.5 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 9 (5.4 mg, 4.52 μmol, 65%) as a white fluffy solid.

$^1$H-NMR (500 MHz, D$_2$O): δ4.72 (d, 1H), 4.54 (d, 1H), 4.47 (d, 1H), 4.19 (d, 1H), 4.17 (d, 1H), 4.13 (d, 1H), 4.09 (dd, 1H), 4.04 (dd, 1H), 4.00 (dd, 1H), 3.96 (d, 1H), 3.93-3.80 (m, 10H), 3.80-3.58 (m, 13H), 3.58-3.52 (m, 1H), 3.56 (dd, 1H), 3.55 (dd, 1H), 3.47-3.40 (m, 1H), 3.44 (dd, 1H), 2.81-2.74 (m, 5H), 2.57 (t, 2H), 2.40 (t, 2H), 2.06, 2.05 (2s, 6H), 1.94-1.89 (m, 2H), 1.81 (dd, 1H).

HRMS (ESI$^-$): m/z 1171.01 (calc for C$_{44}$H$_{75}$N$_4$O$_{30}$S$^+$ [M−Na]$^-$: m/z 1171.42).

GM1b Polymer (10)

To a solution of 5 (1.86 mg, 9.04 µmol) in DMF (60 µL) were subsequently added compound 9 (5.4 mg, 4.52 µmol, 0.5 equiv), water (40 µL) and a solution of DBU (2.0 µL, 13.6 µmol, 1.5 equiv) in DMF (15 µL). After stirring for 1-24 h at rt, thioglycerol (2.3 µL, 27.1 µmol, 3.0 equiv) and Et₃N (3.8 µL, 27.1 µmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM1b polymer 10 (4.2 mg, 61%) as a white solid. According to ¹H NMR, the product contained approximately 45% of the lysine side-chains substituted by the carbohydrate epitope 9.

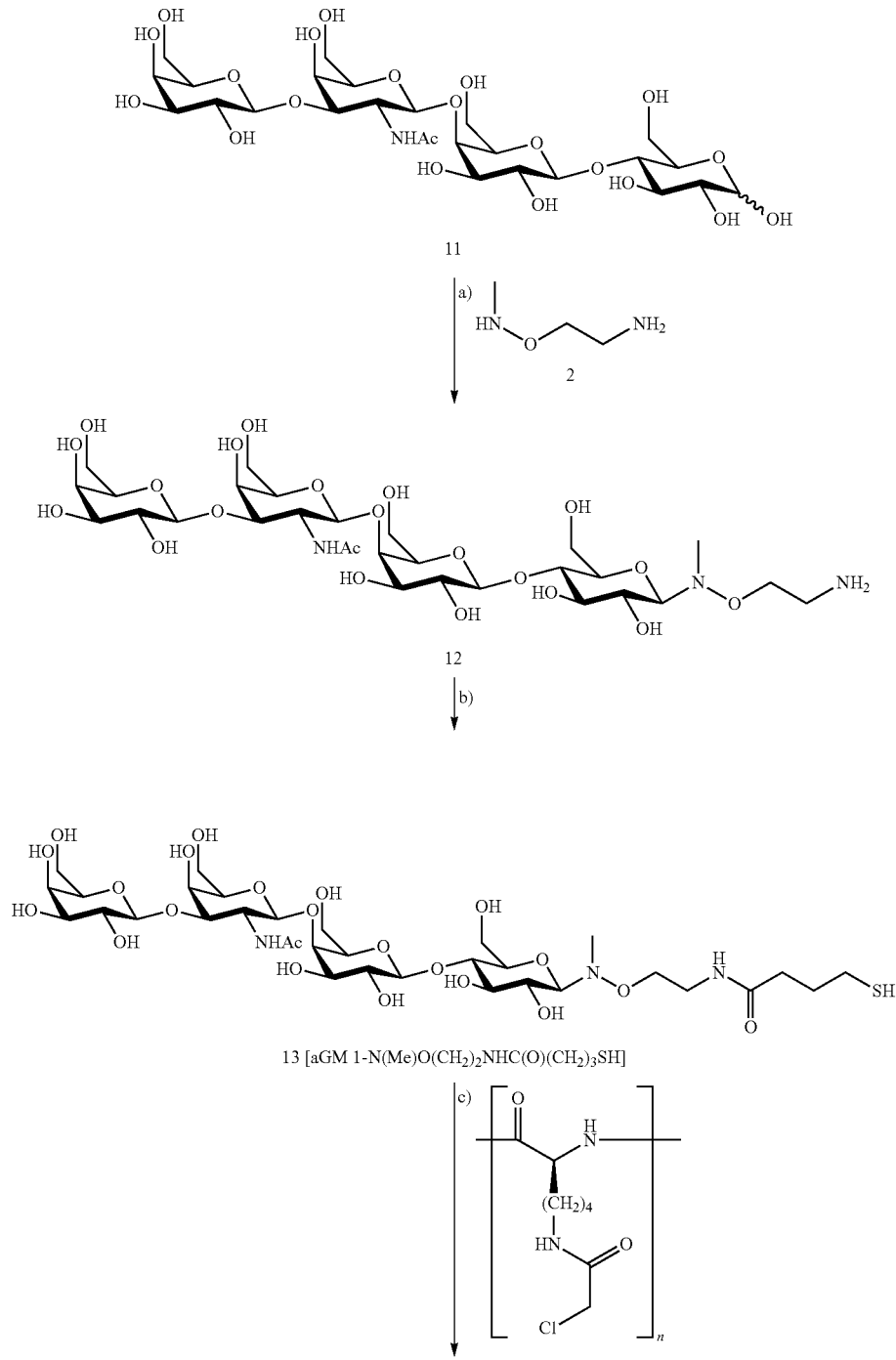

Scheme 3: Synthesis of the asialo GM1 polymer 14

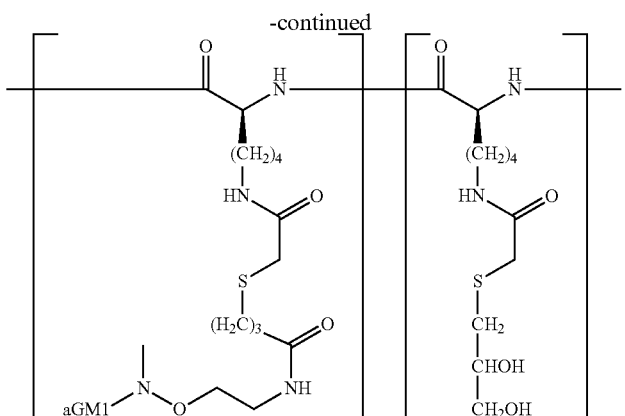

Reagents and conditions: a) 2, sodium acetate buffer, quant; b) DL-dithiothreitol, γ-thiobutyrolactone, Et₃N, DMF, 80%; c) i. 5, DBU, DMF/ H₂O; ii. thioglycerol, Et₃N, 71%

N-(N-Methyl-O-[2-aminoethyl]hydroxylamino)-β-D-galactopyranosyl-(1→)-2-acetamido-β-D-galactopyranosyl-(1→4)-β-D-galactopyranosyl-(1→4)-β-D-glucopyranoside (12)

To a solution of hemiacetal 11 (10.0 mg, 14.1 μmol) in NaOAc/AcOH buffer (0.1 M, pH 4.5, 141 μL) was added oxyamine 2 (12.7 mg, 141 μmol, 10 equiv). The reaction mixture was stirred for 24-48 h at 25-40° C. Purification by P2 size-exclusion chromatography gave compound 12 (10.9 mg, 14.0 μmol, quant) as a white fluffy solid.

$^1$H-NMR (500 MHz, D$_2$O): δ4.71 (d, 1H), 4.47 (d, 1H), 4.46 (d, 1H), 4.24 (d, 1H), 4.18 (d, 1H), 4.13 (d, 1H), 4.06-4.00 (m, 3H), 4.04 (dd, 1H), 3.93 (d, 1H), 3.90 (dd, 1H), 3.87-3.75 (m, 8H), 3.76-3.65 (m, 4H), 3.64 (dd, 1H), 3.61-3.58 (m, 2H), 3.60 (dd, 1H), 3.55 (dd, 1H), 3.43 (dd, 1H), 3.28 (t, 2H), 2.81 (s, 3H), 2.06 (s, 3H).

MS (ESI$^+$): m/z 780.46 (calc for C$_{29}$H$_{54}$N$_3$O$_{21}$$^+$[M+H]$^+$: m/z 780.32).

N-(N-Methyl-O-[2-(2-mercaptobutanamido)ethyl]hydroxylamino)-β-D-galactopyranosyl-(1→3)-2-acetamido-β-D-galactopyranosyl-(1→4)-β-D-galactopyranosyl-(1→4)-β-D-glucopyranoside (13)

To a suspension of amine 12 (11 mg, 14.1 μmol) in anhyd DMF (282 μL) were successively added DL-dithiothreitol (tip of spatula), γ-thiobutyrolactone (12.2 μL, 141 μmol, 10 equiv) and Et$_3$N (19.7 μL, 141 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 13 (10.0 mg, 11.3 μmol, 80%) as a white fluffy solid.

$^1$H-NMR (500 MHz, D$_2$O): δ4.72 (d, 1H), 4.47 (d, 2H), 4.19 (d, 1H), 4.19-4.16 (m, 1H), 4.14-4.11 (m, 1H), 4.04 (dd, 1H), 4.01-3.97 (m, 1H), 3.94-3.91 (m, 1H), 3.92-3.85 (m, 3H), 3.85-3.71 (m, 8H), 3.76-3.63 (m, 4H), 3.64 (dd, 1H), 3.60 (dd, 1H), 3.57-3.52 (m, 3H), 3.46-3.38 (m, 3H), 2.78-2.75 (m, 2H), 2.76 (s, 3H), 2.40 (t, 2H), 2.06 (s, 3H), 2.03-2.00 (m, 2H).

MS (ESI$^+$: m/z 904.05 (calc for C$_{33}$H$_{59}$N$_3$O$_{22}$SNa$^+$ [M+Na]$^+$: m/z 904.32).

Asialo GM1 Polymer (14)

To a solution of 5 (1.3 mg, 6.25 μmol) in DMF (60 μL) were subsequently added compound 13 (3.7 mg, 4.19 μmol, 0.4 equiv), water (5 μL) and a solution of DBU (2.3 μL, 15.7 μmol, 1.5 equiv) in DMF (105 μL). After stirring for 1-24 h at rt, thioglycerol (2.7 μL, 31.4 μmol, 3.0 equiv) and Et$_3$N (4.4 μL, 31.4 μmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave the asialo GM1 polymer 14 (4.6 mg, 71%) as a white solid. According to $^1$H NMR, the product contained approximately 44% of the lysine side-chains substituted by the carbohydrate epitope 13.

Scheme 4: Synthesis of the GM2 polymer 18
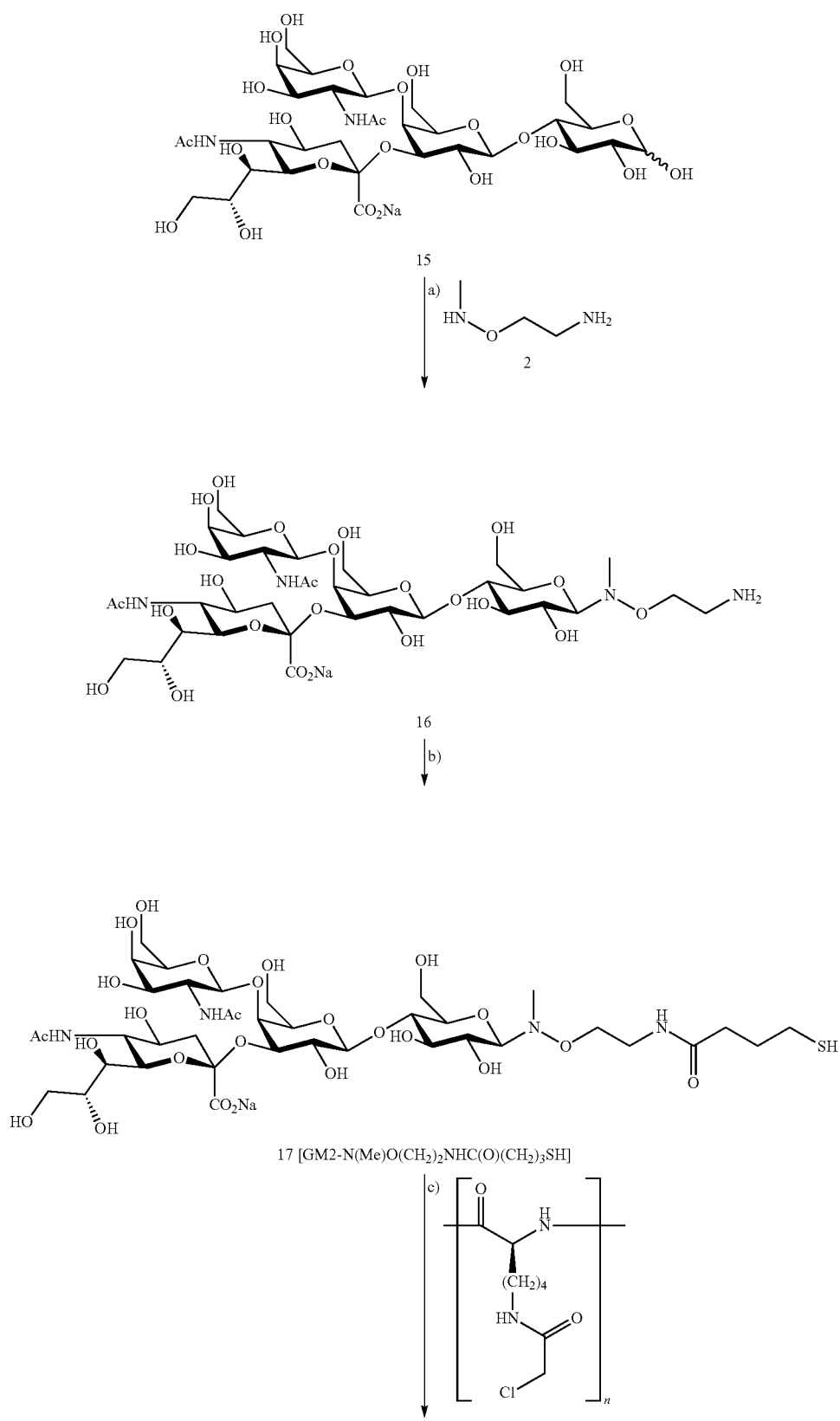

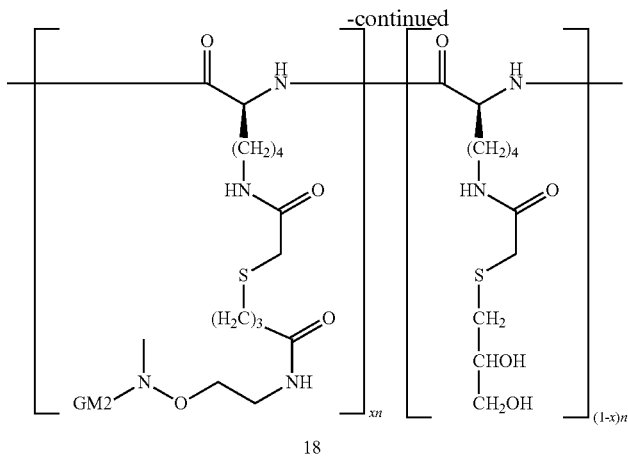

18

Reagents and conditions: a) 2, sodium acetate buffer, 76%; b) DL-Dithiothreitol, γ-thiobutyrolactone, Et₃N, DMF, 52%; c) i. 5, DBU, DMF/H₂O; ii. thioglycerol, Et₃N, 56%

N-(N-Methyl-O-[2-aminoethyl]hydroxylamino)-2-acetamido-β-D-galactopyranosyl-(1→4)-[5-acetyl-α-neuraminic acid-(2→3)]-β-D-galactopyranosyl-(1→4)-β-D-glucopyranoside (16)

To a solution of hemiacetal 15 (12.0 mg, 14.0 μmol) in NaOAc/AcOH buffer (0.1 M, pH 4.5, 140 μL) was added oxyamine 2 (12.6 mg, 114 μmol, 10 equiv). The reaction mixture was stirred for 24-48 h at 25-40° C. Purification by dialysis gave compound 16 (9.9 mg, 10.6 μmol, 76%) as a white fluffy solid.

$^1$H NMR (500 MHz, D$_2$O) δ4.79 (d, 1H), 4.55 (d, 1H), 4.24 (d, 1H), 4.20-4.09 (m, 2H), 4.04-4.00 (dd 2H), 3.97-3.87 (m, 3H), 3.91-3.68 (m, 14H), 3.66-3.56 (m, 5H), 3.50 (dd, 1H), 3.41-3.34 (t, 1H), 3.31-3.26 (t, 2H), 2.81 (s, 3H), 2.72-2.63 (m, 1H), 2.05 (s, 3H), 2.04 (s, 3H), 2.00-1.88 (m, 1H).

MS (ESI$^-$): m/z 907.56 (calc for $C_{34}H_{59}N_4O_{24}^-$[M−Na]$^-$: m/z 907.35).

N-(N-Methyl-O-[2-(2-mercaptobutanamido)ethyl]hydroxylamino)-2-acetamido-β-D-galacto-pyranosyl-(1→4)-[5-acetyl-α-neuraminic acid-(2→3)]-β-D-galactopyranosyl-(1→4)-β-D-glucopyranoside (17)

To a suspension of amine 16 (9.9 mg, 10.6 μmol) in anhyd DMF (250 μL) were successively added DL-dithiothreitol (tip of spatula), γ-thiobutyrolactone (9.2 μL, 106 μmol, 10 equiv) and Et₃N (14.8 μL, 106 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 17 (5.7 mg, 5.52 μmol, 52%) as a white fluffy solid.

$^1$H-NMR (500 MHz, D$_2$O): δ4.76 (d, 1H), 4.56 (d, 1H), 4.19 (d, 1H), 4.17 (dd, 1H), 4.15 (d, 1H), 4.01 (dd, 1H), 3.94 (d, 1H), 3.94 (dd, 1H), 3.90-3.75 (m, 11H), 3.75-3.60 (m, 5H), 3.62 (dd, 1H), 3.58-3.53 (m, 1H), 3.56 (dd, 1H), 3.50 (dd, 1H), 3.45-3.40 (m, 2H), 3.38 (dd, 1H, H-2$_{Gal}$), 2.77 (s, 3H), 2.68 (dd, 1H), 2.57 (t, 2H), 2.40 (t, 2H), 2.05, 2.04 (2s, 6H), 1.97-1.89 (m, 3H).

MS (ESI$^-$): m/z 1009.54 (calc for $C_{38}H_{65}N_4O_{25}S^+$[M−Na]$^-$: m/z 1009.37).

GM2 Polymer (18)

To a solution of 5 (2.27 mg, 11.04 μmol) in DMF (110 μL) were subsequently added compound 17 (5.7 mg, 5.52 μmol, 0.5 equiv), water (25 μL) and a solution of DBU (2.5 μL, 16.55 μmol, 1.5 equiv) in DMF (22 μL). After stirring for 1-24 h at rt, thioglycerol (2.9 μL, 33.11 μmol, 3.0 equiv) and Et₃N (4.6 μL, 33.11 μmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM2 polymer 18 (4.5 mg, 56%) as a white solid. According to $^1$H NMR, the product contained approximately 49% of the lysine side-chains substituted by the carbohydrate epitope 17.

Scheme 5: Synthesis of the GM1a polymer 22
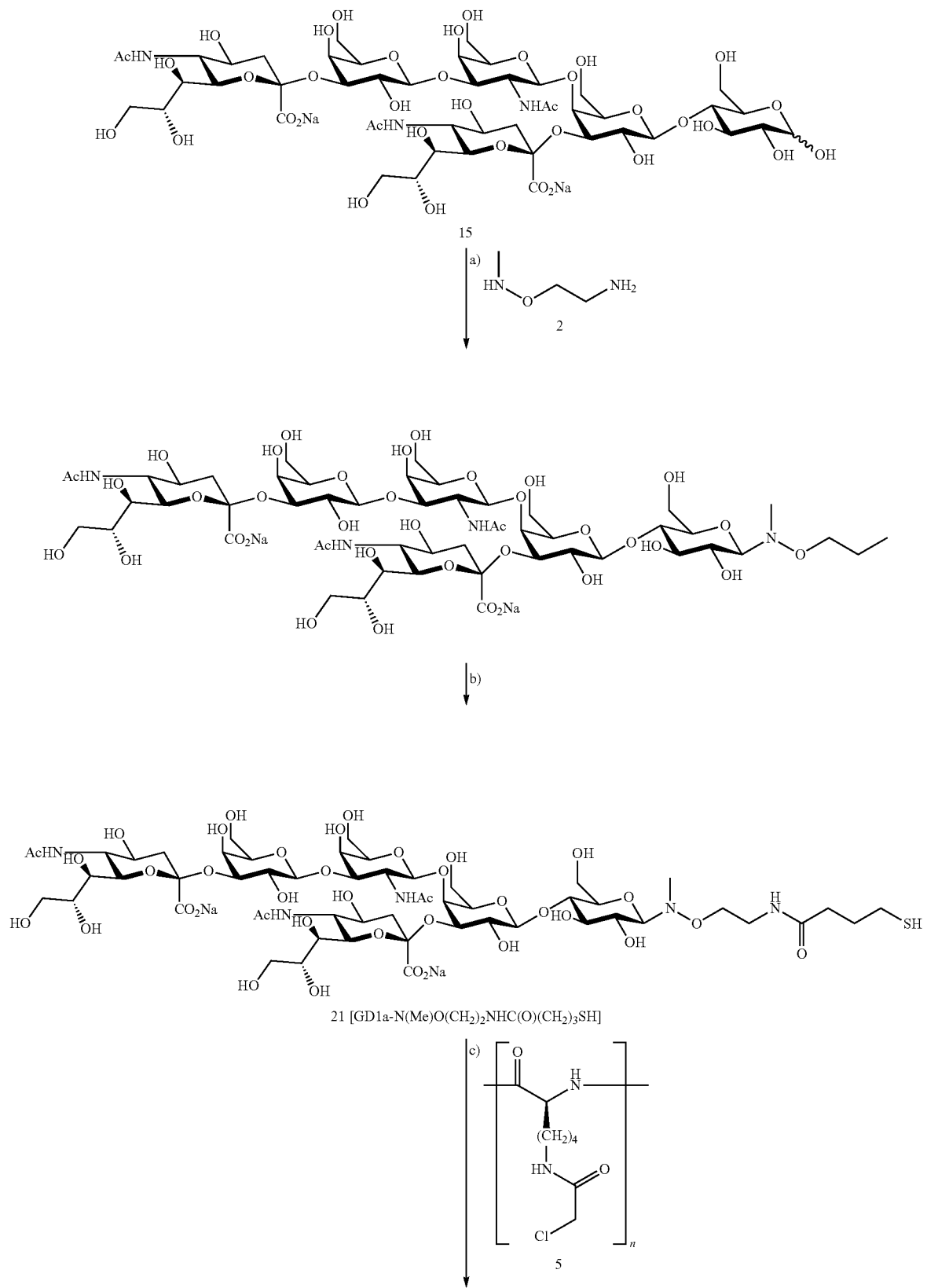

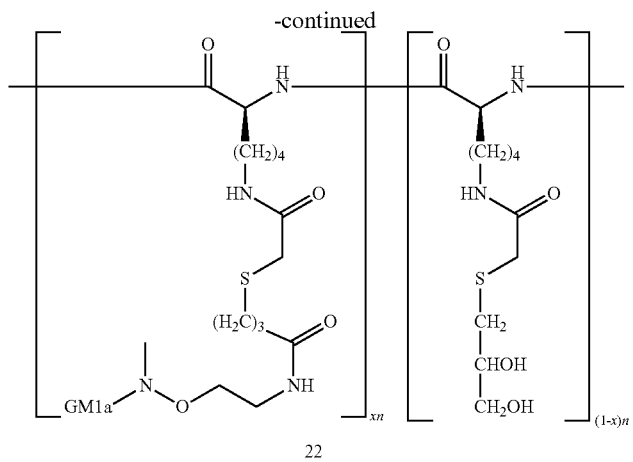

Reagents and conditions: a) 2, sodium acetate buffer, 87%; b) DL-dithiothreitol, γ-thiobutyrolactone, Et₃N, DMF, 78% c) i. 5, DBU, DMF/H₂O; ii. thioglycerol, Et₃N, 59%

N-(N-Methyl-O-[2-aminoethyl]hydroxylamino)-5-acetyl-α-neuraminic acid-(2→3)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (20)

To a solution of hemiacetal 19 (5.0 mg, 3.75 µmol) in NaOAc/AcOH buffer (0.1 M, pH 4.5, 35 µL) was added oxyamine 2 (3.4 mg, 38 µmol, 10 equiv). The reaction mixture was stirred for 24-48 h at 25-40° C. Purification by dialysis gave compound 20 (5.0 mg, admixed with 1.2 equiv of oxyamine 2, 3.27 µmol, corrected yield 87%) as a white fluffy solid.

$^1$H-NMR (500 MHz, D$_2$O): δ4.79 (m, 1H), 4.63 (d, 1H), 4.55 (d, 1H), 4.24 (d, 1H), 4.18 (d, 1H), 4.18-4.14 (m, 1H), 4.15-4.10 (m, 1H), 4.11 (dd, 1H), 4.09-4.05 (m, 2H), 4.06-4.02 (m, 1H), 4.04-3.96 (m, 1H), 3.99-3.95 (m, 1H), 3.93-3.87 (m, 1H), 3.92-3.85 (m, 2H), 3.89-3.80 (m, 2H), 3.87-3.80 (m, 1H), 3.86-3.70 (m, 7H), 3.82-3.52 (m, 12H), 3.67-3.60 (m, 3H), 3.58 (dd, 1H), 3.54 (dd, 1H), 3.41 (dd, 1H), 3.30-3.26 (m, 2H), 2.81 (s, 3H), 2.77 (dd, 1H), 2.70 (dd, 1H), 2.05 (s, 6H), 2.03 (s, 3H), 1.93 (t, 1H), 1.82 (t, 1H).

MS (ESI$^-$): m/z 679.83 (calc for C$_{51}$H$_{85}$N$_5$O$_{37}$$^{2-}$[M−2Na]$^{2-}$: m/z 679.75).

N-(N-Methyl-O-[2-(2-mercaptobutanamido)ethyl] hydroxylamino)-5-acetyl-α-neuraminic acid-(2→3)-β-D-galactopyranosyl-(1→3)-2-acetamido-β-D-galactopyranosyl-(1→4)-[5-acetyl-α-neuraminic acid-(2→3)-β-D-galactopyranosyl-(1→4)]-β-D-glucopyranoside (21)

To a suspension of amine 20 (5.0 mg, 3.27 µmol) in anhyd DMF (65 µL) were successively added DL-dithiothreitol (tip of spatula), γ-thiobutyrolactone (2.8 µL, 32.7 µmol, 10 equiv) and Et₃N (4.6 µL, 32.7 µmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 21 (3.8 mg, 2.52 µmol, 78%) as a white fluffy solid.

$^1$H-NMR (500 MHz, D$_2$O): δ4.79 (m, 1H), 4.63 (d, 1H), 4.56 (d, 1H), 4.19 (d, 1H), 4.18-4.13 (m, 3H), 4.11 (dd, 1H), 4.06 (m, 1H), 4.02-3.96 (m, 1H), 3.97 (d, 1H), 3.94-3.85 (m, 3H), 3.94-3.51 (m, 12H), 3.93-3.84 (m, 2H), 3.88-3.80 (m, 2H), 3.87-3.68 (m, 7H), 3.86-3.81 (m, 1H), 3.68-3.61 (m, 2H), 3.66-3.60 (m, 1H), 3.58-3.54 (m, 1H), 3.56-3.50 (m, 1H), 3.45-3.38 (m, 3H), 2.80-2.75 (m, 1H), 2.77 (s, 3H), 2.70 (dd, 1H), 2.57 (t, 2H), 2.40 (t, 2H), 2.05 (s, 6H), 2.03 (s, 3H), 1.96-1.89 (m, 3H), 1.82 (t, 1H).

MS (ESI$^-$): m/z 730.97 (calc for C$_{55}$H$_{91}$N$_5$O$_{38}$S$^{2-}$[M−2Na]$^{2-}$: m/z 730.75).

GD1a Polymer (22)

To a solution of 5 (1.4 mg, 6.63 µmol) in DMF (67 µL) were subsequently added compound 21 (2.4 mg, 1.59 µmol, 0.4 equiv), water (15 µL) and a solution of DBU (1.5 µL, 9.9 µmol, 1.5 equiv) in DMF (13 µL). After stirring for 1-24 h at rt, thioglycerol (1.7 µL, 19.9 µmol, 3.0 equiv) and Et₃N (2.8 µL, 19.9 µmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GD1a polymer 22 (3.6 mg, 59%) as a white solid. According to $^1$H NMR, the product contained approximately 46% of the lysine side-chains substituted by the carbohydrate epitope 21.

Scheme 6: Synthesis of the GM1b polymer 26
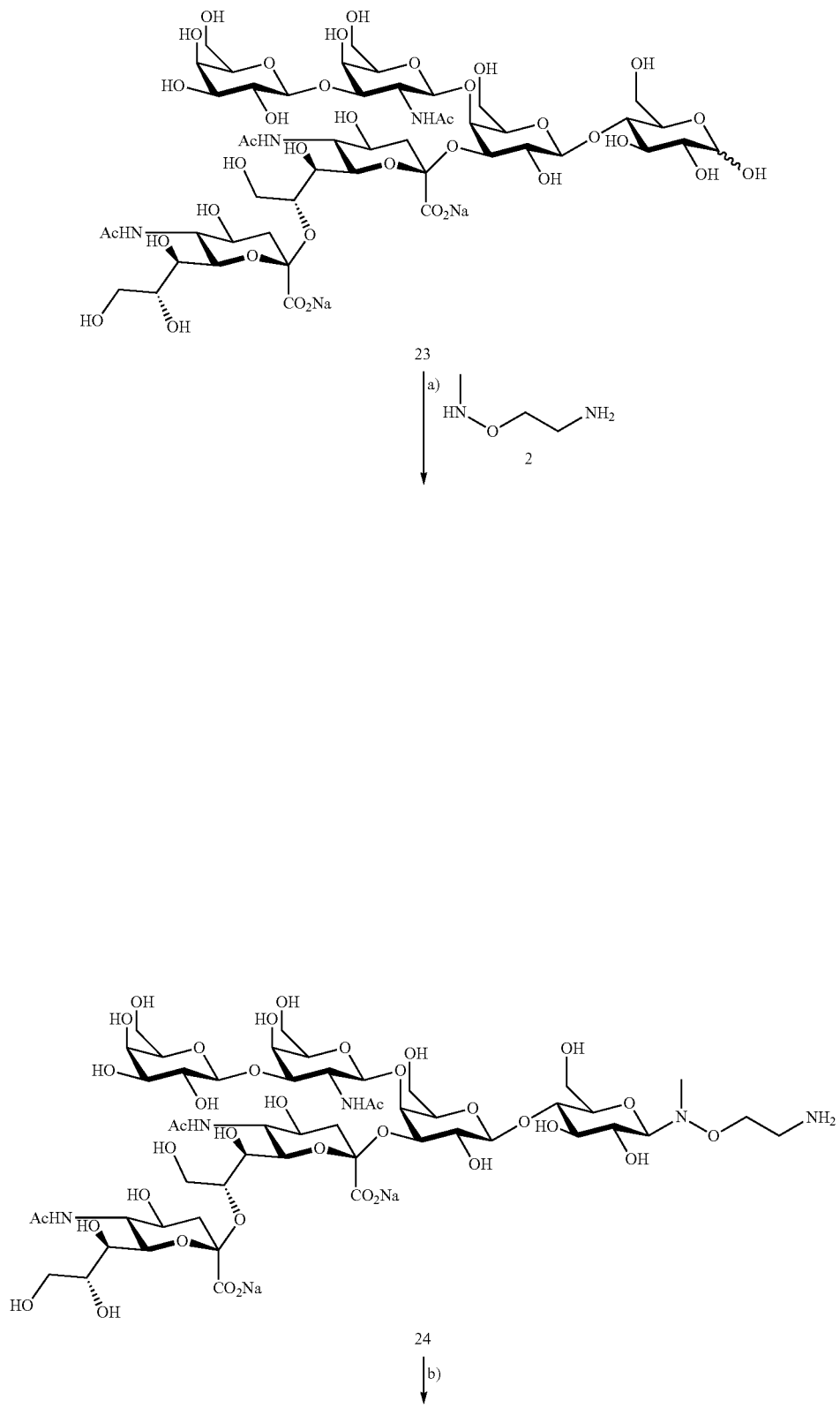

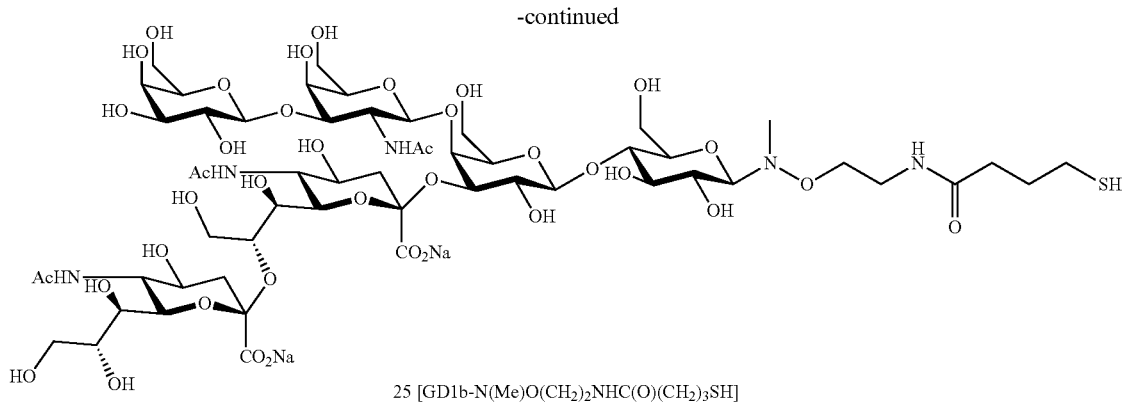

25 [GD1b-N(Me)O(CH$_2$)$_2$NHC(O)(CH$_2$)$_3$SH]

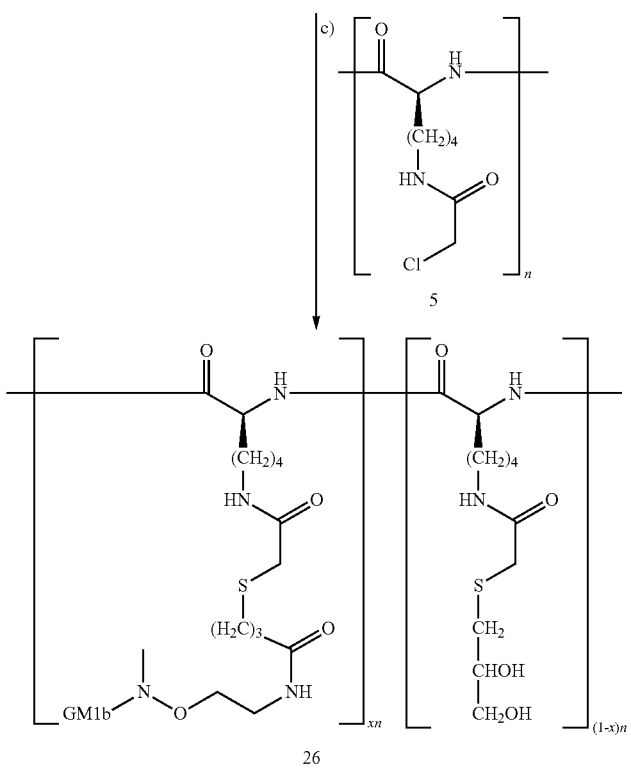

26

Reagents and conditions: a) 2, sodium acetate buffer, 70%; b) DL-dithiothreitol, γ-thiobutyrolactone, Et$_3$N, DMF, 77%; c) i. 5, DBU, DMF/H$_2$O; ii. thioglycerol, Et$_3$N, 40%

N-(N-Methyl-O-[2-aminoethyl]hydroxylamino)-β-D-galactopyranosyl-(1→3)-2-acetamido-β-D-galactopyranosyl-(1→4)-[5-acetyl-α-neuraminic acid-(2→8)-5-acetyl-α-neuraminic acid-(2→3)]-β-D-galactopyranosyl-(1→4)-β-D-glucopyranoside (24)

To a solution of hemiacetal 23 (19.3 mg, 15.0 μmol) in NaOAc/AcOH buffer (0.1 M, pH 4.5, 150 μL) was added oxyamine 2 (313.5 mg, 150 μmol, 10 equiv). The reaction mixture was stirred for 24-48 h at 25-40° C. Purification by dialysis gave compound 24 (14.2 mg, 10.1 μmol, 70%) as a white fluffy solid $^1$H-NMR (500 MHz, D$_2$O): δ4.80 (d, 1H), 4.55-4.53 (t, 2H), 4.23 (d, 1H), 4.21-3.40 (m, 38H), 3.29-3.27 (m, 2H), 2.81 (s, 3H), 2.78-2.69 (m, 2H), 2.09, 2.06, 2.05 (3s, 9H), 1.82-1.73 (m, 2H).

MS (ESI$^-$): m/z 1382.67 (calc for C$_{51}$H$_{85}$N$_5$O$_{37}$$^-$[M−Na]$^-$: m/z 1382.48).

N-(N-Methyl-O-[2-(2-mercaptobutanamido)ethyl] hydroxylamino)-β-D-galactopyranosyl-(1→3)-2-acetamido-β-D-galactopyranosyl-(1→4)-[5-acetyl-α-neuraminic acid-(2→8)-5-acetyl-α-neuraminic acid-(2→3)]-β-D-galactopyranosyl-(1→4)-β-D-glucopyranoside (25)

To a suspension of amine 24 (4.9 mg, 3.51 μmol) in anhyd DMF (70 μL) were successively added DL-dithiothreitol (1.0 mg, 6.31 μmol, 1.8 equiv), γ-thiobutyrolactone (3.0 μL, 35.0 μmol, 10 equiv) and Et$_3$N (4.9 μL, 32.0 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 25 (4.1 mg, 2.72 μmol, 77%) as a white fluffy solid.

$^1$H-NMR (500 MHz, D$_2$O): δ4.79 (d, 1H), 4.55-4.53 (m, 2H), 4.21-3.40 (m, 41H), 2.77 (s, 3H), 2.80-2.67 (m, 4H), 2.41 (t, 2H), 2.09, 2.05 (2s, 11H), 1.84-1.73 (m, 2H).

MS (ESI⁻): m/z 1484.86 (calc for $C_{55}H_{91}N_5O_{38}NaS^-$ [M−Na]⁻: m/z 1484.50).

GD1b Polymer (26)

To a solution of 5 (0.59 mg, 2.89 μmol) in DMF (30 μL) were subsequently added compound 25 (2.1 mg, 1.45 μmol, 0.5 equiv), water (3 μL) and a solution of DBU (0.6 μL, 4.34 μmol, 1.5 equiv) in DMF (6 μL). After stirring for 1-24 h at rt, thioglycerol (0.75 μL, 8.7 μmol, 3.0 equiv) and Et₃N (1.21 μL, 8.7 μmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GD1b polymer 26 (0.68 mg, 40%) as a white solid. According to ¹H NMR, the product contained approximately 20% of the lysine side-chains substituted by the carbohydrate epitope 25.

Scheme 7: Synthesis of the GD3 polymer 30

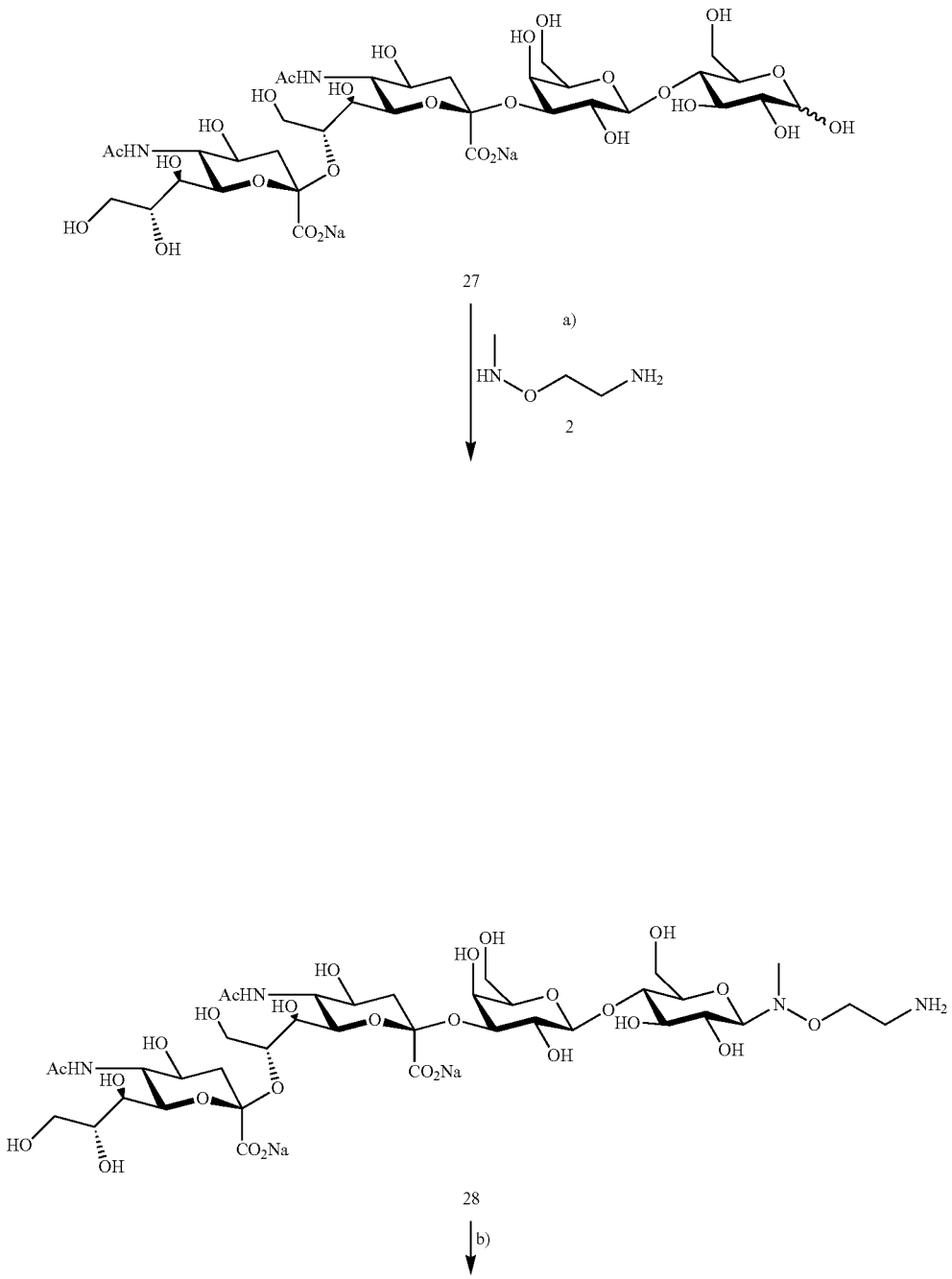

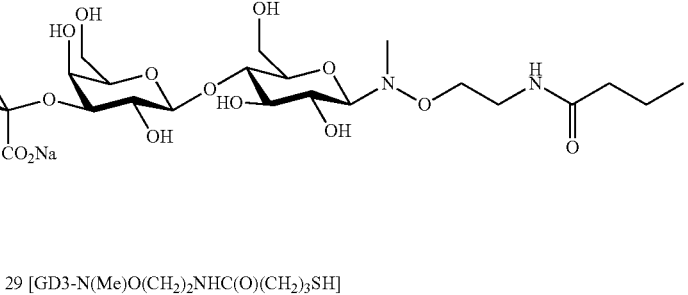

29 [GD3-N(Me)O(CH$_2$)$_2$NHC(O)(CH$_2$)$_3$SH]

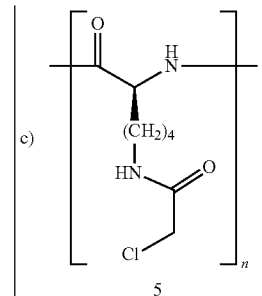

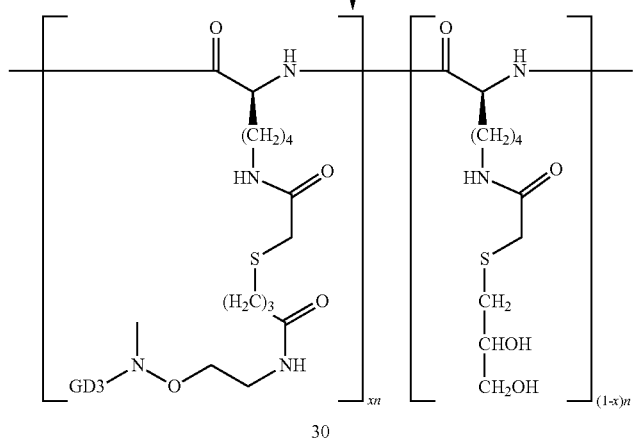

30

Reagents and conditions: a) 2, sodium acetate buffer, 50%; b) DL-dithiothreitol, γ-thiobutyrolactone, Et$_3$N, DMF, 66%; c) i. 5, DBU, DMF/H$_2$O; ii. thioglycerol, Et$_3$N, 18%

N-(N-Methyl-O-[2-aminoethyl]hydroxylamino)-5-acetyl-α-neuraminic acid-(2→8)-5-acetyl-α-neuraminic acid-(2→3)-β-D-galactopyranosyl-(1→4)-β-D-glucopyranoside (28)

To a solution of hemiacetal 27 (10 mg, 10.3 μmol) in NaOAc/AcOH buffer (0.1 M, pH 4.5, 103 μL) was added oxyamine 2 (9.3 mg, 103 μmol, 10 equiv). The reaction mixture was stirred for 24-48 h at 25-40° C. Purification by dialysis gave compound 28 (5.4 mg, 5.18 μmol, 50%) as a white fluffy solid.

$^1$H-NMR (500 MHz, D$_2$O): δ4.55 (d, 1H), 4.24-3.57 (m, 28 H), 4.23 (d, 1H), 3.27 (m, 2H), 2.84-2.77 (m, 1H), 2.81 (s, 3H), 2.70 (dd, 1H), 2.09, 2.05 (2s, 6H), 1.76 (t, 2H).

MS (ESI$^-$): m/z 497.36 (calc for C$_{37}$H$_{62}$N$_4$O$_{27}$$^{2-}$[M−2Na]$^{2-}$: m/z 497.18).

N-(N-Methyl-O-[2-(2-mercaptobutanamido)ethyl]hydroxylamino)-5-acetyl-α-neuraminic acid-(2→8)-5-acetyl-α-neuraminic acid-(2→3)-β-D-galactopyranosyl-(1→4)-β-D-glucopyranoside (29)

To a suspension of amine 28 (3.2 mg, 3.07 μmol) in anhyd DMF (61 μL) were successively added DL-dithiothreitol (tip of spatula), γ-thiobutyrolactone (2.7 μL, 30.7 μmol, 10 equiv) and Et$_3$N (4.3 μL, 30.7 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 29 (2.3 mg, 2.01 μmol, 66%) as a white fluffy solid.

$^1$H-NMR (500 MHz, D$_2$O): δ4.55 (d, 1H), 4.21-3.55 (m, 28 H), 4.20 (d, 1H), 3.43 (m, 2H), 2.80-2.75 (m, 1H), 2.77 (s, 3H), 2.71-2.68 (m, 1H), 2.57 (t, 2H), 2.40 (t, 2H), 2.09, 2.05 (2s, 6H), 1.92-1.89 (m, 2H), 1.76 (t, 2H).

MS (ESI$^-$): m/z 548.26 (calc for C$_{41}$H$_{68}$N$_4$O$_{28}$S$^{2-}$[M−2Na]$^{2-}$: m/z 548.19).

GD3 Polymer (30)

To a solution of 5 (0.75 mg, 3.67 μmol) in DMF (37 μL) were subsequently added compound 29 (2.1 mg, 1.83 μmol, 0.5 equiv), water (10 μL) and a solution of DBU (0.8 μL, 5.5 μmol, 1.5 equiv) in DMF (7 μL). After stirring for 1-24 h at rt, thioglycerol (1.0 μL, 11.0 μmol, 3.0 equiv) and Et$_3$N (1.5 μL, 11.0 μmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GD3 polymer 30 (0.3 mg, 18%) as a white solid. According to $^1$H NMR, the product contained approximately 17% of the lysine side-chains substituted by the carbohydrate epitope 29.

Scheme 8: Synthesis of the GT1a polymer 34

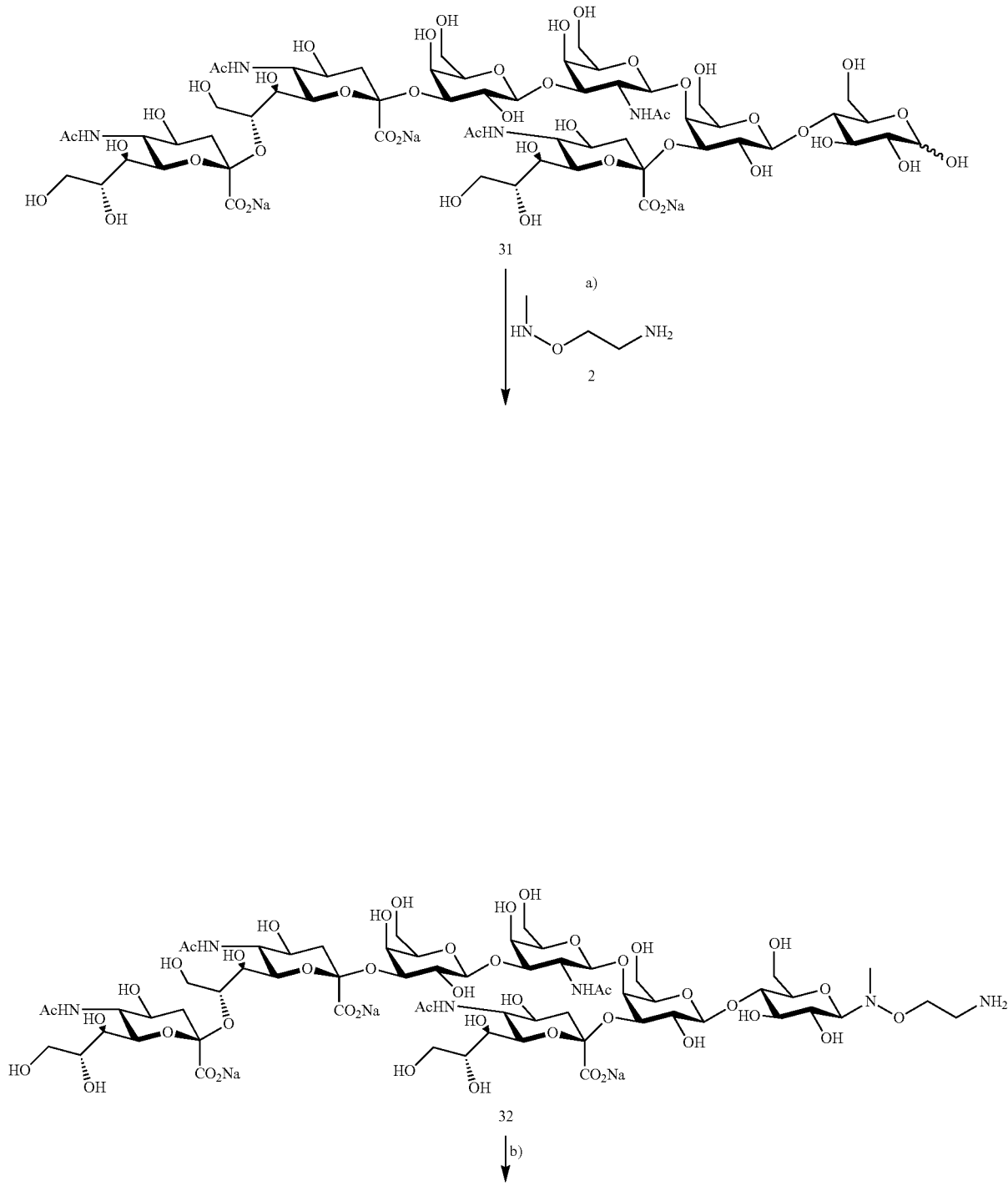

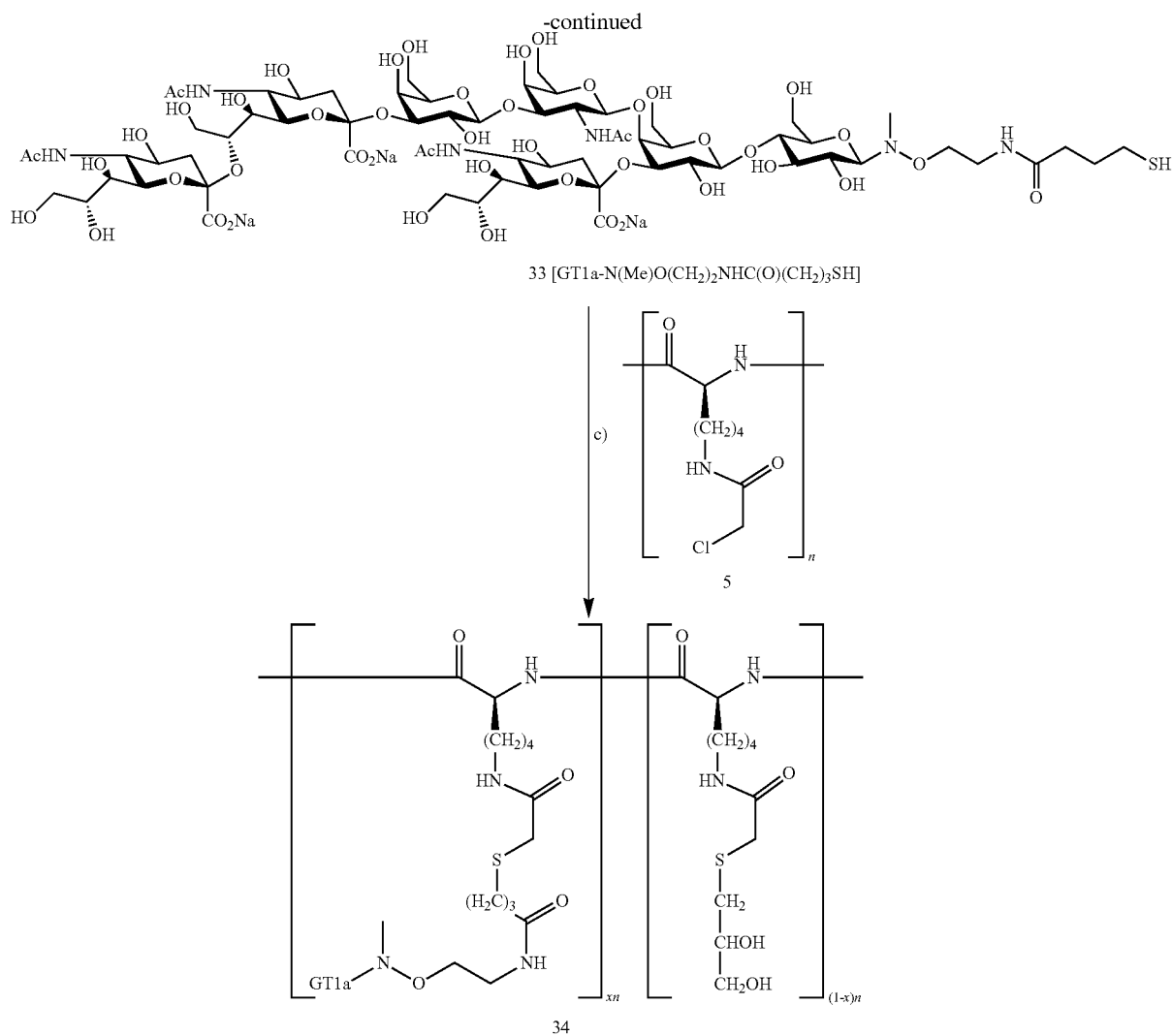

Reagents and conditions: a) 2, sodium acetate buffer, 84%; b) DL-dithiothreitol, γ-thiobutyrolactone, Et₃N, DMF, 24%; c) i. 5, DBU, DMF/H₂O; ii. thioglycerol, Et₃N, 25%

N-(N-Methyl-O-[2-aminoethyl]hydroxylamino)-5-acetyl-α-neuraminic acid-(2→8)-5-acetyl-α-neuraminic acid-(2→3)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (32)

To a solution of hemiacetal 31 (5.0 mg, 3.04 μmol) in NaOAc/AcOH buffer (0.1 M, pH 4.5, 30 μL) was added oxyamine 2 (2.7 mg, 30 μmol, 10 equiv). The reaction mixture was stirred for 24-48 h at 25-40° C. Purification by dialysis gave compound 32 (4.38 mg, 2.55 μmol, 84%) as a white fluffy solid.

$^1$H-NMR (500 MHz, D$_2$O): δ4.80 (d, 1H), 4.64, 4.55 (2d, 2H), 4.24 (d, 1H), 4.20-3.40 (m, 45H), 3.29-3.27 (m, 2H), 2.81 (s, 3H), 2.78-2.69 (m, 3H), 2.08, 2.05 (2s, 12H), 1.85-1.65 (m, 3H).

MS (ESI$^-$): m/z 836.33 (calc for C$_{62}$H$_{101}$N$_6$O$_{45}$Na$^{2-}$[M−2Na]$^{2-}$: m/z 836.29).

N-(N-Methyl-O-[2-(2-mercaptobutanamido)ethyl]hydroxylamino)-5-acetyl-α-neuraminic acid-(2→8)-5-acetyl-α-neuraminic acid-(2→3)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (33)

To a suspension of amine 32 (3.2 mg, 1.86 μmol) in anhyd DMF (37 μL) were successively added DL-dithiothreitol (0.5 mg, 3.35 μmol, 1.8 equiv), γ-thiobutyrolactone (1.6 μL, 18.6 μmol, 10 equiv) and Et$_3$N (2.6 μL, 18.6 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 33 (0.82 mg, 0.45 μmol, 24%) as a white fluffy solid.

$^1$H-NMR (500 MHz, D$_2$O): δ4.79 (d, 1H), 4.64, 4.55 (2d, 2H), 4.20-3.40 (m, 39H), 2.77 (s, 3H), 2.79-2.66 (m, 3H), 2.57 (t, 2H), 2.40 (t, 2H), 2.08, 2.05 (2s, 14H), 1.94-1.74 (m, 2H).

MS (ESI$^-$): m/z 583.80 (calc for C$_{66}$H$_{107}$N$_6$O$_{46}$SNa$_3^{3-}$[M−3Na]$^{3-}$: m/z 583.87).

GT1a Polymer (34)

To a solution of 5 (0.19 mg, 0.90 μmol) in DMF (9 μL) were subsequently added compound 33 (0.82 mg, 0.45 μmol, 0.5 equiv), water (1 μL) and a solution of DBU (0.2 μL, 1.36 μmol, 1.5 equiv) in DMF (2 μL). After stirring for 1-3 h at rt, thioglycerol (0.2 μL, 2.7 μmol, 3.0 equiv) and Et$_3$N (0.4 μL, 2.7 μmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GT1a polymer 34 (0.28 mg, 25%) as a white solid. According to $^1$H NMR, the product contained approximately 57% of the lysine side-chains substituted by the carbohydrate epitope 33.

Scheme 9: Synthesis of the GM1a-linker2 polymer 38

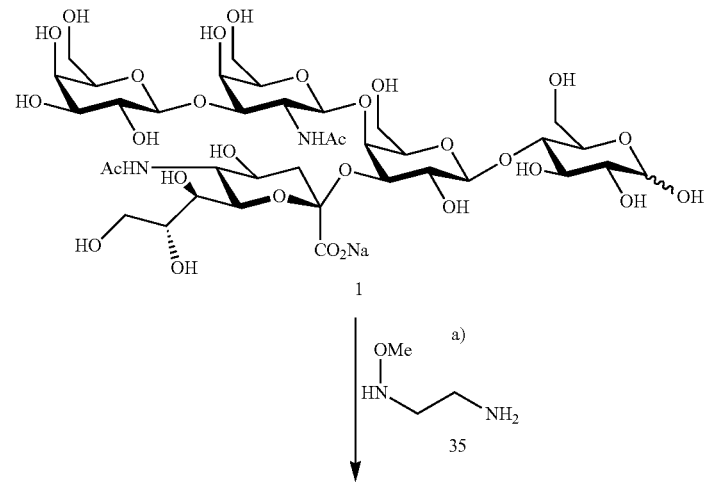

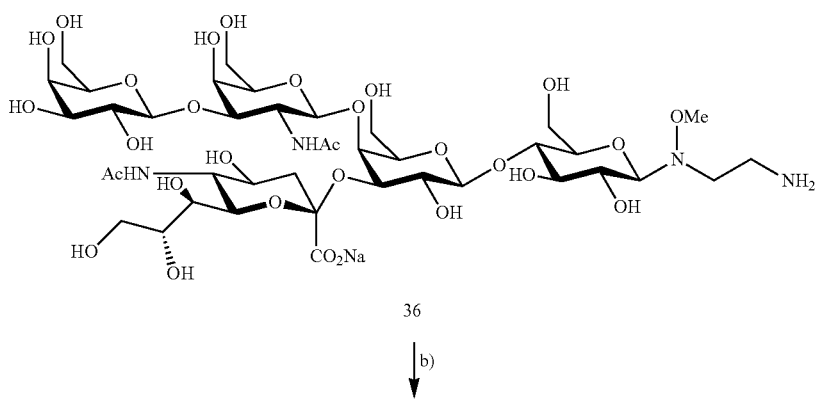

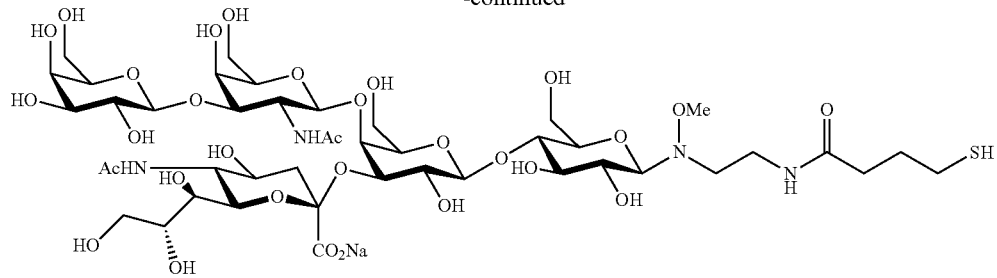

37 [GM1a-N(OMe)(CH₂)₂NHC(O)(CH₂)₃SH]

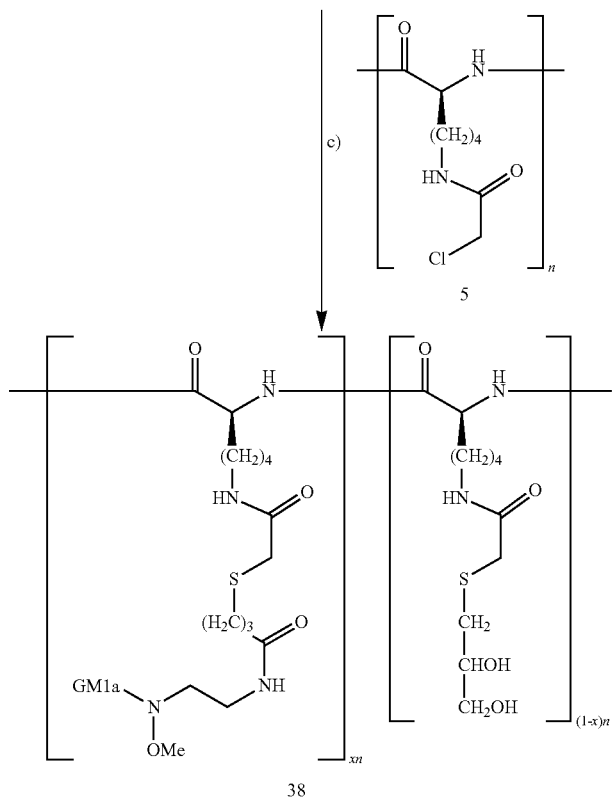

38

Reagents and conditions: a) 35, sodium acetate buffer, 58%; b) DL-dithiothreitol, γ-thiobutyrolactone, Et₃N, DMF, 74%; c) i. 5, DBU, DMF/H₂O; ii. thioglycerol, Et₃N, 41%

N-[O-Methyl-N-(2-aminoethyl)hydroxylamino]-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (36)

To a solution of hemiacetal 1 (10.0 mg, 9.80 μmol) in NaOAc/AcOH buffer (0.1 M, pH 4.5, 98 μL) was added oxyamine 35 (8.8 mg, 98 μmol, 10 equiv). The reaction mixture was stirred for 24-48 h at 25-40° C. Purification by dialysis gave compound 36 (6.2 mg, 5.63 μmol, 58%) as a white fluffy solid.

$^1$H-NMR (500 MHz, D₂O): δ4.78 (d, 1H), 4.57-4.54 (m, 2H), 4.31 (d, 1H), 4.18-3.51 (m, 33H), 3.38 (t, 1H), 3.32 (m, 2H), 3.27 (m, 2H), 2.68 (dd, 1H), 2.05, 2.03 (2s, 6H), 1.95 (t, 1H).

HRMS (ESI⁺): m/z 1071.4177 (calc. for $C_{40}H_{71}N_4O_{29}^+$ [M+H]⁺: 1071.4198).

N-(N-[2-(2-Mercaptobutanamido)ethyl]-O-methyl)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (37)

To a suspension of amine 36 (6.1 mg, 5.6 μmol) in anhyd DMF (112 μL) were successively added DL-dithiothreitol (tip of spatula), γ-thiobutyrolactone (4.9 μL, 56 μmol, 10 equiv) and Et₃N (7.8 μL, 56 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 37 (5.0 mg, 4.2 μmol, 74%) as a white fluffy solid.

$^1$H-NMR (500 MHz, D₂O): δ4.78 (d, 1H), 4.56 (m, 2H), 4.25 (d, 1H), 4.18-3.37 (m, 34H), 3.46 (m, 2H, Hb), 3.23 (m, 1H), 3.07 (m, 1H), 2.77 (m, 1H), 2.68 (dd, 1H), 2.41 (t, 2H), 2.05, 2.03 (2s, 6H), 1.97-1.93 (m, 3H).

MS (ESI⁻): m/z 1171.65 (calc. for $C_{44}H_{75}N_4O_{30}S^-$ [M−Na]⁻: 1171.42).

GM1a-Linker2-Polymer (38)

To a solution of 5 (1.7 mg, 8.4 μmol) in DMF (84 μL) were subsequently added compound 37 (5.0 mg, 4.2 μmol, 0.5 equiv), water (8.4 μL) and a solution of DBU (1.9 μL, 12.5 μmol, 1.5 equiv) in DMF (17 μL). After stirring for 1-24 h at rt, thioglycerol (2.2 μL, 25 μmol, 3.0 equiv) and Et₃N (3.5 μL, 25 μmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM1a-linker2 polymer 38 (2.5 mg, 41%) as a white solid. According to ¹H NMR, the product contained approximately 41% of the lysine side-chains substituted by the carbohydrate epitope 37.

Scheme 10: Synthesis of the GM1a-linker3 polymer 42

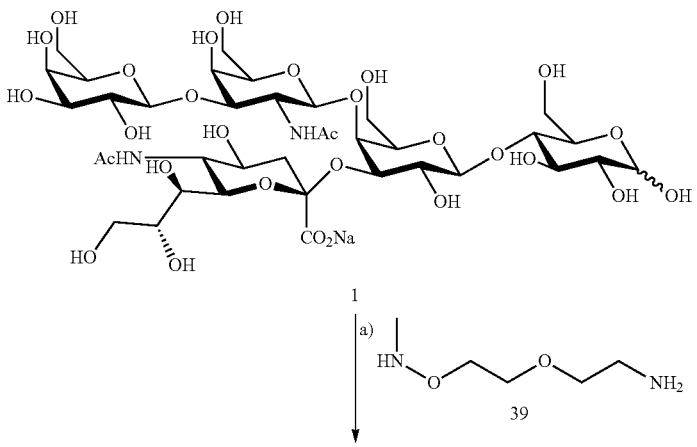

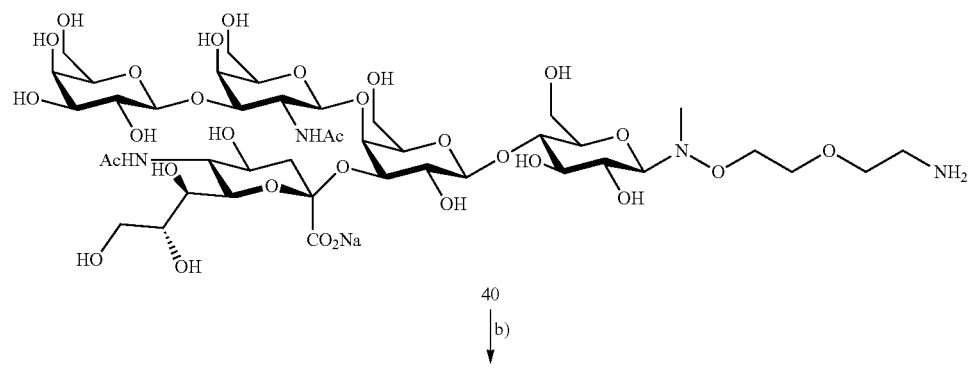

-continued

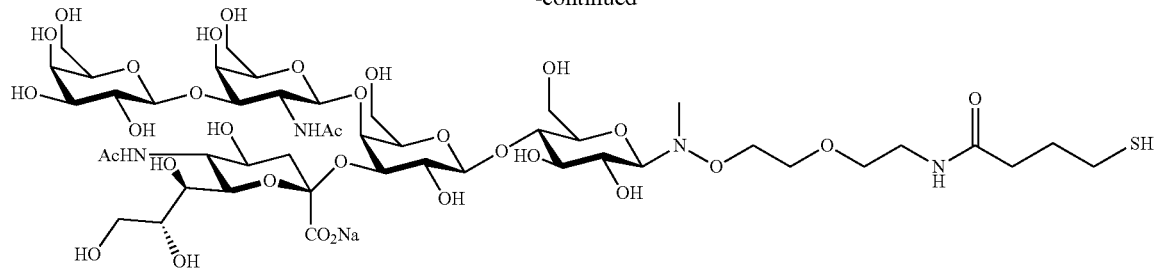

41 [GM1a-N(Me)(O(CH₂)₂)₂NHC(O)(CH₂)₃SH]

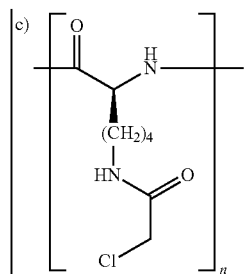

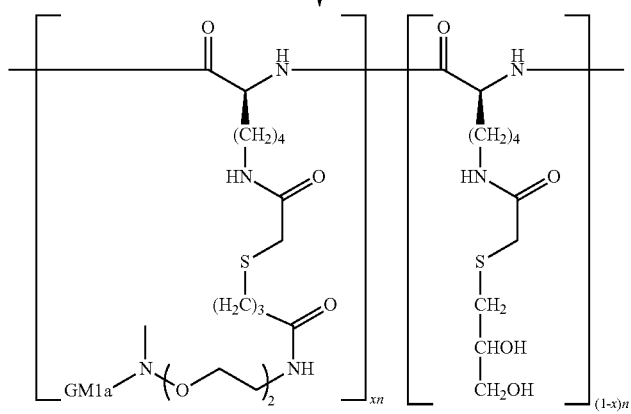

42

Reagents and conditions: a) 39, sodium acetate buffer, 51%; b) DL-dithiothreitol, γ-thiobutyrolactone, Et₃N, DMF, 64%; c) i. 5, DBU, DMF/H₂O; ii. tihoglycerol, Et₃N, 32%

N-(N-Methyl-O-[2-O-(2-aminoethyl)hydroxylethyl)]hydroxylamino)-β-D-galactopyranosyl-(1→3)-2-acetamido-β-D-galactopyranosyl-(1→4)-[5-acetyl-α-neuraminic acid-(2→3)]-β-D-galactopyranosyl-(1→4)-β-D-glucopyranoside (40)

To a solution of hemiacetal 1 (10.0 mg, 9.80 μmol) in NaOAc/AcOH buffer (0.1 M, pH 4.5, 98 μL) was added oxyamine 39 (13.1 mg, 98 μmol, 10 equiv). The reaction mixture was stirred for 24-48 h at 25-40° C. Purification by dialysis gave compound 40 (7.48 mg, 6.50 μmol, 51%) as a white fluffy solid.

¹H-NMR (500 MHz, D₂O): δ4.78 (d, 1H), 4.56 (d, 2H), 4.19 (d, 1H), 4.18-4.14 (m, 3H), 4.13-3.48 (m, 32H), 3.38 (dd, 1H), 3.23 (m, 2H), 2.79 (s, 3H), 2.67 (m, 1H), 2.05, 2.02 (2s, 6H), 1.94 (m, 1H).

HRMS (ESI⁺: m/z 1115.4447 (calc. for $C_{42}H_{75}N_4O_{30}^+$ [M+H]⁺: 1115.4461).

N-(N-Methyl-O-[2-O-[2-(2-mercaptobutanamido)ethyl]hydroxylethyl]hydroxylamino)-β-D-galactopyranosyl-(1→3)-2-acetamido-β-D-galactopyranosyl-(1→4)-[5-acetyl-α-neuraminic acid-(2→3)-β-D-galactopyranosyl-(1→4)]-β-D-glucopyranoside (41)

To a suspension of amine 40 (7.48 mg, 6.50 μmol) in anhyd DMF (130 μL) were successively added DL-dithiothreitol (tip of spatula), γ-thiobutyrolactone (5.6 μL, 65 μmol, 10 equiv) and Et₃N (9.1 μL, 65 μmol, 10 equiv). The reaction mixture was stirred for 12-24 h at 25-40° C. After that time, the reaction mixture was concentrated and the solvents co-evaporated with xylene. Purification by P2 size-exclusion chromatography gave compound 41 (5.21 mg, 4.16 μmol, 64%) as a white fluffy solid.

¹H-NMR (500 MHz, D₂O): δ4.78 (d, 1H), 4.56 (d, 2H), 4.19 (d, 1H), 4.18-3.52 (m, 36H), 3.41 (t, 2H), 3.37 (dd, 1H), 2.79 (s, 3H), 2.67 (m, 1H), 2.57 (t, 2H), 2.39 (t, 2H), 2.05, 2.02 (2s, 6H), 1.98-1.88 (m, 3H).

HRMS (ESI⁺): m/z 1239.4412 (calc. for $C_{46}H_{80}N_4O_{31}NaS^+$ [M+H]⁺ 1239.4419).

GM1a-Linker3-Polymer (42)

To a solution of 5 (1.72 mg, 8.41 µmol) in DMF (84 µL) were subsequently added compound 41 (5.21 mg, 4.21 µmol, 0.5 equiv), water (8.4 µL) and a solution of DBU (1.9 µL, 13 µmol, 1.5 equiv) in DMF (17 µL). After stirring for 1-24 h at rt, thioglycerol (2.2 µL, 25 µmol, 3.0 equiv) and Et$_3$N (3.5 µL, 25 µmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM1a-linker3-polymer 42 (2.64 mg, 32%) as a white solid. According to $^1$H NMR, the product contained approximately 61% of the lysine side-chains substituted by the carbohydrate epitope 41.

Scheme 11: Synthesis of the GM1a-linker4-polymer 45

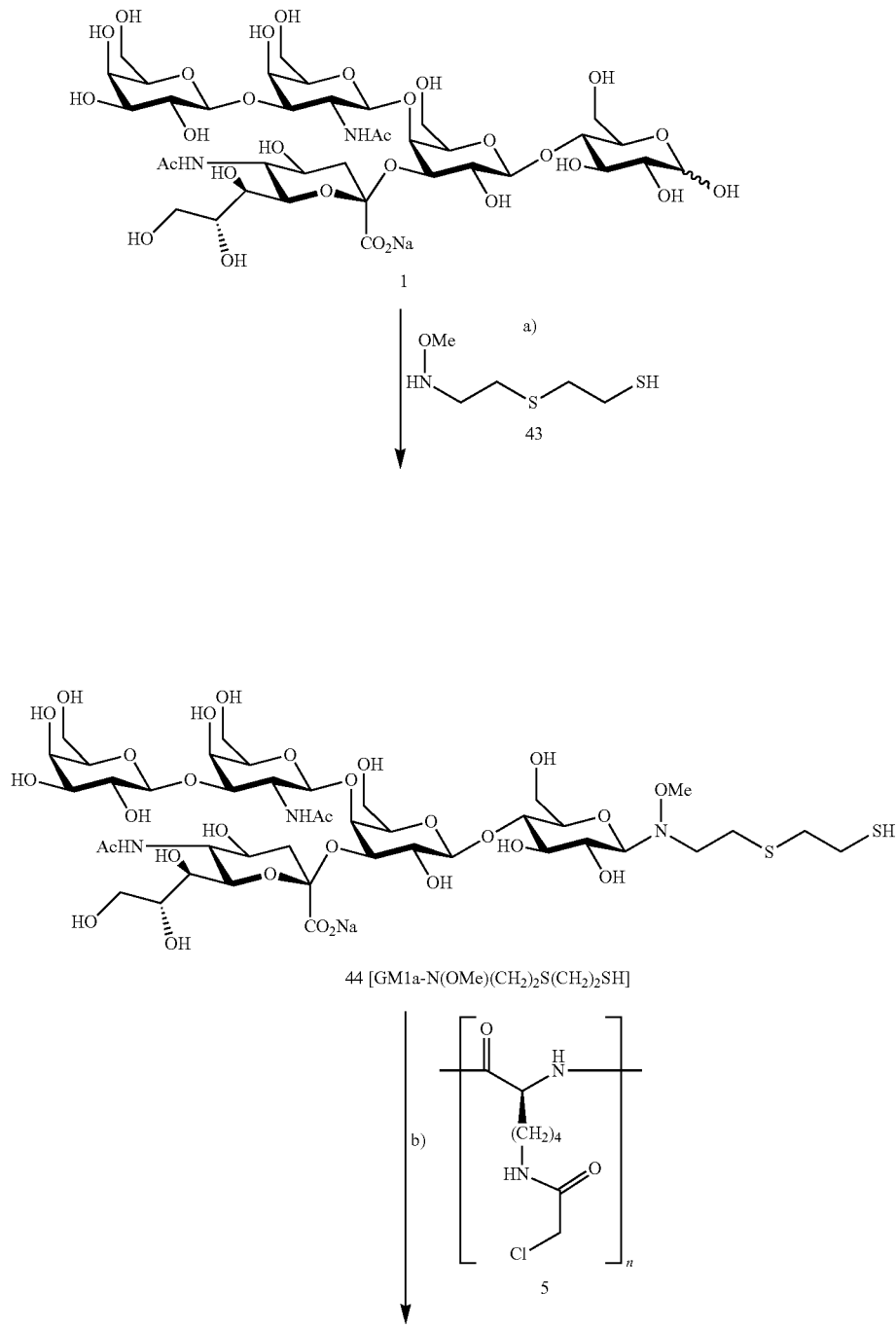

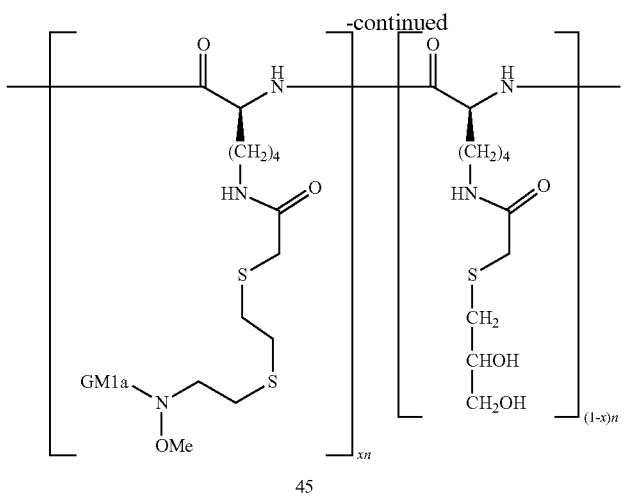

45

Reagents and conditions: a) 43, sodium acetate buffer, 48%; b) i. 5, DBU, DMF/H₂O; ii. thioglycerol, Et₃N, 90%

N-(O-Methyl-N-[2-(2-ethylthio)ethylthio]hydroxy-lamino)-β-D-galactopyranosyl-(1→3)-2-acetamido-β-D-galactopyranosyl-(1→4)-[5-acetyl-α-neuraminic acid-(2→3)-β-D-galactopyranosyl-(1→4)]-β-D-glucopyranoside (44)

To a solution of hemiacetal 1 (10.0 mg, 9.80 µmol) in NaOAc/AcOH buffer (0.1 M, pH 4.5, 98 µL) was added oxyamine 43 (16 mg, 98 µmol, 10 equiv). The reaction mixture was stirred for 24-48 h at 25-40° C. Purification by reverse phase chromatography (0→100% MeOH in H₂O) gave compound 44 (5.5 mg, 4.7 µmol, 48%) as a white fluffy solid.

¹H-NMR (500 MHz, D₂O): δ4.78 (d, 1H), 4.56, 4.55 (2d, 2H), 4.26 (d, 1H), 4.21-3.48 (m, 36H), 3.38 (t, 1H), 3.35-3.30 (m, 1H), 3.16 (m, 1H), 3.04-3.01 (m, 2H), 3.01-2.99 (m, 2H), 2.89 (t, 2H), 2.68 (dd, 1H), 2.05 2.02 (2s, 6H), 1.95 (t, 1H).

MS (ESI⁻): m/z 1146.59 (calc. for C₄₂H₇₂N₃O₂₉S₂⁻[M−Na]⁻ 1146.37).

GM1a-Linker4-Polymer (45)

To a solution of 5 (1.17 mg, 5.13 µmol) in DMF (57 µL) were subsequently added compound 44 (3.35 mg, 2.86 µmol, 0.5 equiv), water (5.8 µL) and a solution of DBU (1.3 µL, 8.6 µmol, 1.5 equiv) in DMF (12 4). After stirring for 1-3 h at rt, thioglycerol (1.5 µL, 17 µmol, 3.0 equiv) and Et₃N (2.4 µL, 17 µmol, 3.0 equiv) were added. The reaction mixture was stirred at rt for another 12-24 h. The product was precipitated by slow addition to a stirring solution of EtOH/Et₂O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave GM1a-linker4-polymer 45 (3.08 mg, 90%) as a white solid. According to ¹H NMR, the product contained approximately 30% of the lysine side-chains substituted by the carbohydrate epitope 44.

Scheme 12: Synthesis of linker2 35

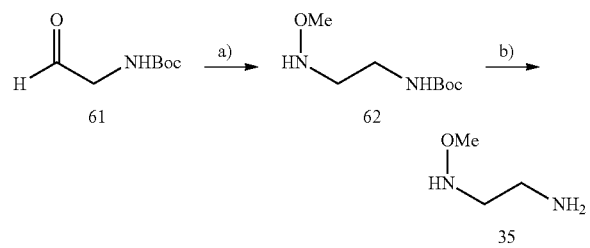

Reagents and conditions: a) i. MeONH₂•HCl, AcONa, EtOH; ii. NaBH₃CN, AcCl, 39%; b) TFA, DCM, quant tert-Butyl (2-(methoxyamino)ethyl)carbamate (62)

To a solution of aldehyde 61 (340 mg, 2.14 mmol) in EtOH (3.5 mL) was added methoxyamine hydrochloride (214 mg, 3.77 mmol, 1.2 equiv) and AcONa (350 mg, 4.27 mmol, 2.0 equiv). The reaction mixture was stirred overnight at rt. After that time, NaBH₃CN (201 mg, 3.20 mmol, 1.5 equiv) was added followed by dropwise addition of a freshly prepared solution of 1 M ethanolic HCl (7.0 mL, freshly prepared from AcCl and EtOH). After stirring for 1 h at rt, the reaction was neutralized by addition of satd aq NaHCO₃. The reaction mixture was diluted with H₂O and extracted with DCM (3×). The organic phases were pooled, washed with brine and dried over anhyd Na₂SO₄. The suspension was filtrated and concentrated under reduced pressure. Purification by flash chromatography eluting with PE/Acetone (85:15) yielded the aminoalcohol 62 (158 mg, 0.832 mmol, 39%) as a colourless oil.

¹H-NMR (500 MHz, CDCl₃) δ5.69 (s, 1H), 4.91 (s, 1H), 3.54 (s, 3H), 3.30 (m, 2H), 3.00 (t, 2H), 1.46 (s, 9H).

2-(Methoxyamino)ethan-1-amine (35)

Aminoalcohol 62 (160 mg, 0.84 mmol) was dissolved in DCM (1.1 mL). The solution was cooled to 0° C. and trifluoroacetic acid (TFA, 320 µL, 4.2 mmol, 5.0 equiv) was added dropwise to the reaction mixture. After stirring for 1 h at 0° C. followed by 3 h at rt, the reaction mixture was diluted with MeOH and neutralized with free base Amberlite resin. The suspension was filtered over cotton and the filtrate was concentrated in vacuo. Purification by flash chromatography eluting with DCM/MeOH (9:1→7:3) gave amine 62 (100 mg) as a TFA salt partially.

$^1$H-NMR (500 MHz, D$_2$O) δ3.47 (s, 3H), 3.13 (m, 2H), 3.10 (m, 2H).

Scheme 13: Synthesis of linker3 39

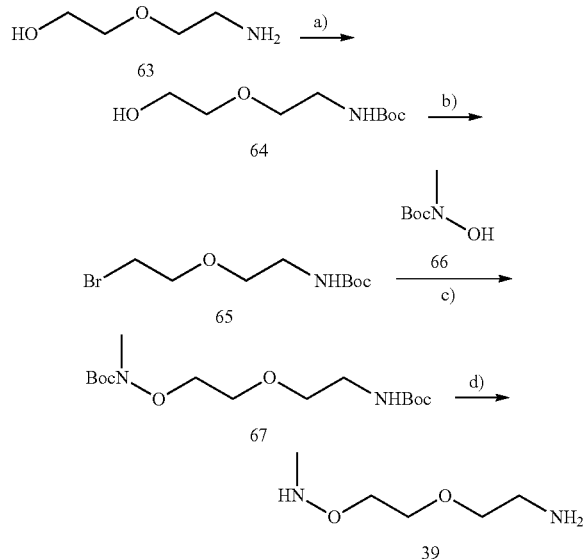

Reagents and conditions: a) Boc$_2$O, Et$_3$N, DCM, 84%; b) i. MsCl, Et$_3$N, DCM; ii. LiBr, Acetone, 98%; c) 66, NaH, DMF, 90%; d) TFA, DCM, 96% tert-Butyl (2-(2-hydroxyethoxy)ethyl)carbamate (64)

Amine 63 (1.0 mL, 10 mmol) was dissolved in DCM (50 mL). The solution was cooled to 0° C. and di-tert-butyl dicarbonate (Boc$_2$O, 1.74 g, 8.9 mmol, 0.8 equiv) was added to the solution followed by Et$_3$N (1.4 mL, 10 mmol, 1.0 equiv). After stirring for 1 h at 0° C. followed by 2 h at rt, the reaction mixture was diluted with DCM and washed with H$_2$O and brine. The organic phase was dried over anhyd Na$_2$SO$_4$. The suspension was filtered over cotton and the filtrate concentrated in vacuo. Purification by flash chromatography eluting with DCM/MeOH (1:0→9:1) gave alcohol 64 (1.37 g, 6.67 mmol, 84%) as a colourless oil.

$^1$H-NMR (500 MHz, CDCl$_3$) δ4.88 (s, 1H), 3.74 (m, 2H), 3.58 (t, 2H), 3.56 (m, 2H), 3.34 (m, 2H), 2.05 (s, 1H), 1.45 (s, 9H).

tert-Butyl (2-(2-bromoethoxy)ethyl)carbamate (65)

Alcohol 64 (1.25 g, 6.09 mmol) was dissolved in DCM (34 mL). The solution was cooled to 0° C. and methanesulfonyl chloride (MsCl, 0.80 mL, 10.3 mmol, 1.7 equiv) was added to the solution followed by Et$_3$N (1.9 mL, 13.4 mmol, 2.2 equiv). After stirring for 3 h at rt, the reaction mixture was diluted with acetone (33 mL) and LiBr (8.9 g, 103 mmol, 17 equiv) was added. The reaction mixture was stirred overnight at rt. After that time, the solvents were evaporated under reduced pressure. The crude residue was diluted with EtOAc and washed with H$_2$O and brine. The organic phase was dried over anhyd Na$_2$SO$_4$. The suspension was filtered over cotton and the filtrate concentrated in vacuo. Purification by flash chromatography eluting with PE/Acetone (85:15→8:2) gave bromide 65 (1.60 g, 5.95 mmol, 98%) as a colourless oil.

$^1$H-NMR (500 MHz, CDCl$_3$): δ4.91 (s, 1H), 3.78 (t, 2H), 3.56 (t, 2H), 3.47 (t, 2H), 3.33 (d, 2H), 1.45 (s, 9H).

tert-Butyl (2-(2-((tert-butoxycarbonyl)amino)ethoxy)ethoxy)(methyl)carbamate (67)

NaH (60% in mineral oil, 82 mg, 2.04 mmol, 0.96 equiv) was added at 0° C. to a solution of aminoalcohol 66 (313 mg, 2.12 mmol, 1.0 equiv) in anhyd DMF (1.4 mL). After stirring for 30 min at that temperature, a solution of bromide 65 (456 mg, 1.70 mmol, 0.8 equiv) was added to the reaction mixture. The reaction mixture was stirred 1 h at 0° C. followed by 2 h at rt. After that time, the reaction was quenched by addition of MeOH, concentrated in vacuo and the solvent coevaporated with xylene. Purification by flash chromatography eluting with PE/Acetone (8:2→75:25) gave aminoalcohol 67 (510 mg, 1.53 mmol, 90%) as a colourless oil.

$^1$H-NMR (500 MHz, CDCl$_3$): δ5.04 (s, 1H), 4.04-3.93 (m, 2H), 3.69-3.62 (m, 2H), 3.55 (t, 2H), 3.33 (m, 2H), 3.11 (s, 3H), 1.49 (s, 9H), 1.44 (s, 9H).

2-(2-((methylamino)oxy)ethoxy)ethan-1-amine (39)

Aminoalcohol 67 (421 mg, 1.26 mmol) was dissolved in DCM (1.6 mL). The solution was cooled to 0° C. and TFA (480 µL, 6.29 mmol, 5.0 equiv) was added dropwise to the reaction mixture. After stirring for 1 h at 0° C. followed by 5 h at rt, the reaction mixture was diluted with MeOH and neutralized with free base Amberlite resin. The suspension was filtered over cotton and the filtrate was concentrated in vacuo. Purification by flash chromatography eluting with DCM/MeOH (95:5→7:3) gave amine 39 (162 mg, 1.21 mmol, 96%) as a colourless oil.

$^1$H-NMR (500 MHz, D$_2$O): δ3.94 (m, 2H), 3.78 (t, 2H), 3.74 (m, 2H), 3.24 (t, 2H), 2.69 (s, 3H).

Scheme 14: Synthesis of linker4 43

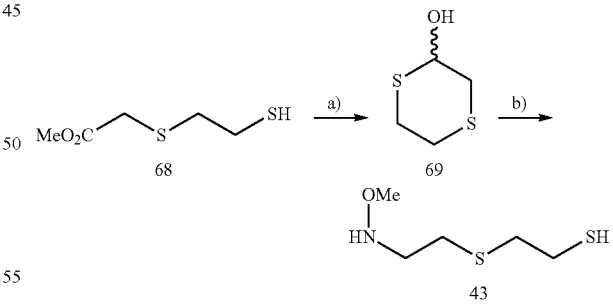

Reagents and conditions: a) DIBAL-H, DCM, 61%; b) i. MeONH$_2$•HCl, AcONa, EtOH; ii. NaBH$_3$CN, AcCl, EtOH, 17%

1,4-dithian-2-ol (69)

Ester 68 (100 mg, 0.60 mmol) was dissolved in anhyd DCM (1.2 mL). The solution was cooled to −78° C. and DIBAL-H (1 M in Toluene, 0.60 mL, 0.60 mmol, 1 equiv) was added dropwise to the reaction mixture. After stirring for 2 h at −78° C., DIBAL-H (0.3 mL, 0.3 mmol, 0.5 equiv)

was added dropwise to the reaction mixture. After stirring for another 30 min at −78° C., potassium sodium tartrate tetrahydrate (1.7 g) and H$_2$O (2.0 mL) were added to the reaction mixture. After stirring vigorously for 1 h at rt, the aqueous phase was extracted (3×) with DCM. The organic phases were pooled, washed with brine and dried over Na$_2$SO$_4$. The suspension was filtered over cotton and the filtrate concentrated in vacuo. Flash chromatography eluting with PE/Acetone (85:15→8:2) yielded derivative 69 (50 mg, 0.37 mmol, 61%) as a white solid.

$^1$H-NMR (500 MHz, CDCl$_3$): δ4.93 (dd, 1H), 3.65 (d, 1H), 3.46 (dd, 1H), 3.34 (m, 1H), 3.11-2.99 (m, 1H), 2.87 (dd 1H), 2.71 (m, 1H), 2.61 (m, 1H).

2-((2-(methoxyamino)ethyl)thio)ethane-1-thiol (43)

To a solution of compound 69 (232 mg, 1.7 mmol) in EtOH (2.8 mL) was added methoxyamine hydrochloride (171 mg, 2.0 mmol, 1.2 equiv) and AcONa (279 mg, 3.4 mmol, 2.0 equiv). The reaction mixture was stirred overnight at rt. After that time, NaBH$_3$CN (160 mg, 2.6 mmol, 1.5 equiv) was added followed by dropwise addition of a freshly prepared solution of 1 M ethanolic HCl (5.6 mL, freshly prepared from AcCl and EtOH). After stirring for 1 h at rt, the reaction was neutralized by addition of satd aq NaHCO$_3$. The reaction mixture was diluted with H$_2$O and extracted with DCM (3×). The organic phases were pooled, washed with brine and dried over anhyd Na$_2$SO$_4$. The suspension was filtrated and concentrated under reduced pressure. Purification by flash chromatography eluting with Tol/Acetone (85:15) yielded the aminoalcohol 43 (49 mg, 0.29 mmol, 17%) as a colourless oil.

$^1$H-NMR (500 MHz, CDCl$_3$): δ5.90 (s, 1H), 3.54 (s, 3H), 3.08 (t, 2H), 2.78-2.68 (m, 6H), 1.72 (t, 1H).

Scheme 15: Synthesis of linker5 72

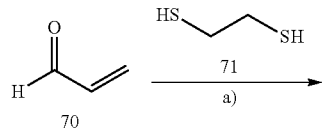

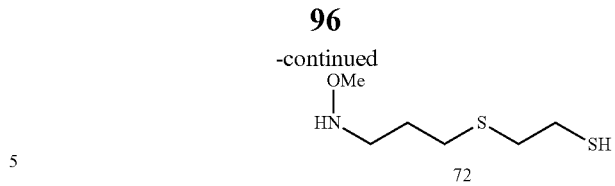

Reagents and conditions: a) i. 71; ii. MeONH$_2$·HCl, AcONa, EtOH; iii. NaBH$_3$CN, AcCl, EtOH, 29%

3-(3-(Methoxyamino)propylthio)propane-1-thiol (72)

Acrolein 70 (0.20 mL, 3.0 mmol) was added dropwise to 1,2-ethanedithiol 71 (1.3 mL, 15.0 mmol, 5.0 equiv) and the reaction mixture was stirred for 3 h at rt. After that time, the reaction mixture was diluted with EtOH (5.0 mL) and methoxyamine hydrochloride (300 mg, 3.6 mmol) and NaOAc (492 mg, 6.0 mmol) were added and the reaction mixture was stirred overnight at rt. After that time, NaBH$_3$CN (282 mg, 4.5 mmol, 1.5 equiv) was added to the reaction mixture, followed by dropwise addition of 1 M ethanolic HCl (10 mL, freshly prepared from AcCl and EtOH). After stirring for 1 h at rt, the reaction was neutralized by addition of satd aq NaHCO$_3$. The reaction mixture was diluted with H$_2$O and extracted with DCM (3×). The organic phases were pooled, washed with brine and dried over anhyd Na$_2$SO$_4$. The suspension was filtrated and concentrated under reduced pressure. Purification by flash chromatography eluting with Tol/Acetone (8:2) yielded the aminoalcohol 72 (159 mg, 0.88 mmol, 29%) as a colourless oil.

$^1$H-NMR (500 MHz, CDCl$_3$): δ5.60 (s, 1H), 3.53 (s, 3H), 3.01 (t, 2H), 2.76 (m, 2H), 2.73 (m, 2H), 2.62 (t, 2H), 1.82 (m, 2H), 1.72 (dd, 1H).

Scheme 16: Synthesis of the GM4 mimetic conjugate 78

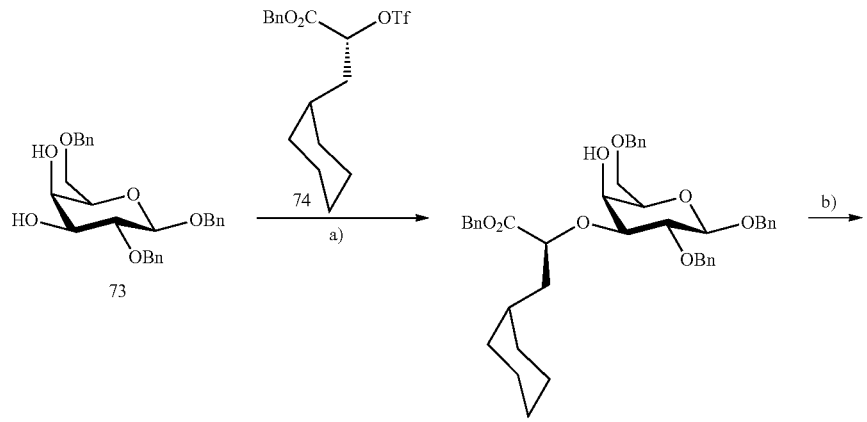

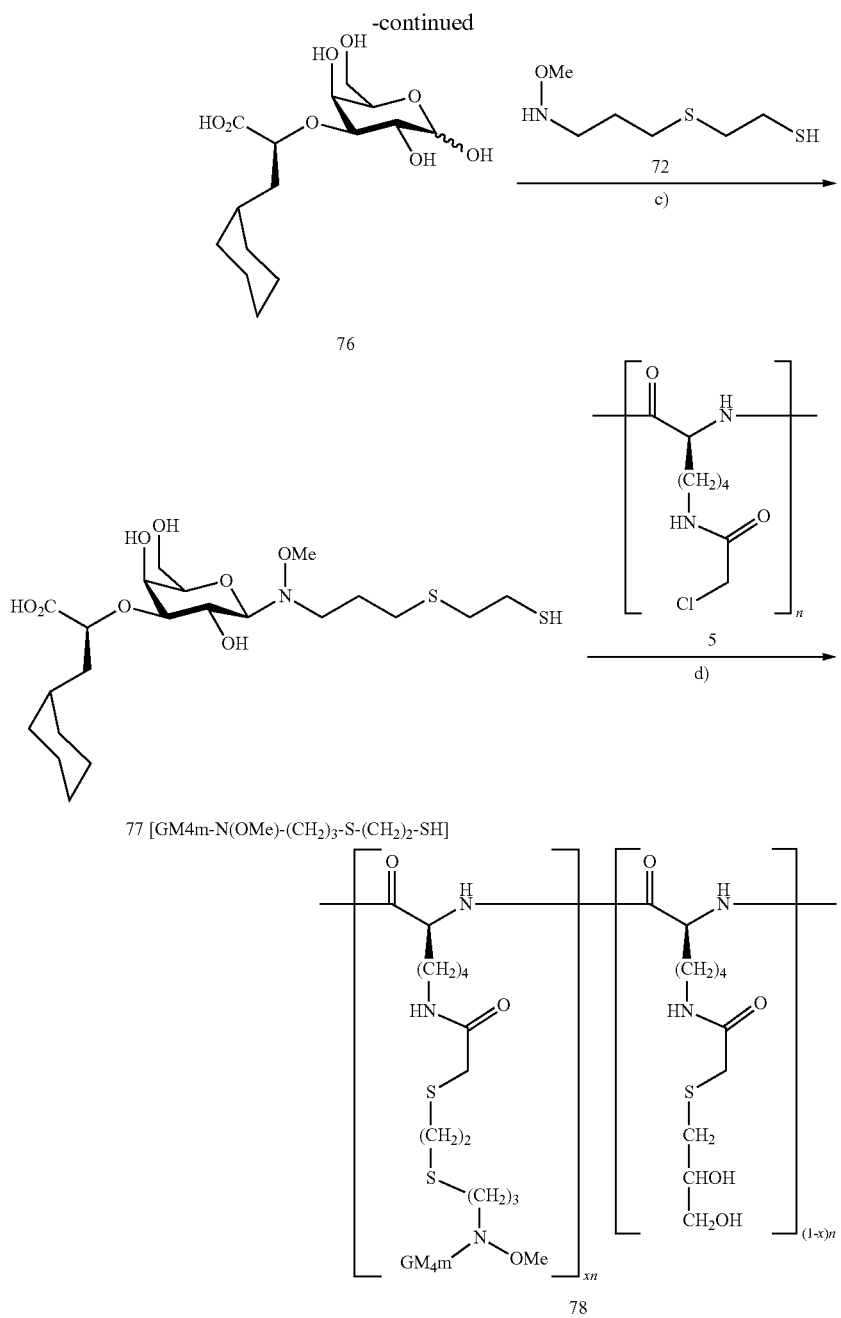

Reagents and conditions: a) i. Bu₂SnO, MeOH; ii. 74, CsF, DME, 23%; b) Pd(OH)₂, H₂, THF/H₂O, 40%; c) 72, AcOH/AcOH buffer, EtOH, 40° C., 64% ; d) i. 5, DBU, DMF/H₂O; ii. thioglycerol, Et₃N, 67%

Benzyl 2,6-di-O-benzyl-3-O-((1S)-1-benzyloxycarbonyl-2-cyclohexyl-ethyl)-β-D-galactopyranoside (75)

Diol 73 (100 mg, 0.22 mmol) was dissolved in anhyd MeOH (5 mL). Bu₂SnO (58 mg, 0.23 mmol, 1.05 equiv) was added and the reaction mixture was refluxed at 80° C. for 4 h. After that time, the solvent was evaporated under reduced pressure and the crude residue was dried under high vacuum for 5 h. The crude residue was dissolved under Ar in anhyd 1,2-dimethoxyethane (DME, 2.5 mL). Anhyd CsF (67 mg, 0.44 mmol, 2.0 equiv) and triflate 74 (175 mg, 0.44 mmol, 2.0 equiv) were added. After overnight stirring at rt under Ar, the solvent was evaporated under reduced pressure. Flash chromatography (Tol/EtOAc 8:2) yielded alcohol 75 (35 mg, 50 μmol, 23%).

$^1$H NMR (500 MHz, CDCl₃) δ7.36-7.23 (m, 20H), 5.19 (d, 1H), 5.10 (d, 1H), 4.95 (d, 1H), 4.94 (d, 1H), 4.67 (d, 1H), 4.64 (d, 1H), 4.63 (d, 1H), 4.58 (1d, 1H), 4.44 (d, 1H), 4.16 (dd, 1H), 3.79 (m, 1H), 3.77 (d, 2H), 3.73 (dd, 1H), 3.53 (m, 1H), 3.39 (t, 1H), 3.30 (dd, 1H), 1.70-1.45 (m, 8H), 1.06-0.97 (m, 3H), 0.86-0.76 (m, 2H).

MS (ESI⁺): m/z 717.60 (calc for $C_{43}H_{50}O_8Na^+$[M+Na]⁺: m/z 717.34).

3-O-((1S)-1-carboxy-2-cyclohexyl-ethyl)-α-β-D-galactopyranose (76)

To a deglazed solution of benzyl 75 (25 mg, 40 μmol) in THF/H$_2$O (4:1, 1.0 mL) was added under Ar Pd(OH)$_2$/C (10 mg). The reaction mixture was stirred overnight under an H$_2$ atmosphere. After that time, the reaction mixture was filtered over a PTFE Acrodisc 0.45 μm membrane and concentrated under reduced pressure. Reverse phase chromatography eluting with MeOH in H$_2$O (0→100%) gave the corresponding uronate 76 (8.5 mg, 25 μmol, 63%) as a white fluffy solid.

The α-anomer had: $^1$H-NMR (500 MHz, D$_2$O) δ5.17 (d, 1H), 4.20 (dd, 1H), 4.01-3.97 (m, 2H), 3.83 (dd, 1H), 3.69-3.62 (m, 2H), 3.61-3.58 (m, 1H), 1.74-1.51 (m, 8H), 1.19-1.07 (m, 3H), 0.93-0.81 (m, 2H).

The β-anomer had: $^1$H-NMR (500 MHz, D$_2$O) δ4.50 (d, 1H), 4.18 (dd, 1H), 3.94 (d, 1H), 3.69-3.62 (m, 2H), 3.61-3.58 (m, 1H), 3.51 (dd, 1H), 3.40 (dd, 1H), 1.74-1.51 (m, 8H), 1.19-1.07 (m, 3H), 0.93-0.81 (m, 2H).

MS (ESI$^+$): m/z 357.32 (calc for C$_{15}$H$_{26}$O$_8$Na$^+$[M+Na]$^+$: m/z 357.16).

N-(O-Methyl-N-[2-(2-ethylthio)propylthio]hydroxylamino)-3-O-((1S)-1-carboxy-2-cyclohexyl-ethyl)-β-D-galactopyranoside (77)

To a solution of hemiacetal 76 (8.8 mg, 26 μmol) in NaOAc/AcOH buffer (2 M, pH 4.5, 260 μL) was added oxyamine 72 (25 mg, 138 μmol, 5.2 equiv) and EtOH (520 μL). The reaction mixture was stirred for 48-72 h at 25-40° C. Purification by P2 size-exclusion chromatography followed by reverse phase chromatography (0%→100% MeOH in H$_2$O) gave compound 77 (8.3 mg, 16.7 μmol, 64%) as a white fluffy solid.

$^1$H-NMR (500 MHz, D$_2$O) δ4.17 (d, 1H), 4.00 (dd, 1H), 3.94 (dd, 1H), 3.88 (t, 1H), 3.80 (dd, 1H), 3.74 (dd, 1H), 3.66-3.63 (m, 4H), 3.46 (dd, 1H), 3.15 (m, 1H), 3.05-2.96 (m, 2H), 2.82-2.69 (m, 5H), 1.95-1.88 (m, 2H), 1.81 (m, 1H), 1.73-1.54 (m, 7H), 1.21 (m, 3H), 1.02-0.90 (m, 2H).

MS (ESI$^-$): m/z 496.37 (calc for C$_{21}$H$_{38}$O$_8$NS$_2^-$[M−H]$^-$: m/z 496.20).

GM4 Mimetic Polymer (78)

To a solution of 5 (2.38 mg, 11.6 μmol) in DMF (116 μL) were subsequently added compound 77 (1.60 mg, 3.22 μmol, 0.28 equiv), water (10 μL) and a solution of DBU (2.6 μL, 17.4 μmol, 1.5 equiv) in DMF (24 μL). After stirring for 1-3 h at rt, thioglycerol (3.0 μL, 34.8 μmol, 3.0 equiv) and Et$_3$N (4.9 μL, 34.8 μmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave the GM4 mimetic polymer 78 (3.84 mg, 67%) as a white solid. According to $^1$H NMR, the product contained approximately 56% of the lysine side-chains substituted by the carbohydrate epitope 77.

Scheme 17: Synthesis of linker-equipped HNK-1 disaccharide 58

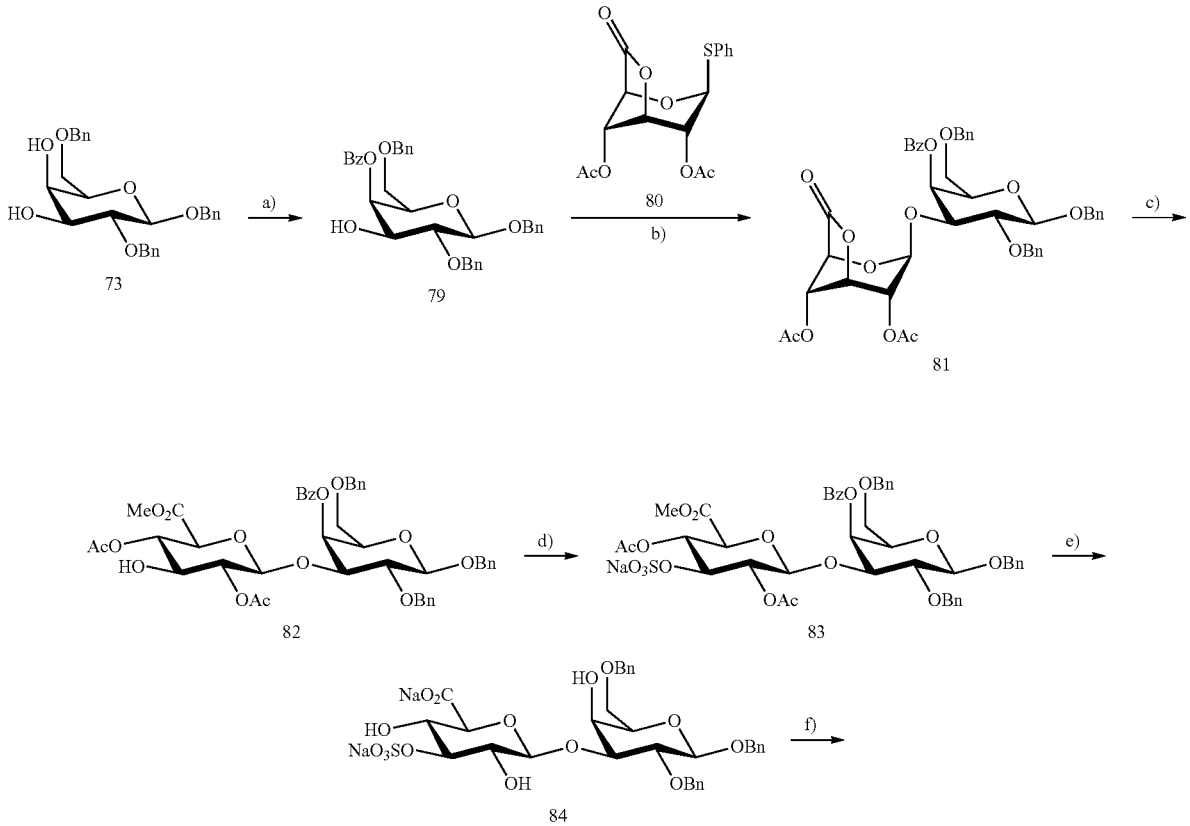

-continued

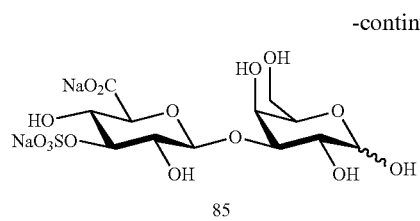
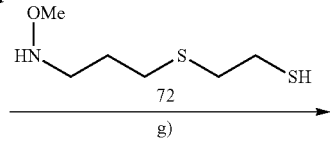

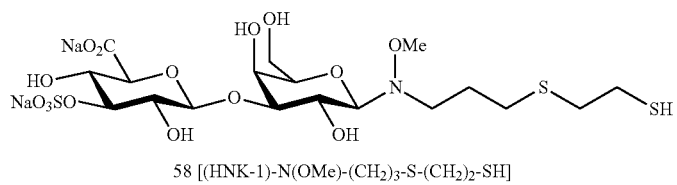

58 [(HNK-1)-N(OMe)-(CH₂)₃-S-(CH₂)₂-SH]

Reagents and conditions: a) BzCN, DMAP, 4 Å MS, DCM, -78° C., 74%; b) 80, NIS, TfOH, DCM, -20° C., 57%; c) NaOAc, MeOH, 64%;
d) SO₃•Pyr, DMF, 82%; e) LiOH, THF/H₂O, 83%; f) Pd(OH)₂/C, H₂, H₂O/MeOH, quant; g) 72, AcOH/AcOH buffer, EtOH, 40° C., 33%;

Benzyl 4-O-benzoyl-2,6-di-O-benzyl-β-D-galactopyranosyl (79)

A solution of diol 73 (285 mg, 0.634 mmol) in anhyd DCM (26 mL) was stirred over freshly activated 4 Å MS for 30 min at rt under an Ar atmosphere. The mixture was cooled to -78° C. and BzCN (87 mg, 0.665 mmol, 1.05 equiv) and DMAP (7.7 mg, 63 µmol, 0.1 equiv) were added. The reaction mixture was stirred for 4 h at -78° C. under an Ar atmosphere. The reaction was quenched with MeOH and the resulting suspension was filtered. The filtrate was washed with 10% aq NaHCO₃ and brine and dried over anhyd Na₂SO₄. The solution was filtered and concentrated under reduced pressure. Purification by flash chromatography eluting with toluene/EtOAc (95:5→9:1) yielded the alcohol 79 (260 mg, 0.469 mmol, 74%) as a white foam.

¹H-NMR (500 MHz, CDCl₃) δ8.12-7.10 (m, 20H), 5.65 (d, 1H), 5.02 (d, 1H), 5.00 (d, 1H), 4.71 (d, 1H), 4.69 (d, 1H), 4.57 (d, 1H), 4.53 (d, 1H), 4.46 (d, 1H), 3.90-3.86 (m, 1H), 3.87-3.84 (m, 1H), 3.69-3.65 (dd, 1H), 3.66-3.61 (m, 2H), 2.42 (d, 1H).

MS (ESI⁺): m/z 577.23 (calc for $C_{34}H_{34}O_7Na^+[M+Na]^+$: m/z 577.22).

Benzyl 2,4-di-O-acetyl-1-thio-β-D-glucopyranosidurono-3,6-lactone-(1→3)-4-O-benzoyl-2,6-di-O-benzyl-β-D-galactopyranoside (81)

To a solution of acceptor 79 (100 mg, 0.180 mmol) and donor 80 (127 mg, 0.360 mmol, 2.0 equiv) in anhyd DCM (1.0 mL) was added NIS (164 mg, 0.728 mmol, 2.4 equiv). The reaction mixture was cooled to -20° C. and TfOH (1.6 µL, 0.018 mmol, 0.1 equiv) was added. The reaction mixture was stirred for 1 h at -20° C. The reaction mixture was neutralized with Et₃N, diluted with DCM, washed with 10% aq Na₂S₂O₃ and brine and dried over anhyd Na₂SO₄. The suspension was filtered and concentrated under reduced pressure. Purification by flash chromatography eluting with toluene/EtOAc (85:15→8:2) yielded the disaccharide 81 (82 mg, 0.103 mmol, 57%) as a white foam.

¹H-NMR (500 MHz, CDCl₃) δ8.09-8.06, 7.56, 7.46, 7.37-7.22 (m, 20H), 5.54 (d, 1H), 5.37 (s, 1H), 5.07 (d, 1H), 5.03 (d, 1H), 4.99 (d, 1H), 4.92 (t, 1H), 4.77 (t, 1H), 4.70 (d, 1H), 4.68 (d, 1H), 4.51 (d, 1H), 4.54 (d, 1H), 4.56 (d, 1H), 4.19 (d, 1H), 4.03 (dd, 1H), 3.92 (dd, 1H), 3.84 (dd, 1H), 3.75 (dd, 1H), 3.58 (dd, 1H), 2.11, 1.82 (2s, 6H)

MS (ESI⁺): m/z 819.39 (calc for $C_{44}H_{44}O_{14}Na^+[M+Na]^+$: m/z 819.26).

Benzyl (methyl 2,4-di-O-acetyl-β-D-glucopyranuronate)-(1→3)-4-O-benzoyl-2,6-di-O-benzyl-β-D-galactopyranoside (82)

Lactone 81 (109 mg, 138 µmol) was dissolved at 0° C. in anhyd DCM/MeOH (1:4, 2.5 mL). Anhyd NaOAc (10 mg, 124 µmol, 0.9 equiv) was added and the reaction mixture was stirred overnight at 4° C. After that time, the mixture was neutralised by addition of Amberlyst H⁺ resin. The suspension was filtered and the filtrate concentrated under reduced pressure. Flash chromatography using PE/Acet (75:25→7:3) gave the desired alcohol 82 (73 g, 88.2 µmol, 64%) as a white foam.

¹H-NMR (500 MHz, CDCl₃) δ8.07-8.03, 7.60-7.55, 7.45, 7.40-7.22 (m, 20H), 5.67 (d, 1H), 5.13 (dd, 1H), 5.00 (d, 1H), 4.98 (d, 1H), 4.97 (d, 1H), 4.74 (dd, 1H), 4.71 (d, 1H), 4.64 (d, 1H), 4.56 (d, 1H), 4.52 (d, 1H), 4.48 (d, 1H), 4.05 (dd, 1H), 3.85 (m, 1H), 3.84 (d, 1H), 3.82 (dd, 1H), 3.69 (s, 3H), 3.65-3.62 (m, 2H), 3.59 (m, 1H), 2.70 (d, 1H), 2.06 (s, 3H), 1.79 (s, 3H).

MS (ESI⁺): m/z 851.47 (calc for $C_{45}H_{48}O_{15}Na^+[M+Na]^+$: m/z 851.29).

Benzyl (methyl 2,4-di-O-acetyl-3-O-sulfo-β-D-glucopyranuronate)-(1→3)-4-O-benzoyl-2,6-di-O-benzyl-β-D-galactopyranoside (83)

To a solution of alcohol 82 (72 mg, 87 µmol) in anhyd DMF (0.4 mL) was added SO₃.Py (41 mg, 26 mmol, 3.0 equiv) at 0° C. under Ar. After stirring for 2 h at rt, the reaction mixture was quenched by addition of NaHCO₃ (146 mg) and the reaction mixture was stirred for 30 min at rt. The suspension was filtered, the filtrate concentrated and the solvents were co-evaporated with xylene. Flash chromatography using DCM/MeOH (95:5→9:1) gave the sulfate 83 (67 mg, 72 µmol, 82%).

¹H-NMR (500 MHz, CDCl₃) δ7.98, 7.52-7.45, 7.40-7.20 (m, 20H), 5.61 (d, 1H), 5.19 (t, 1H), 4.99 (d, 1H), 4.98 (d, 1H), 4.92 (d, 1H), 4.83 (t, 1H), 4.69 (d, 1H), 4.63 (d, 1H), 4.55 (d, 1H), 4.50 (d, 1H), 4.46 (m, 1H), 4.45 (d, 1H), 3.98 (dd, 1H), 3.88 (d, 1H), 3.83 (t, 1H), 3.79 (dd, 1H), 3.65 (s, 3H), 3.63-3.52 (m, 2H), 1.95 (s, 3H), 1.75 (s, 3H).

MS (ESI⁻): m/z 907.45 (calc for $C_{45}H_{47}O_{18}S^-[M-Na]^-$: m/z 907.25).

Benzyl (sodium 3-O-sulfo-β-D-glucopyranuronate)-(1→3)-2,6-di-O-benzyl-β-D-galactopyranoside (84)

Acetate 83 (70 mg, 75 µmol) was dissolved in a solution of THF/H$_2$O (10:1, 1.8 mL). The reaction mixture was cooled to 0° C. and a 2.0 M aq LiOH solution (0.4 mL, 115 mmol, 9.5 equiv) was slowly added. The reaction mixture was stirred overnight and allowed to slowly reach rt. The next morning, the reaction was neutralised by addition of Amberlyst H$^+$ resin. The reaction mixture was filtered and concentrated under reduced pressure. Reverse phase chromatography eluting with MeOH in H$_2$O (0%→50%) gave the corresponding uronate 84 (47 mg, 62 µmol, 83%) as a white foam.

$^1$H-NMR (500 MHz, MeOD) δ7.43-7.20 (m, 15H), 4.92 (d, 1H), 4.78 (d, 1H), 4.77 (d, 1H), 4.67 (d, 1H), 4.62 (d, 1H), 4.51 (d, 1H), 4.59 (d, 1H), 4.32 (t, 1H), 4.12 (d, 1H), 3.83 (dd, 1H), 3.79-3.71 (m, 4H), 3.68-3.64 (m, 2H), 3.58 (dd, 1H).

MS (ESI$^-$): m/z 705.43 (calc for C$_{33}$H$_{37}$O$_{15}$S$^-$[M−2Na+H]$^-$: m/z 705.19).

Sodium 3-O-sulfo-β-D-glucopyranuronate-(1→3)-α,β-D-galactopyranose (85)

To a solution of benzyl 84 (46 mg, 61 µmol) in H$_2$O/MeOH (10:1, 5.2 mL) was added Pd(OH)$_2$/C (20 mg). The reaction mixture was stirred under an H$_2$ atmosphere for 6 h. After that time, the reaction mixture was filtered over a PTFE Acrodisc 0.45 µm membrane and concentrated under reduced pressure. Reverse phase chromatography eluting with H$_2$O gave the corresponding uronate 85 (29 mg, 60 µmol, quant) as a white fluffy solid.

The α-anomer had: $^1$H-NMR (500 MHz, D$_2$O) δ5.30 (d, 1H), 4.78 (d, 1H), 4.35 (t, 1H), 4.26 (dd, 1H), 4.12 (ddd, 1H), 4.00 (m, 2H), 3.82 (m, 1H), 3.77–3.70 (m, 3H), 3.62 (dd, 1H).

The β-anomer had: $^1$H NMR (500 MHz, D$_2$O) δ4.78 (d, 1H), 4.65 (d, 1H), 4.35 (t, 1H), 4.20 (d, 1H), 3.82 (dd, 1H), 3.77-3.70 (m, 5H), 3.66 (dd, 1H), 3.62 (dd, 1H).

MS (ESI$^-$): m/z 434.96 (calc for C$_{12}$H$_{19}$O$_{15}$S$^-$[M−2Na+H]$^-$: m/z 435.05).

N-(O-Methyl-N-[2-[(2-ethylthio)propylthio]hydroxylamine)-(sodium 3-O-sulfo-β-D-glucopyranuronate)-(1→3)-β-D-galactopyranoside (58)

To a solution of hemiacetal 85 (11.3 mg, 23.5 µmol) in NaOAc/AcOH buffer (2 M, pH 4.5, 235 µL) was added oxyamine 72 (21 mg, 117 µmol, 10 equiv) and EtOH (450 µL). The reaction mixture was stirred for 24-48 h at 25-40° C. Purification by P2 size-exclusion chromatography followed by reverse phase chromatography (100% H$_2$O) gave compound 58 (5.07 mg, 7.88 µmol, 33%) as a white fluffy solid.

$^1$H-NMR (500 MHz, D$_2$O) δ4.80 (d, 1H), 4.36 (t, 1H), 4.24-4.17 (m, 2H), 3.93 (dd, 1H), 3.84 (dd, 1H), 3.82 (d, 1H), 3.80-3.74 (m, 2H), 3.73 (dd, 1H), 3.67 (m, 1H), 3.65 (s, 3H), 3.64 (dd, 1H), 3.18 (m, 1H), 3.03-2.96 (m, 5H), 2.74 (t, 2H), 1.94 (t, 2H).

MS (ESI$^-$): m/z 598.19 (calc for C$_{18}$H$_{32}$O$_{15}$S$_3^-$[M−2Na+H]$^-$: m/z 598.04).

Scheme 18: Synthesis of HNK-1-linear polylysine glycoconjugate 86

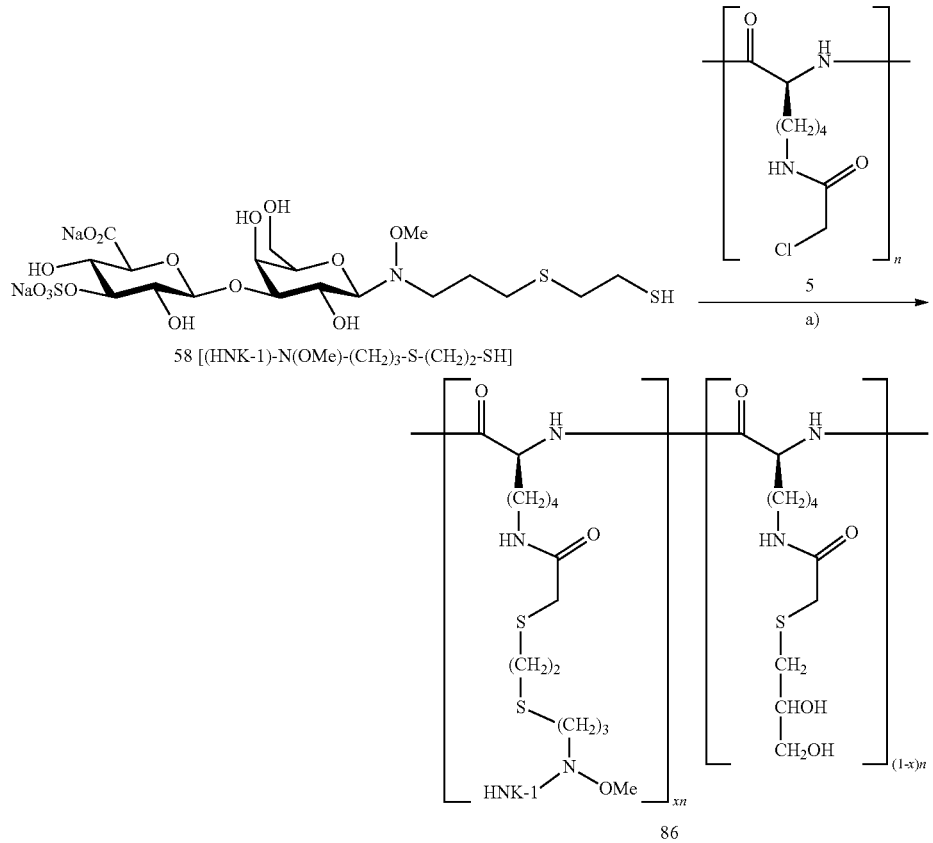

Reagents and conditions: a) i. 5, DBU, DMF/H$_2$O; ii. thioglycerol, Et$_3$N, 87%

HNK-1 Polymer (86)

To a solution of 5 (3.59 mg, 17.5 μmol) in DMF (175 μL) were subsequently added compound 58 (5.07 mg, 7.88 μmol, 0.45 equiv), water (28 μL) and a solution of DBU (3.9 μL, 26 μmol, 1.5 equiv) in DMF (36 μL). After stirring for 1-3 h at rt, thioglycerol (4.5 μL, 53 μmol, 3.0 equiv) and Et$_3$N (7.3 μL, 53 μmol, 3.0 equiv) were added. The reaction mixture was stirred at rt for another 12-24 h. The product was precipitated by slow addition to a stirring solution of EtOH/Et$_2$O (1:1, 1 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave HNK-1 polymer 86 (7.4 mg, 87%) as a white solid. According to $^1$H NMR, the product contained approximately 40% of the lysine side-chains substituted by the carbohydrate epitope 58.

reaction mixture to a stirring solution of Et$_2$O/EtOH (1:1, 2 mL). The precipitate was filtered off, washed with Et$_2$O/EtOH (1:1) and dried to obtain chloroacetylated dendrimer 88 (7.2 mg, 89%) as an off-white solid.

$^1$H NMR (500 MHz, DMSO) δ8.27 (s, 1H), 8.17 (s, 1H), 7.99 (s, 1H), 7.81 (s, 1H), 4.26 (s, 1H), 4.19 (s, 1H), 4.10 (s, 2H), 4.02 (s, 2H), 3.08-2.96 (s, 4H), 1.66-1.17 (m, 12H).

HNK-1/Dentrimeric Polylysine Conjugate (89)

To a solution of 88 (2.12 mg, 10.9 μmol) in DMF (109 μL) were subsequently added compound 58 (3.5 mg, 5.44 μmol, 0.5 equiv), water (20 μL) and a solution of DBU (2.4 μL, 16 μmol, 1.5 equiv) in DMF (22 μL). After stirring for 1-3 h at rt, thioglycerol (2.8 μL, 33 μmol, 3.0 equiv) and Et$_3$N (4.6

Scheme 19: Synthesis of HNK-1-polylysine dendrimer glycoconjugate 86

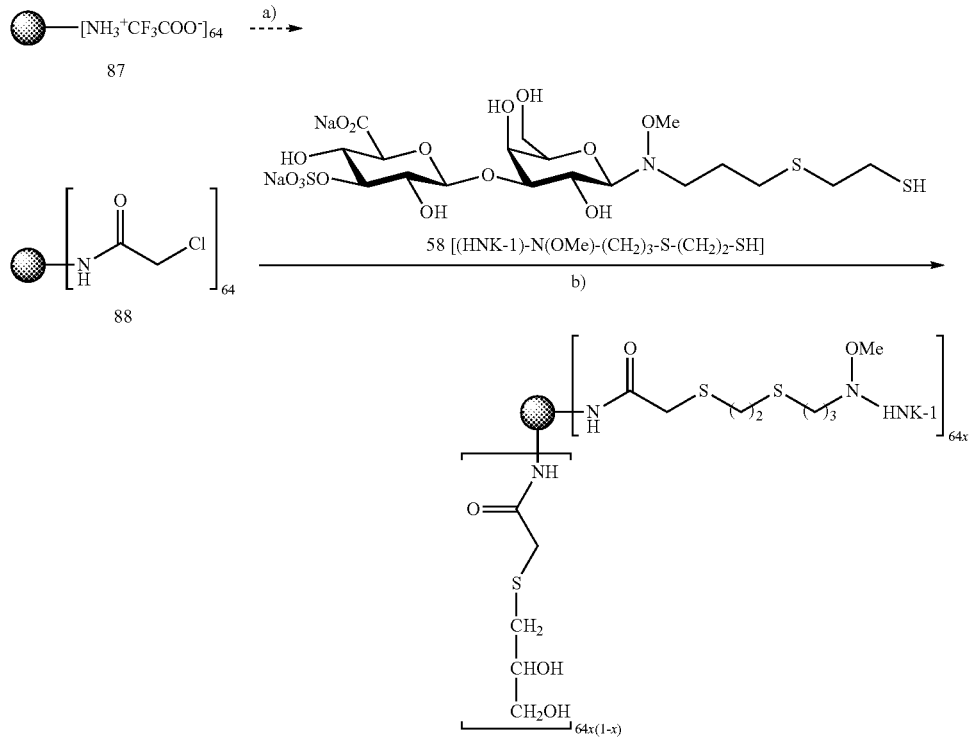

Reagents and conditions: a) (ClAc)$_2$O, DMF/2,6-lutidine, 89%; b) i. 58, DBU, DMF/H$_2$O; ii. thioglycerol, Et$_3$N, 58%

Chloroacetylated Dendrimer (88)

Poly-L-lysine dendrimer (generation 6, 64 outer amine groups, TFA salt, 10 mg, 41.8 μmol) was dissolved under Ar in anhyd DMF/2,6-lutidine (4:1, 130 μL) The solution was cooled to 0° C. and a solution of (ClAc)$_2$O (7.0 mg, 52 μmol, 1.25 equiv) in anhyd DMF (17 μL) was added dropwise. The reaction mixture was stirred overnight at 4° C. After that time, the dendrimer was precipitated by slow addition of the μL, 33 μmol, 3.0 equiv) were added. The reaction mixture was stirred at rt for another 12-24 h. The product was precipitated by slow addition to a stirring solution of EtOH/Et$_2$O (1:1, 2 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave HNK-1/dentrimeric polylysine conjugate 89 (3.54 mg, 58%) as a white solid. According to $^1$H NMR, the product contained approximately 48% of the lysine side-chains substituted by the carbohydrate epitope 58.

Scheme 20: Synthesis of HNK-1-ornithine conjugate 93

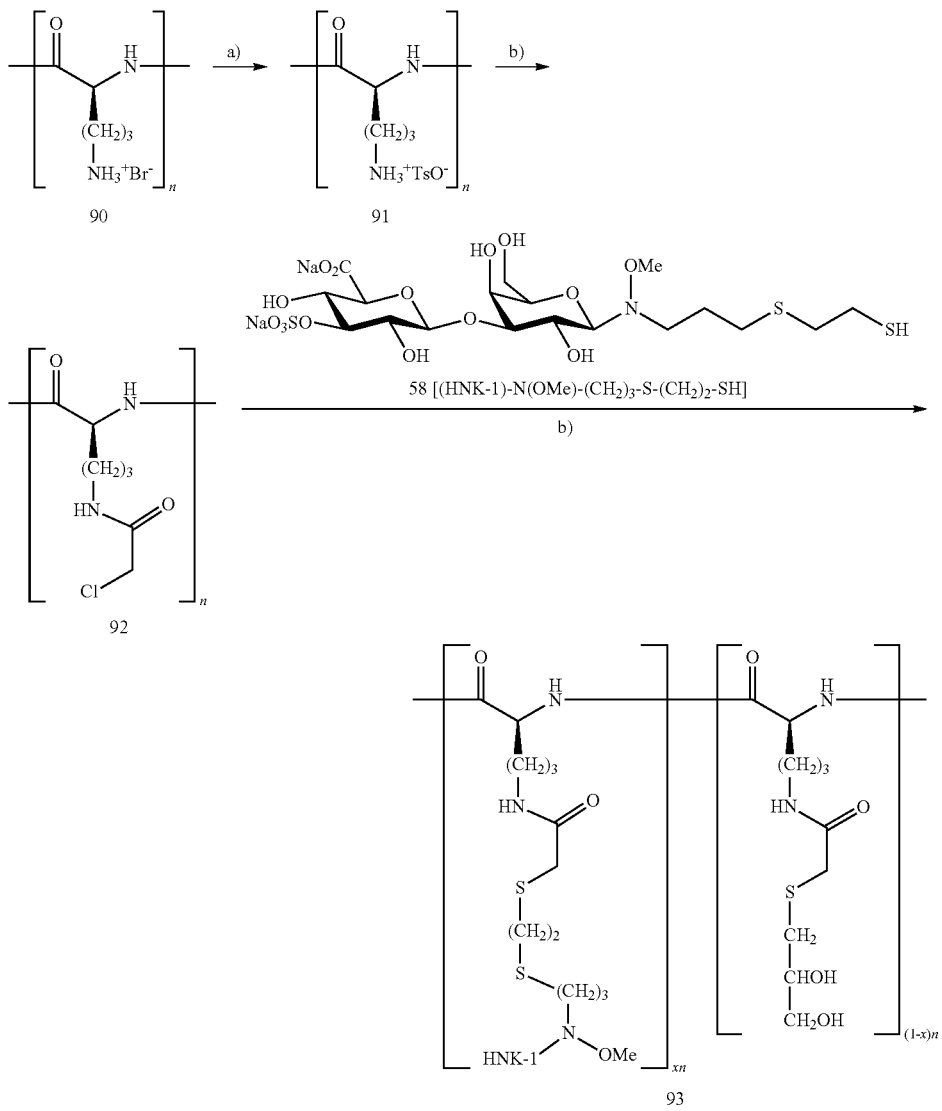

Reagents and conditions: a) i. Resin OH⁻, H₂O; ii. 10% aq PTSA, 91%; b) (ClAc)₂O, DMF/2,6-lutidine, 63%; c) 58, DBU, then thioglycerol, Et₃N, DMF/H₂O, 61%

Tosylate Salt of Poly-L-Ornithine (91)

Poly-L-ornithine hydrobromide (25 mg dissolved in 0.25 ml water) was passed through an anion exchange column, (Ambersep 900 hydroxide form, 5×0.5 cm). The effluent solution was neutralized with 10% aq p-toluenesulfonic acid (PTSA). Lyophilisation gave the tosylate salt of poly-L-ornithine (33.5 mg, 91%) as a white fluffy solid.

$^1$H NMR (500 MHz, D$_2$O) δ7.86 (s, 1H), 7.48 (t, 2H), 7.11 (t, 2H), 4.15 (s, 1H), 2.76 (s, 2H), 1.75-1.46 (m, 4H).

Chloroacetylated Poly-L-Ornithine (92)

The tosylate salt of poly-L-ornithine (33 mg, 116 μmol) was dissolved under Ar in anhyd DMF/2,6-lutidine (4:1, 360 μL) The solution was cooled to 0° C. and a solution of (ClAc)₂O (25 mg, 145 μmol, 1.25 equiv) in DMF (48 μL) was added dropwise. The reaction mixture was stirred overnight at 4° C. After that time, the polymer was precipitated by slow addition of the reaction mixture to a stirring solution of Et₂O/EtOH (1:1, 4 mL). The precipitate was filtered off, washed with Et₂O/EtOH (1:1) and dried to obtain chloroacetylated poly-L-ornitine 92 (14 mg, 73 μmol, 63%) as an off-white solid.

$^1$H NMR (500 MHz, DMSO) δ8.24 (s, 1H), 4.04 (s, 2H), 3.88 (m, 1H), 3.13 (s, 2H), 2-04-1.38 (m, 6H).

HNK-1 Polyornithine Conjugate (93)

To a solution of 92 (2.6 mg, 13.7 μmol) in DMF (137 μL) were subsequently added compound 58 (4.0 mg, 6.17 μmol, 0.45 equiv), water (24 μL) and a solution of DBU (3.1 μL, 21 μmol, 1.5 equiv) in DMF (28 μL). After stirring for 1-3 h at rt, thioglycerol (3.6 μL, 41 μmol, 3.0 equiv) and Et₃N (5.7 μL, 41 μmol, 3.0 equiv) were added. The reaction mixture was stirred at rt for another 12-24 h. The product was precipitated by slow addition to a stirring solution of EtOH/Et$_2$O (1:1, 2 mL). The precipitate was filtered off, washed with EtOH and dried. Further purification was achieved by ultrafiltration (Sartorius Stedim Vivaspin tubes, 6 mL, molecular weight cutoff 10 kDa, 5500 rpm). Freeze-drying gave HNK-1/polyornithine conjugate 93 (4.9 mg, 61%) as a white solid. According to $^1$H NMR, the product contained approximately 60% of the ornithine side-chains substituted by the carbohydrate epitope 58.

0.231 mmol, 78%) as a white fluffy solid. $^1$H-NMR (500 MHz, D$_2$O) δ4.47 (d, 1H), 4.23 (d, 1H), 3.98 (dd, 1H), 3.95 (d, 1H), 3.86-3.77 (m, 3H), 3.75 (m, 1H), 3.71-3.60 (m, 4H), 3.65 (s, 3H), 3.56 (dd, 1H), 3.55 (m, 1H), 3.19 (m, 1H), 3.01 (m, 1H), 2.83 (m, 2H), 2.79 (m, 2H), 2.72 (m, 2H), 1.92 (m, 2H).

MS (ESI$^+$): m/z 528.29 (calc for C$_{18}$H$_{35}$O$_{11}$NS$_2$Na$^+$[M+Na]$^+$: m/z 528.15).

Scheme 21: Synthesis of lactose-linker5 conjugate 56 and conjugate 97

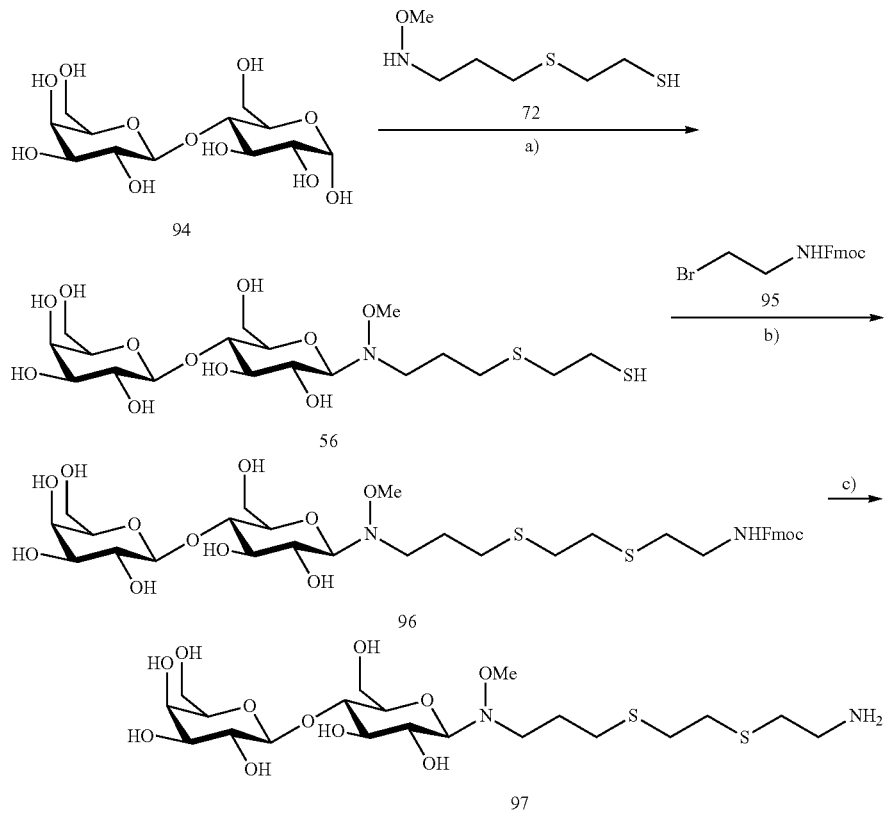

Reagents and conditions: a) 72, AcOH/AcOH buffer, EtOH, 40° C., 78%; b) 95, Cs$_2$CO$_3$, DMF, 75%; c) 20% piperidine in DMF, 64%

N-(O-Methyl N-[2-[2-ethylthio]propylthio]hydroxylamine)-β-D-galactopyranosyl-(1→4)-β-D-glucopyranoside (56)

To a solution of hemiacetal 94 (107 mg, 0.297 mmol) in NaOAc/AcOH buffer (2 M, pH 4.5, 1.5 mL) was added oxyamine 72 (270 mg, 1.50 mmol, 5.0 equiv) and EtOH (3.0 mL). The reaction mixture was stirred for 24-48 h at 25-40° C. After that time, the solvents were evaporated under reduced pressure. The crude residue was suspended under Ar in H$_2$O (5.0 mL). DL-Dithiothreitol (460 mg, 2.98 mmol, 10 equiv) was added to the reaction mixture followed by 1 M aq NaOH (until pH consistently 9). After stirring for 2 h at rt, the reaction mixture was directly loaded onto the C18 column. Purification by reverse phase chromatography (0→100% MeOH in H$_2$O) gave compound 56 (117 mg, N-(O-Methyl N-[2[(2-[2-fluorenylmethyloxycarbamate)ethyl]ethylthio]propylthio]hydroxylamine)-β-D-galactopyranosyl-(1→4)-β-D-glucopyranoside (96)

Thiol 56 (28 mg, 49 μmol) was dissolved in anhyd DMF (1.0 mL). The solution was degazed then flushed with Ar. Bromide 95 (56 mg, 0.163 mmol, 3.3 equiv) and Cs$_2$CO$_3$ (32 mg, 99 μmol, 2.0 equiv) were added to the reaction mixture. After stirring for 2 h at rt under Ar, the reaction mixture was directly loaded onto the C18 column. Reverse phase chromatography eluting with MeCN in H$_2$O (0%→95%) gave the corresponding Fmoc-protected amine 96 (28 mg, 37 μmol, 75%) as a white foam.

$^1$H NMR (500 MHz, MeOD) δ7.81-7.77 (m, 2H), 7.73-7.65 (m, 2H), 7.41-7.36 (m, 2H), 7.33-7.29 (m, 2H), 4.36 (d, 1H), 4.05 (d, 1H), 3.86-3.83 (m, 2H), 3.81 (d, 1H), 3.78 (dd, 1H), 3.70 (dd, 1H), 3.63 (d, 1H), 3.61 (s, 3H), 3.58 (m, 1H), 3.57-3.50 (m, 5H), 3.48 (dd, 1H), 3.33 (m, 1H), 3.12 (m, 1H), 3.00-2.99 (m, 2H), 2.94 (dt, 1H), 2.75-2.62 (m, 6H), 1.89-1.80 (m, 1H), 1.72-1.63 (m, 1H).

MS (ESI+): m/z 793.41 (calc for $C_{35}H_{50}O_{13}N_2S_2Na^+$ [M+Na]+: m/z 793.26).

N-(O-Methyl N-[2-[2-[2-aminoethyl]ethylthio]propylthio]hydroxylamine)-β-D-galactopyranosyl-(1→4)-β-D-glucopyranoside (97)

Derivative 96 (28 mg, 37 μmol) was dissolved under Ar in anhyd DMF (1.0 mL). Piperidine (0.2 mL) was added to the solution under Ar. After stirring for 4 h at rt under Ar, the solvents were coevaporated with toluene (3×). Reverse phase chromatography eluting with MeOH in 0.1% aq TFA (0%→60%) gave the corresponding amine 97 (13 mg, 23.7 μmol, 64%) as a white foam.

$^1$H NMR (500 MHz, D$_2$O) δ4.47 (d, 1H), 4.23 (d, 1H), 3.99 (dd, 1H), 3.95 (d, 1H), 3.85-3.76 (m, 3H), 3.75 (m, 1H), 3.71-3.59 (m, 4H), 3.64 (s, 3H), 3.56 (dd, 1H), 3.55 (m, 1H), 3.26 (t, 2H), 3.18 (m, 1H), 3.01 (m, 1H), 2.92 (t, 2H), 2.88-2.86 (m, 5H), 2.73 (t, 1H), 1.95-1.89 (m, 2H).

MS (ESI+): m/z 549.31 (calc for $C_2H_{41}O_{11}N_2S_2^+$ [M+H]+: m/z 549.21).

Chitosan Derivative (99)

To a solution of chloracetylated chitosan 98 (5.0 mg, 12.2 μmol) in DMF (0.4 mL) were subsequently added compound 56 (24.0 mg, 39.1 μmol, 3.2 equiv) and DBU (7.0 μL, 48.8 μmol, 4.0 equiv). After stirring for 2 h at rt, the reaction mixture was heated at 50° C. for 1 h. After that time, H$_2$O (20 μL) was added and the reaction mixture was stirred at 50° C. for another 1 h. The product was precipitated by slow addition to a stirring solution of EtOH/Et$_2$O (1:1, 4 mL). The precipitate was filtered off, washed with EtOH and dried to obtain chitosan conjugate 99 (12.8 mg, 58%) as a white solid.

IR (KBr) ν 3400 (vs, b, OH), 2926, 2067, 1734 (CO$_{ester}$), 1651 (CO$_{amide}$), 1419, 1382, 1274, 1207, 1119, 1076, 1034, 894, 784, 702, 622, 600

Lactose-Chitosan Conjugate (100)

Chitosan derivative 99 (16 mg, 8.9 μmol) was suspended in 0.1 M aq NaOH (0.32 mL). The suspension was stirred at 40° C. for 90 min. The solid was filtered off, washed with H$_2$O, EtOH and Et$_2$O and dried to obtain lactose-chitosan conjugate 100 (3.7 mg, 59%) as a white solid.

IR (KBr) ν 3436 (vs, b, OH), 2921, 1648 (CO$_{amide}$), 1553, 1377, 1075, 1034, 894

Scheme 22: Synthesis of lactose-chitosan conjugate 100

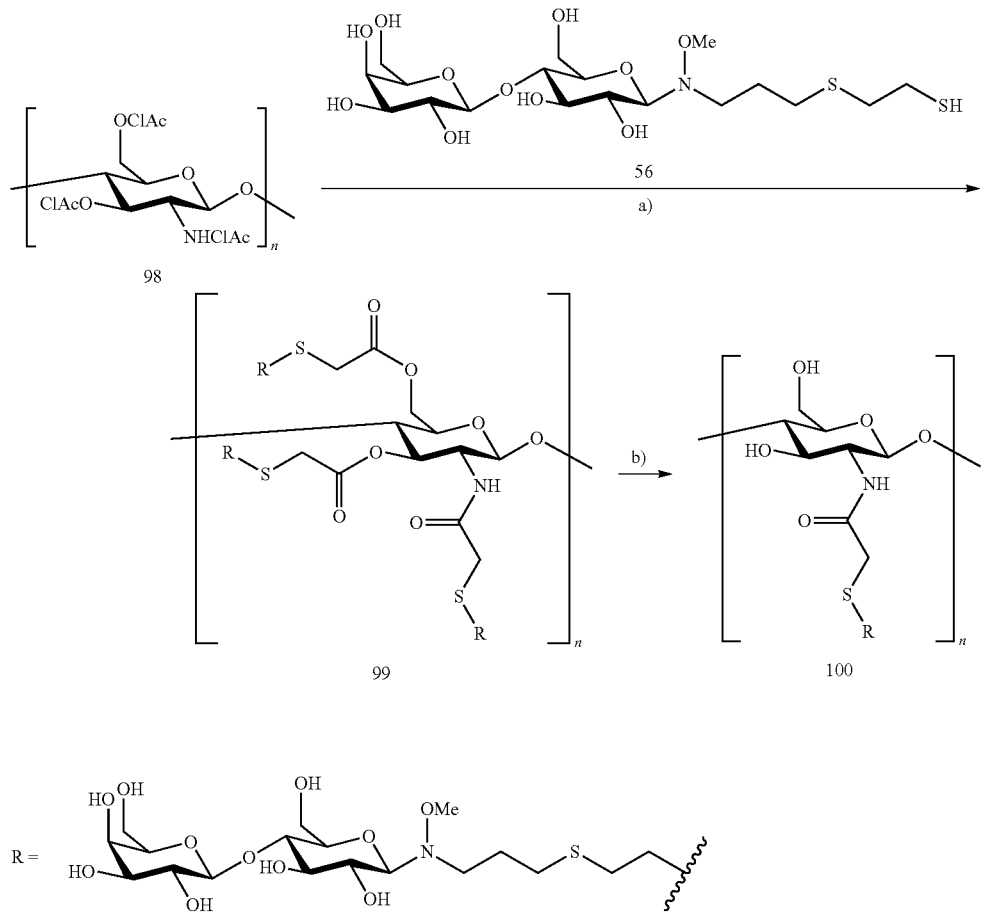

Reagents and conditions: a) 56, DBU, DMF/H$_2$O, 58%; b) 0.1M aq NaOH, 40° C., 59%

Scheme 23: Synthesis of lactose-polyglutamic acid conjugate 102

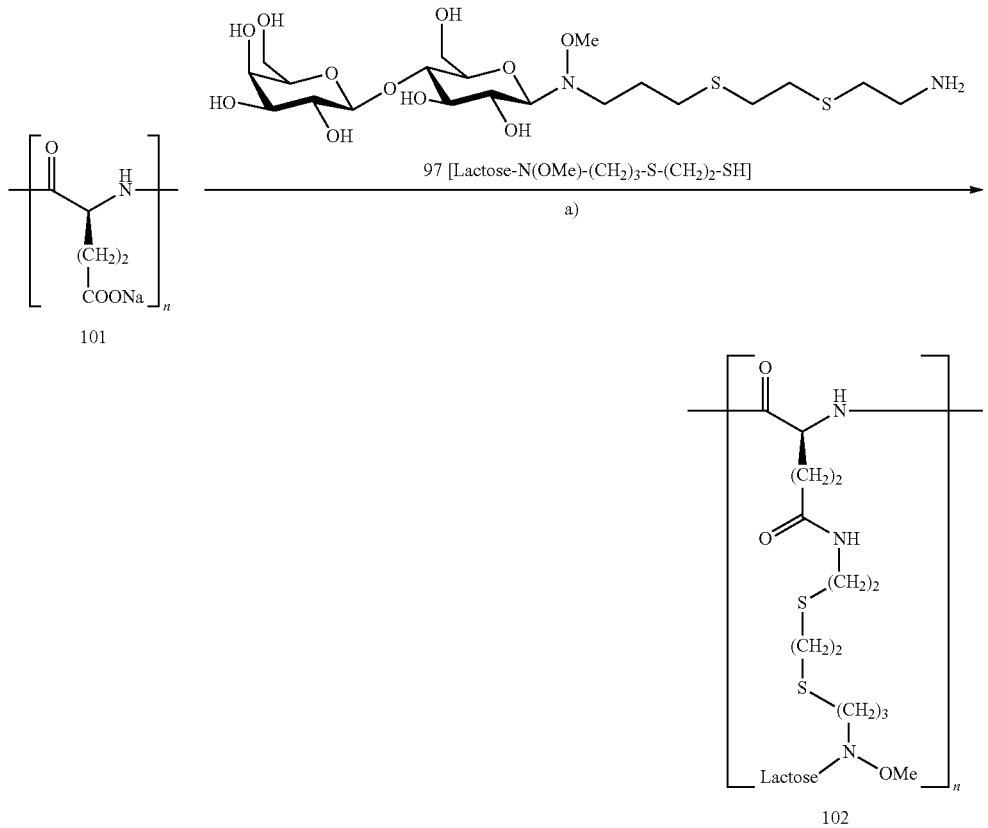

Reagents and conditions: a) Sulfo-NHS, EDC·HCl, NaHCO₃, phosphate buffer, 45%

Lactose-Polyglutamic Acid Conjugate (102)

To a solution of poly-L-glutamic acid sodium salt (from Alamanda Polymers, n=250, 2.50 mg, 16.5 µmol) in phosphate buffer (100 mM, pH 5.0, 81 µL) was added a solution of N-hydroxysulfosuccinimide sodium salt (sulfo-NHS, 60 mg, 0.26 mmol, 15.6 equiv) and N-(3-dimethylaminopropyl)-N'-ethylcarbodiimide hydrochloride (EDC HCl, 37 mg, 0.19 mmol, 11.5 equiv) in phosphate buffer (100 mM, pH 5.0, 417 µL) was added After stirring for 15 min at rt, amine 97 (13 mg, 23.7 µmol, 1.4 equiv) was added followed by addition of satd aq NaHCO₃ until the pH was consistently 7. After stirring for 2 h at rt, ethanolamine was added to the reaction mixture to reach a final concentration of 10 mM. After stirring for 10 min at rt, the reaction mixture was transferred into an ultrafiltration tube (Sartorius Stedim Vivaspin tubes, 6 mL, molecular weight cutoff 10 kDa). Purification by ultrafiltration (5500 rpm) and freeze-drying gave lactose-polyglutamic acid conjugate 102 (4.9 mg, 45%) as a white fluffy solid. According to $^1$H NMR, the product contained approximately 100% of the glutamic acid sidechains substituted by the carbohydrate epitope 56.

Patient Sera

Sera from seven neuropathy patients were investigated. They all were tested positive for anti-ganglioside antibodies in the clinic. Serum anti-ganglioside antibody titers were determined by an ELISA assays from Bühlmann Laboratories (Schönenbuch, Switzerland). Sera were either obtained from Bühlmann Laboratories (Schönenbuch, Switzerland) or the clinical laboratory of the University Hospital Basel (Basel, Switzerland). Sera from individuals undergoing neuro-immunological evaluation with negative anti-ganglioside reactivity served as control. Use of sera for our study was approved by the ethics committee of northwestern and central Switzerland (EKNZ UBE-15/46).

Competitive Binding Assay

The synthesized carbohydrate polymers 6 (GM1a epitope), 26 (GD1b epitope), and 34 (GT1a epitope) were tested in the GanglioCombi(-Light) ELISA and/or, in case of compound 6, the anti-GM1 ELISA (all kits from Bühlmann Laboratories, Schönenbuch, Switzerland). The 96 well microtiter plates coated with purified gangliosides from bovine cauda equina were washed two times with washing buffer (300 µl/well) before adding the carbohydrate polymers in eight different concentrations, 25 µl/well. The patient sera containing anti-ganglioside IgG or IgM antibodies were added in the appropriate dilutions, 25 µl/well (2× concentrated), to obtain a total of 50 µl volume per well. The plate was covered with a plate sealer and incubated for 2 h at 4-8° C. The wells were washed three times with wash buffer (300 µl/well) before either the anti-human IgM antibody-horseradish peroxidase conjugate or the anti-human IgG antibody-horseradish peroxidase conjugate was added (100 µl/well). The plate was incubated for 2 h at 4-8° C. After washing the wells (3×300 µl/well), a substrate solution of tetramethylbenzidin (TMB in citrate buffer with hydrogen peroxide) was added (100 µl/well) and the plate incubated for further 30 minutes at 600 rpm and room temperature, protected from light. Finally, a stop solution (0.25 M sulfuric acid) was added (100 μl/well) and the degree of colorimetric reaction was determined by absorption measurement at 450 nm with a microplate reader (Spectramax 190, Molecular Devices, California, USA).

The synthesized carbohydrate polymer 86 (HNK-1 epitope mimetic 58) was tested in the anti-MAG ELISA (kit from Bühlmann Laboratories, Schönenbuch, Switzerland). The assay protocol was performed according to the one described above for the GanglioCombi(-Light) ELISA. To determine the in vitro $IC_{50}$ of polymer 86, the assay was performed with co-incubation of polymer (25 μl/well) and a mouse monoclonal anti-HNK-1 (anti-MAG) IgM antibody (25 μl/well) at a final dilution of 1:1000. To determine the in vivo efficacy of polymer 86, the assay was performed by incubation of mouse plasma diluted 1:100 (50 μl/well). Both, the mouse monoclonal anti-HNK-1 (anti-MAG) IgM and anti-HNK-1 (anti-MAG) IgM in plasma of immunized BALB/c mice (pre- and post-treatment) were detected with goat anti-mouse IgM HRP conjugate (Sigma Aldrich, A8786) diluted 1:10'000.

Immunological Mouse Model for Anti-MAG Neuropathy

Six gender matched BALB/c wild type mice at the age of 6 weeks were injected subcutaneously at multiple sites on the lower back with a total of 100 μg of the glycosphingolipids SGPG and SGLPG purified from bovine cauda equina (both glycolipids contain the HNK-1 carbohydrate epitope). The isolation of glycolipids was performed according to a protocol described by Burger et al. (*Journal of Immunological Methods* 1991, 140, 31-36). These glycosphingolipids were taken up in PBS, mixed with KLH (1.4 mg/ml final concentration) and emulsified with an equal volume of TiterMax® Gold. Two booster injections were performed after 2 and 4 weeks with 20 μg of purified SGPG/SGLPG mixed with KLH and TiterMax® Gold. Blood samples were taken by puncture of the tail vein and transferred to tubes containing 1 μl of 0.5 M EDTA and centrifuged 15 min at 1'800 rpm. The supernatant (plasma) was transferred to new tubes and stored at −55° C. The glycopolymer 86, dissolved in PBS, was administered by i.v. injection of the tail vein. Mouse plasma samples were analyzed by the above described anti-MAG ELISA.

As indicated, the synthesized carbohydrate polymers 6 (GM1a epitope), 26 (GD1b epitope), and 34 (GT1a epitope) were tested in the GanglioCombi(-Light) ELISA and/or, in case of compound 6, the anti-GM1 ELISA (all kits from Bühlmann Laboratories, Schönenbuch, Switzerland). These ELISAs are used to support the clinical diagnosis of immune-mediated neuropathies. The assays allow the determination of the anti-ganglioside IgM/IgG antibodies titer (e.g. gangliosides GM1, GD1a, and GQ1b) in serum samples from patients. We used these ELISAs as competitive binding assays. The synthesized compounds and patient serum samples (containing anti-ganglioside antibodies) were given into 96 well plates, coated with purified gangliosides from bovine cauda equina. Immobilized gangliosides and the synthesized compounds competed for binding to the anti-ganglioside antibodies. After a washing step ganglioside-bound antibodies (IgM/IgG) were detected with horseradish peroxidase labeled anti-human IgM or anti-human IgG antibodies, followed by a colorimetric reaction. Successful competition of the compounds with gangliosides led to a decrease in measured $OD_{450}$ nm, (optical density), because they block the binding sites of anti-ganglioside antibodies, preventing their binding to immobilized gangliosides. The principle of the assay is depicted in FIG. 1. For the evaluation of the compounds, sera from seven patients (anti-GM1a: PP IgG Pos., P21, P3, P4; anti-GD1b: P22; anti-GQ1b: EK-GCO 1803, P23), tested positive for anti-ganglioside reactivity during clinical laboratory routine analysis, were chosen. IgG and IgM antibody titers were determined for each serum in preliminary experiments. Serum dilutions with measured $OD_{450}$ nm values around 1.0 (0.7-1.3) were chosen for the assay, to be able to compare the measured $IC_{50}$ values (half maximal inhibitory concentration) which are antibody concentration dependent. Serum dilutions: PP IgG Pos. 1:1'200, P21 1:1'300, P3 1:50, P4 1:400, P22 1:50, EK-GCO 1803 1:300, P23 1:50). The sera that served as negative controls (dilution 1:50) showed no antibody binding to gangliosides.

$IC_{50}$ values of compound 6 were determined for sera PP IgG Pos. (IgG), P21 (IgG), P3 (IgM) and P4 (IgM). Compound 26 were evaluated with serum P22 (IgG). The $IC_{50}$ values of compound 34 were determined for sera EK-GCO 1803 (IgG) and P23 (IgG). The results are shown in the Table below. The inhibition curves are shown in FIG. 2.

TABLE $IC_{50}$ values of glycopolymers 6, 26, and 34 tested with a total of seven neuropathy patient sera including standard deviations.

| Serum | Ganglioside reactivity (antibody isotype) | Compound 6 PL(GM1a)$_{28}$ $IC_{50}$ | Compound 26 PL(GD1b)$_{20}$ $IC_{50}$ | Polymer 34 PL(GT1a)$_{58}$ $IC_{50}$ |
| --- | --- | --- | --- | --- |
| PP IgG Pos. | GM1a (IgG) | 28.0 ± 13.5 μM | | |
| P21 | GM1a (IgG) | 218.6 ± 77.8 nM | | |
| P3 | GM1a (IgM) | 374.9 ± 157.0 nM | | |
| P4 | GM1a (IgM) | 59.4 ± 62.9 pM | | |
| P22 | GD1a (IgG) | | 313.1 ± 112.3 μM | |
| EK-GCO 1803 | GQ1b/GT1a (IgG) | | | 12.5 ± 4.1 μM |
| P23 | GQ1b/GT1a (IgG) | | | 347.6 ± 92.0 μM |

The inventive polymers 6, 26, 34 are glycopolymers that imitate the natural glycoepitopes of the GM1a-, GD1b-, and the GT1a-gangliosides. These and other glycoepitopes are involved in autoimmune neurological diseases; they are targets for antibodies that trigger demyelination and neuro-degeneration (H. J. Willison and N. Yuki, Brain, 2002, 125, 2591-2625). The prepared glycopolymers are based on a biodegradable poly-L-lysine backbone and are designed for a therapeutic application in patients, where pathogenic anti-glycan antibodies could be selectively neutralized and removed by these polymers.

For the biological evaluation of the prepared glycopolymers, patient sera were used. These sera have been tested positive in the clinic for anti-ganglioside antibodies. The synthetic glycopolymers were tested with sera presenting an antibody response against the ganglioside epitopes displayed by the conjugates (e.g. sera with anti-GM1a IgG or IgM antibodies for the evaluation of the PL(GM1a)$_{28}$ polymer 6). The $IC_{50}$ values obtained during the biological characterization in the competitive binding ELISA assay showed the different neutralization effects of the glycopolymers for anti-ganglioside antibodies from different patients with reactivity against the same glycoepitope. This is probably due to interindividual differences of antibody characteristics (isotype, affinity, specificity, serum concentration, monoclonal/polyclonal, etc.) between the different patients. However, the inhibitory effect of the glycopolymers is given for antibody reactivities against different gangliosides. Furthermore, the data on compound 6 shows that glycopolymers mimicking a specific glycoepitope can neutralize antibodies of different isotypes, e.g. antibodies of the IgG and/or the IgM type. It is also interesting to note, that partial glycoepitope structures can be sufficient to retain affinity to anti-ganglioside antibodies. This is the case for the competitive binding assay of GT1a-glycoconjugate 34 with sera EK-GCO 1803 (IgG) and P23 (IgG), where the antibodies target the GQ1b epitope (characteristic for e.g. Miller-Fischer syndrome and Bickerstaff brainstem encephalitis). Even though the GT1a epitope, displayed by conjugate 34, lacks one sialic acid compared to the GQ1b ganglioside, the patient sera directed against GQ1b were neutralized by glycopolymer 34.

Figure 2A:
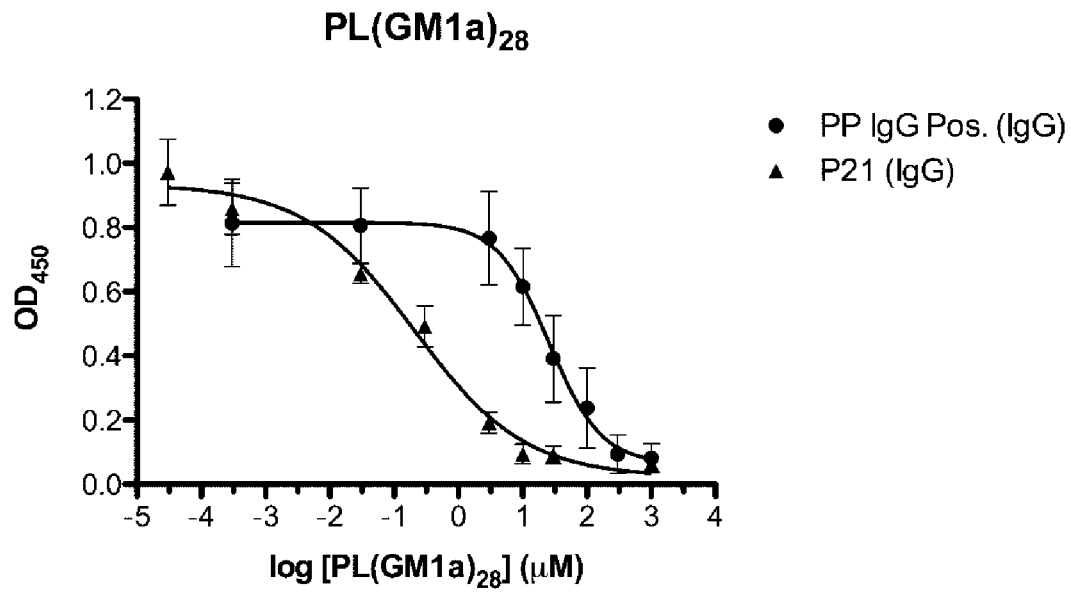
FIG. 2A: The GM1a-ganglioside-coated wells were co-incubated with compound 6 (1 mM highest concentration) and the two patient sera PP IgG Pos. (IgG), P21 (IgG). Compound 6 is a polylysine polymer (average of 250 repeating lysine units) with a defined percentage of lysine residues coupled to the GM1a glycoepitope (4). The general abbreviation used is as follows: PL(glycoepitope)$_x$ with x defining the percentage of glycoepitope loading in %. In this case the polymer is PL(GM1a)$_{28}$. Results are indicated as mean±SD.
Figure 2B:
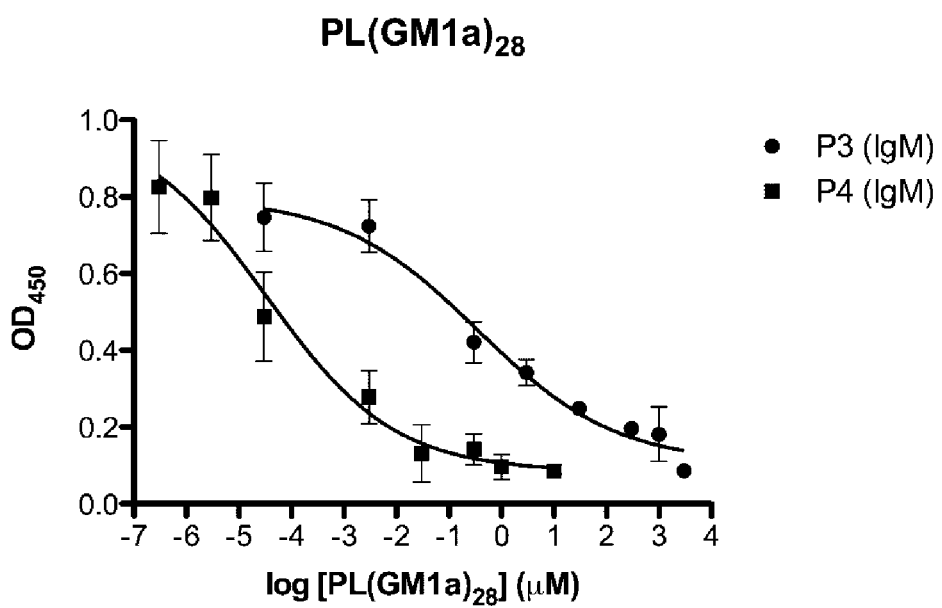
FIG. 2B: Co-incubation of GM1a-coated wells with PL(GM1a)$_{28}$ polymer 6 (3 mM highest concentration) together with patient sera P3 (IgM) and P4 (IgM). Results are indicated as mean±SD.
Figure 2C:
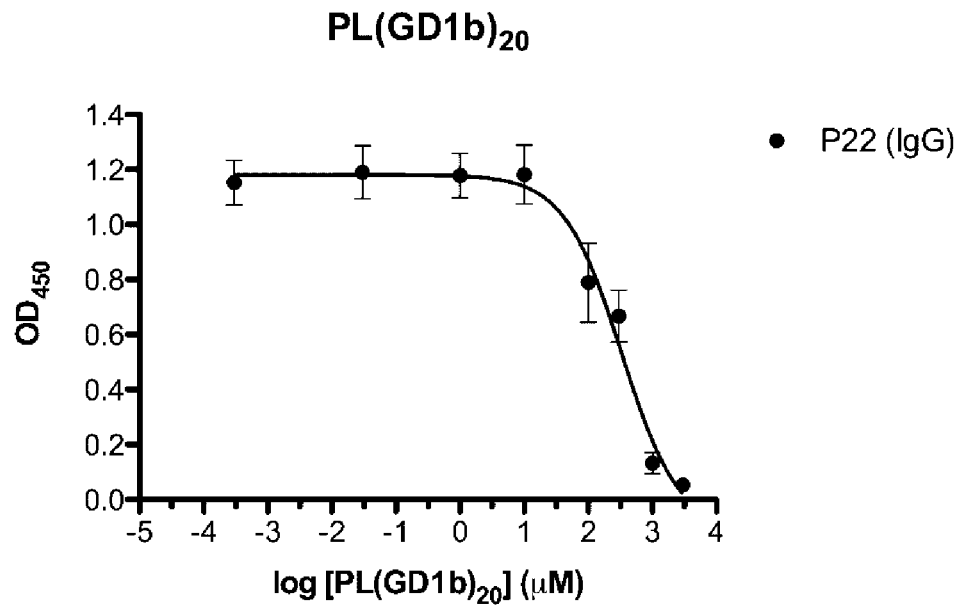
FIG. 2C: Co-incubation of GD1b-coated wells with the PL(GD1b)$_{20}$ polymer 26 (3 mM highest concentration) together with patient sera P22 (IgG). Results are indicated as mean±SD.
Figure 2D:
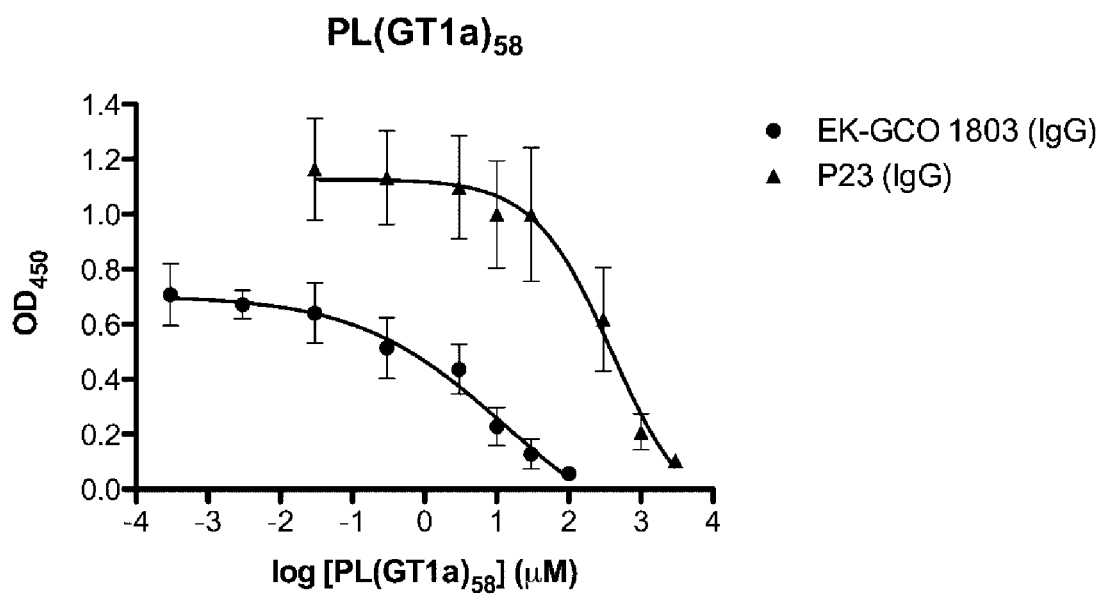
FIG. 2D: Co-incubation of GQ1b-coated wells with the PL(GT1a)$_{58}$ polymer 34 (3 mM highest concentration) together with patient sera EK-GCO 1803 (IgG), P23 (IgG). Results are indicated as mean±SD.
Figure 2E:
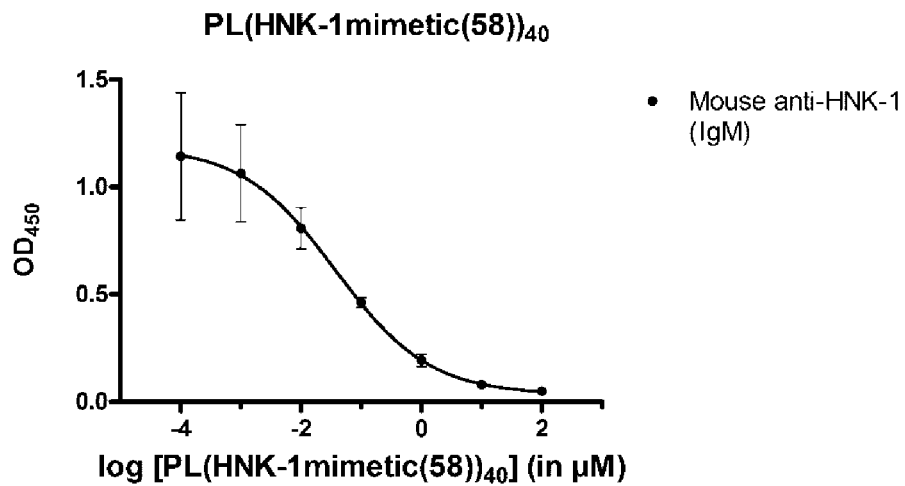
FIG. 2E: Co-incubation of MAG-coated wells (MAG contains up to eight HNK-1 glycoepitopes) and the PL(HNK-1mimetic(58))$_{40}$ polymer 86 (100 µM highest concentration) together with a mouse monoclonal anti-HNK-1 IgM antibody. Results are indicated as mean±SD.

The $IC_{50}$ value of compound 86 was determined for the mouse monoclonal anti-HNK-1 IgM antibody. This antibody shows comparable reactivity with the HNK-1 glycoepitope as monoclonal anti-MAG IgM antibodies of anti-MAG neuropathy patients. The results are shown in the Table 2 below. The inhibition curve is shown in FIG. 2E.

TABLE 2

$IC_{50}$ value of glycopolymer 86, tested with the mouse monoclonal anti-HNK-1 IgM antibody including standard deviation.

| Antibody | Glycoepitope reactivity (antibody isotype) | Compound 86 PL(HNK-1mimetic(58))$_{40}$ $IC_{50}$ |
|---|---|---|
| Mouse anti-HNK-1 antibody | HNK-1 (IgM) | 51.3 ± 44.2 nM |

Figure 3:
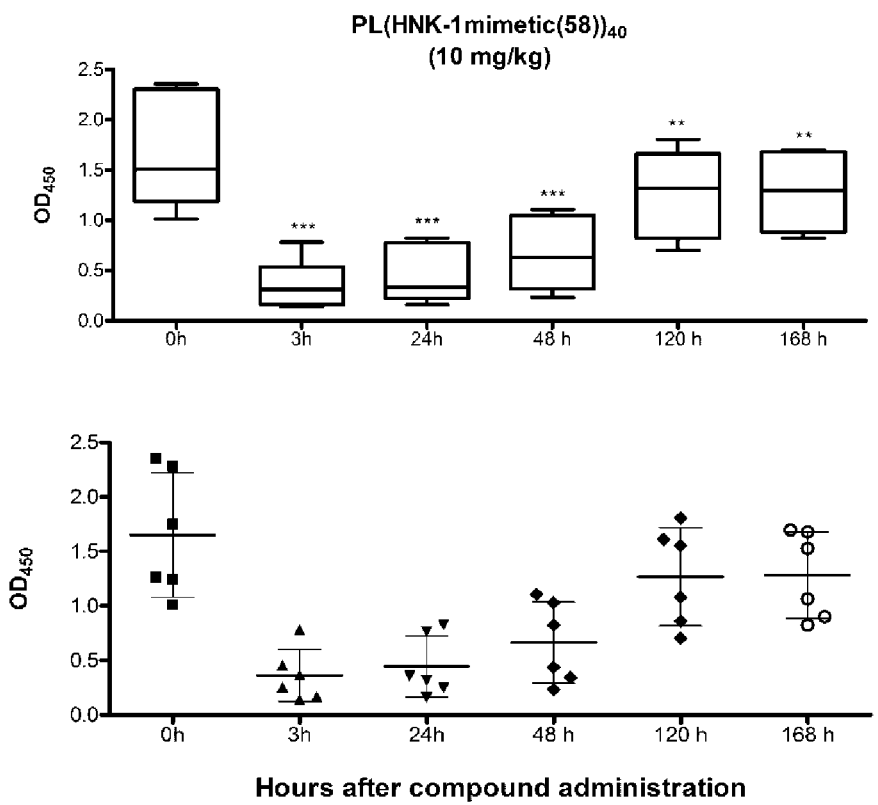
FIG. 3: BALB/c wild type mice were immunized against the two glycosphingolipids SGPG and SGLPG, of which both bear the HNK-1 glycoepitope. Immunized mice showed high levels of anti-HNK-1 (anti-MAG) IgM antibodies at day 154 after immunization (0 h, pre-treatment). These induced mouse antibodies are a model for human anti-MAG IgM of anti-MAG neuropathy patients. An intravenous administration of the PL(HNK-1mimetic(58))$_{40}$ polymer 86 (10 mg/kg) to immunized BALB/c mice (n=6) led to a significant reduction of anti-HNK-1 (anti-MAG) IgM antibodies for up to a week (168 h) after administration. Results are indicated as mean±95% CI (above) and mean±SD (below). Results were analyzed by one-way ANOVA with Dunnett's multiple comparison posttest with a 0.05 confidence level accepted for statistical significance (*p≤05, p≤0.01, *p≤0.001).

The inventive polymer 86 is a glycopolymer that imitates the natural trisaccharide glycoepitope HNK-1 which is present in the peripheral nervous system as part of the glycosphingolipids SGPG and SGLPG but also the glycoprotein MAG. This HNK-1 glycoepitope is the target of an autoimmune attack in the neurological disorder anti-MAG neuropathy. The prepared glycopolymer is based on a biodegradable poly-L-lysine backbone of an average of 400 lysines, wherein 40% of the lysine side chains are loaded with the HNK-1 mimetic 58. The remaining 60% of side chains are caped with thioglycerole to improve the water solubility of the polymer. The polymer is designed for a therapeutic application in anti-MAG neuropathy patients (or patients with other neurological diseases with the same or similar antibodies), where pathogenic anti-HNK-1 (MAG/SGPG/SGLPG) antibodies could be selectively neutralized and removed by this polymer. Polymer 86 inhibits the binding of the mouse monoclonal anti-HNK-1 IgM to the HNK-1 epitope on MAG at nanomolar concentrations (Table 2). The therapeutic utility of polymer 86 is further supported by in vivo data (FIG. 3). The compound PL(HNK-1mimetic(58))$_{40}$ was administered intravenously to immunized BALB/c mice (n=6) with induced high levels of anti-HNK-1 (anti-MAG) IgM antibodies. These mouse antibodies are a model for pathogenic human anti-HNK-1 (anti-MAG) IgM antibodies of anti-MAG neuropathy patients. A dose of 10 mg/kg or polymer 86 significantly reduced the levels of mouse anti-HNK-1 (anti-MAG) IgM antibodies up to seven days after administration.

The invention claimed is:
1. A polymer comprising:
an α-amino acid polymer backbone; and
at least two carbohydrate moieties of formula 25* or 33* or a salt thereof that mimic a GD1b or GT1a glycoepitope comprised by a glycosphingolipid of the nervous system wherein each carbohydrate moiety is covalently connected to the polymer backbone via a linker Z, wherein:
formula 25* is formula 33* is and
the linker Z is selected from any one of formula (a) to (g):

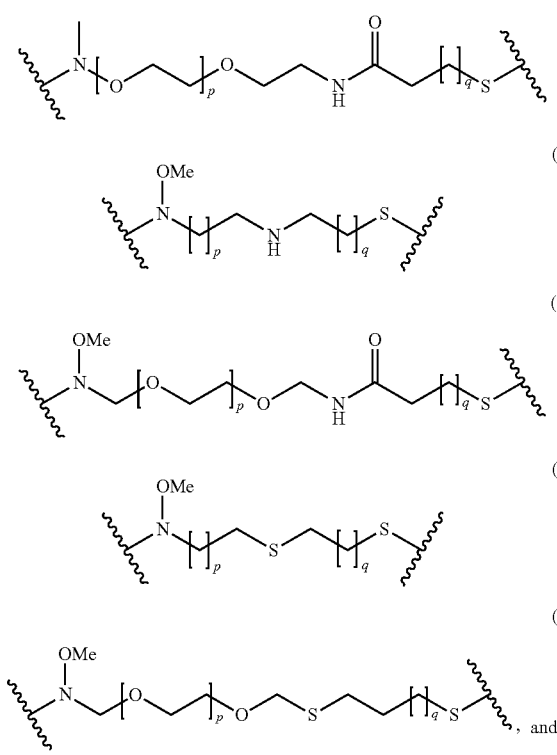

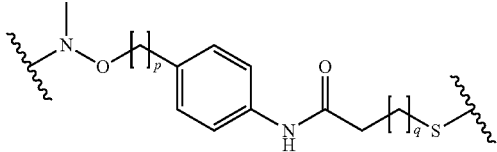

wherein:
p is 0 to 6, and q is 0 to 6; and
Z is covalently bound via its terminal —N atom to the reducing end of said carbohydrate moiety and covalently bound to said a-amino acid polymer backbone via its terminal S— atom and via an optional spacer moiety.

2. The polymer according to claim 1, wherein the linker Z is of formula (b).

3. The polymer according to claim 1, wherein the α-amino acid polymer backbone is poly-lysine or poly-ornithine.

4. The polymer according to claim 1, wherein the percentage of loading of the carbohydrate moieties onto the polymer backbone is between 10 and 90%.

5. The polymer according to claim 1, wherein the α-amino acid polymer backbone comprises amino acid residues selected from lysine, ornithine, glutamic acid and aspartic acid.

6. The polymer according to claim 3, wherein the α-amino acid polymer backbone is poly-L-lysine or poly-D-lysine.

7. The polymer according to claim 6, wherein the carbohydrate moieties are of formula 25*

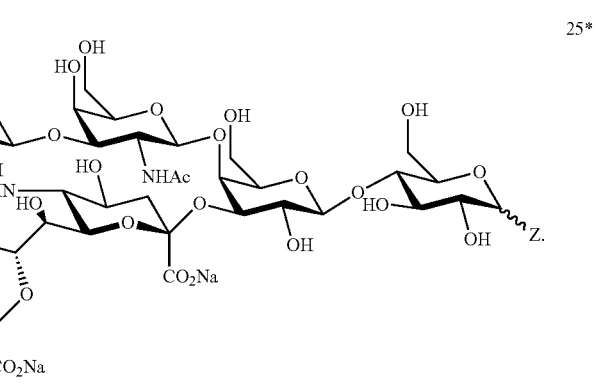

8. The polymer according to claim 6, wherein the carbohydrate moieties are of formula 33*

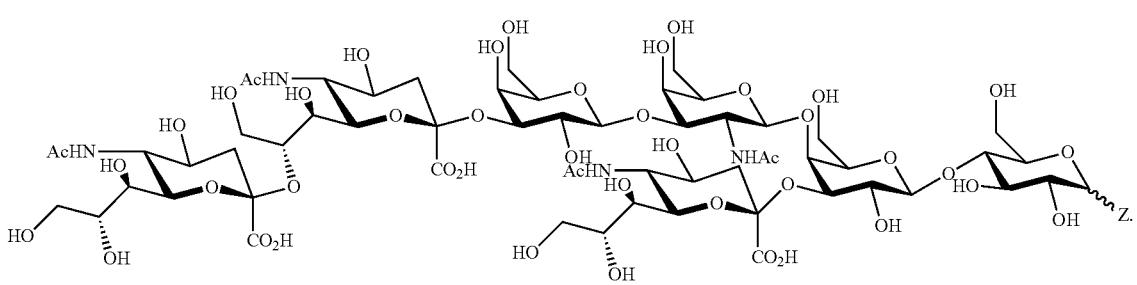

9. The polymer according to claim 7, wherein the α-amino acid polymer backbone is poly-lysine, and wherein each Z is connected via its terminal S— atom to the —CH₂ group of a spacer moiety of formula —CH₂CO—, and the spacer moiety is connected to a lysine sidechain via an amide bond.

10. The polymer according to claim 9, wherein the percentage of loading of the carbohydrate moieties onto the polymer backbone is between 30 and 60%.

11. The polymer according to claim 8, wherein the α-amino acid polymer backbone is poly-lysine, and wherein each Z is connected via its terminal S— atom to the —CH₂ group of a spacer moiety of formula —CH₂CO—, and the spacer moiety is connected to a lysine sidechain via an amide bond.

12. The polymer according to claim 11, wherein the percentage of loading of the carbohydrate moieties onto the polymer backbone is between 30 and 60%.

13. The polymer according to claim 10, wherein the carbohydrate moieties connected to lysine sidechains of the α-amino acid polymer backbone are of formula 25:

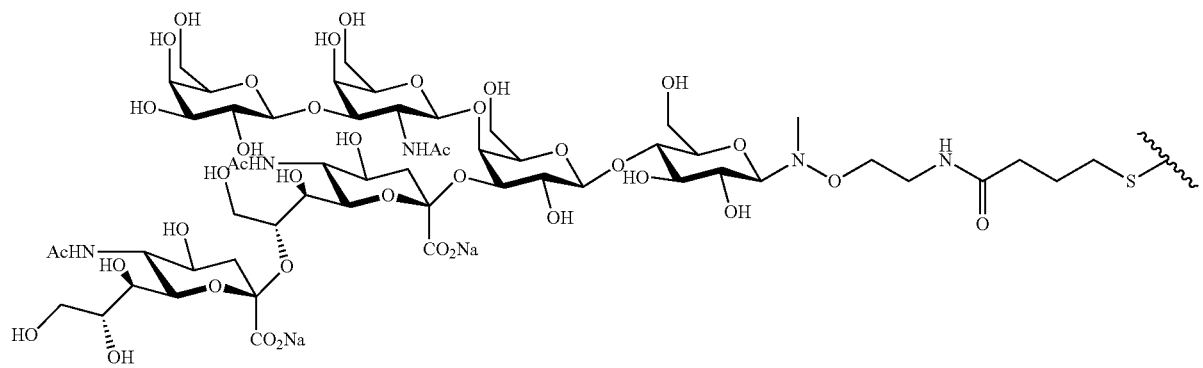

25 and wherein the remaining lysine sidechains of the α-amino acid polymer backbone are capped with —COCH₂SCH₂CH(OH)CH₂OH.

14. The polymer according to claim 13, wherein the carbohydrate moieties connected to lysine sidechains of the α-amino acid polymer backbone are of 33:

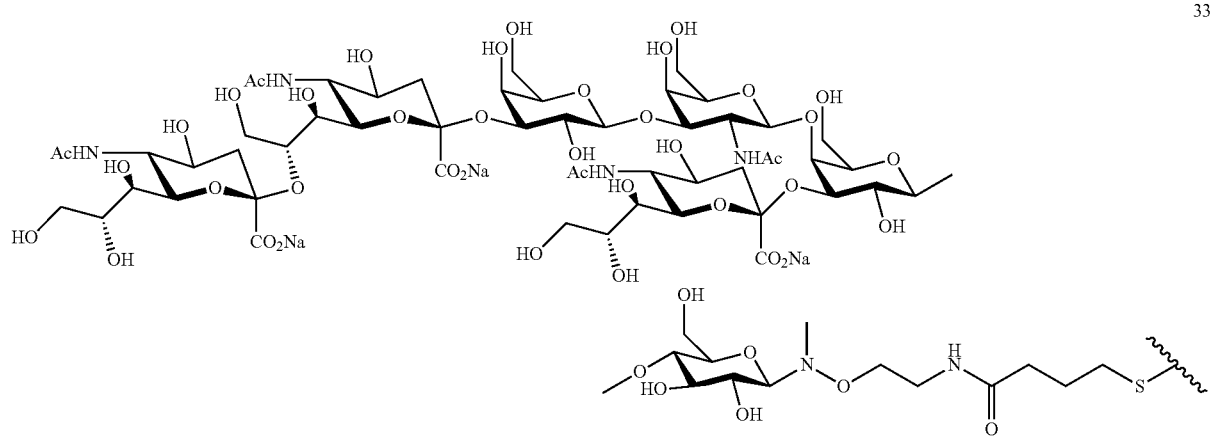

33 and wherein the remaining lysine sidechains of the α-amino acid polymer backbone are capped with 2,3-dihydroxypropylthioacetyl.

* * * * *